US005516759A

United States Patent [19]

Swenson et al.

[11] Patent Number: 5,516,759

[45] Date of Patent: May 14, 1996

[54] LHRH ANTAGONISTS HAVING LACTAM GROUPS AT THE N-TERMINUS

[75] Inventors: Rolf E. Swenson, Grayslake; Fortuna Haviv, Deerfield; Nicholas A. Mort, Waukegan, all of Ill.

[73] Assignee: TAP Holdings Inc., Deerfield, Ill.

[21] Appl. No.: 352,305

[22] Filed: Dec. 8, 1994

[51] Int. Cl.[6] .............................. A61K 38/09; C07K 7/23

[52] U.S. Cl. ............................ 514/15; 530/313; 930/130

[58] Field of Search .............................. 514/15; 930/130; 530/313, 328

[56] References Cited

U.S. PATENT DOCUMENTS

| | | | |
|---|---|---|---|
| 4,307,083 | 12/1981 | Rivier et al. | 530/313 |
| 4,481,190 | 11/1984 | Nestor et al. | 530/313 |
| 4,851,385 | 7/1989 | Roeske | 530/313 |

OTHER PUBLICATIONS

Peptides: Synthesis, Structure, Function, Proceedings American Peptide 7th Symp., published 1981, Freidinger, "Computer Graphics and Chemical . . . ", pp. 673–683.

*Primary Examiner*—Jeffrey E. Russel
*Attorney, Agent, or Firm*—Jerry F. Janssen

[57] ABSTRACT

Peptides possessing LHRH antagonistic activity, and useful for the controlling the release of LHRH in mammals are decapeptide analogues of LHRH having a lactam group at the N-terminus of the formula

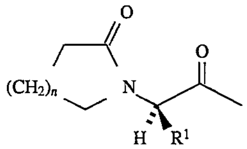

where n is 1, 2, or 3 and $R^1$ is selected from the group consisting of hydrogen, benzyl, 4-chlorobenzyl, 2-methyl-naphth-1-yl, 1-methylnaphth-2-yl, and quinolin-3-ylmethyl.

6 Claims, No Drawings

LHRH ANTAGONISTS HAVING LACTAM GROUPS AT THE N-TERMINUS

TECHNICAL FIELD

The present invention relates to organic compounds having biological activity, to compositions containing the compounds, and to medical methods of treatment. More particularly, the present invention concerns certain N-terminus modified peptides having LHRH antagonist activity, pharmaceutical compositions containing the peptides, and a method of inhibiting LHRH activity in a mammal in need of such treatment.

BACKGROUND OF THE INVENTION

The gonadotropins: follicle stimulating hormone (FSH), luteinizing hormone (LH), and chorionic gonadotropin (CG), are required for ovulation, spermatogenesis, and the biosynthesis of sex steroids. A single hypothalamic hormone, gonadotropin-releasing hormone GnRH (also known as luteinizing hormone-releasing hormone, LHRH) is responsible for regulating the secretion of both FSH and LH in mammals.

The structure of LHRH was determined by A. V. Schally, et al., *Science, 173:1036–1037* (1971). Early attempts to prepare peptides having LHRH-like activity centered on the synthesis of compounds which were LHRH agonists. However, in 1976 it was found that while individual doses of LHRH stimulated the release of gonadotropin, the continuous administration of small doses of LHRH or chronic administration of LHRH agonists had the opposite effect. This finding stimulated research for the discovery of both agonist and antagonist analogs of LHRH as agents useful for regulating sex steroids in mammals. A considerable number of patents and articles in the open literature disclose analogs of LHRH which either act as agonists of LHRH (i.e. act to stimulate the release of LH and FSH) or as antagonists of LHRH (i.e. act to inhibit the release of LH and FSH). For the most pan, these compounds contain nine or ten aminoacyl residues, substituting naturally-occurring or non-naturally-occurring amino acid residues at one or more positions in the natural sequence of LHRH. In some cases, active antagonists of LHRH have been reported which contain fewer than ten amino acid residues.

The literature has reported that LHRH antagonists are useful for the treatment of a variety of conditions in which the suppression of sex steroids plays a as key role including contraception, delay of puberty, treatment of benign prostatic hyperplasia, palliative treatment or remission of hormonal-dependent tumors of the breast and ovaries, palliative treatment or remission of hormonal-dependent tumors of the prostate, the treatment of cryptoorchidism, hirsutism in women, gastric motility disorders, dysmenorrhea, and endometriosis.

SUMMARY OF THE INVENTION

The present invention provides, in its principle embodiment, a class of peptide antagonist analogs of LHRH which have been modified at the N-terminus by addition of a lactam group. The compounds of the present invention inhibit the secretion of gonadotropins by the pituitary gland and inhibit the release of steroids by the gonads.

In its principal embodiment, the invention provides a peptide of the formula:

$$X—B—C—D—E—F—G—H—I—J—NH_2$$

or a pharmaceutically accaptable salt thereof where X is a lactam group of the formula:

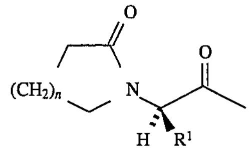

where n is 1, 2, or 3 and $R^1$ is selected from the group consisting of hydrogen, benzyl, 4-chlorobenzyl, 2-naphthylmethyl, 1-naphthylmethyl, and 3-quinolinylmethyl.

B is an aminoacyl residue selected from the group consisting of D-phenylalanyl, D-3-(4-chlorophenyl)alanyl, D-3-(4-fluorophenyl)alanyl, and D-3-(naphth-2-yl)alanyl.

C is an aminoacyl residues independently selected from the group consisting of D-3-(pyrid-3-yl)alanyl, glycyl, D-3-(naphth-1-yl)alanyl, D-alanyl, and D-tryptophyl.

D is an aminoacyl residue selected from the group consisting of L-seryl, $N^{\alpha}$-methyl-L-seryl, glycyl, and threonyl.

E is an aminoacyl residue selected from the group consisting of L-tyrosyl, $N^{\alpha}$-methyl-L-tyrosyl, $N^{\alpha}$-methyl-L-phenylalanyl, ($N^{\epsilon}$ -nicotinyl)-L-lysyl, ($N^{\epsilon}$-picolinyl)-L-lysyl, 3-(4-(3-amino- 1,2,4-triazol-5-yl)phenyl)alanyl, and $N^{\alpha}$ -methyl-3-(4-(3-amino-1,2,4-triazol-5-yl)phenyl)alanyl.

F is an aminoacyl residue selected from the group consisting of ($N^{\epsilon}$-nicotinyl)-D-lysyl, ($N^{\epsilon}$-nicotinylglycyl)-D-lysyl, ($N^{\epsilon}$-nicotinylazaglycyl)-D-lysyl, ($N^{\epsilon}$-furo-2 -ylazaglycyl)-D-lysyl, D-3-(4-(3-amino-1,2,4 -triazol-5yl)phenyl)alanyl, ($N^{\epsilon}$-shikimyl)-D-lysyl, ($N^{\epsilon}$-shikimylglycyl)-D-lysyl, D-citrullyl, D-homocitrullyl, D-arginyl, D-homoarginyl, ($N^g$,$N^g$-diethyl)-D-homoarginyl, and ($N^{\epsilon}$-pyrazinyl)-D-lysyl.

G is an aminoacyl residue selected from the group consisting of L-leucyl, L-isoleucyl, $N^{\alpha}$-methyl-L-leucyl, tert-butyl-L-glycyl, and L-valyl.

H is an aminoacyl residue selected from the group consisting of L-arginyl, L-homoarginyl, ($N^{\epsilon}$-isopropyl)-L-lysyl and ($N^g$,$N^g$-diethyl)-L-homoarginyl.

I is an aminoacyl residue selected from the group consisting of L-prolyl and $N^{\alpha}$-methyl-L-alanyl.

J is an aminoacyl residue selected from the group consisting of glycyl, D-alanyl, and sarcosyl.

In another embodiment of the present invention, there is provided a pharmaceutical formulation comprising a peptide as defined above in an amount therapeutically effective to control the release of LHRH in combination with a pharmaceutically acceptable carrier.

In yet another embodiment, the present invention provides a method for controlling the release of LHRH in a mammal in need of such treatment comprising administering a therapeutically effective amount of a peptide as defined above.

DETAILED DESCRIPTION AND PREFERRED EMBODIMENTS

As used throughout this specification and the amended claims, the term "halide" as used herein refers to bromo (Br), chloro (Cl), fluoro (F) or iodo (I).

The terms "resin" or "peptide resin" as used herein refer to resins of the type commonly used in the art of synthetic peptide preparation. Examples of such resins include, but are not limited to, methyl benzhydrylamine (MBHA) or benzhydrylamine (BHA) or Merrifield resin (i.e. chloromethylated polystyrene).

The term "alkyl" as used herein refers to divalent straight or branched group derived from a saturated hydrocarbon by the removal of a single hydrogen atom. Examples of alkyl include, but are not limited to methyl, ethyl, propyl, isopropyl, butyl, sec-butyl, iso-butyl, tert-butyl, pentyl, hexyl, and the like.

The term "alkylene" refers to a straight or branched divalent group derived from a saturated hydrocarbon by the removal of two hydrogen atoms. Examples of alkylene include $—CH_2—$, $—CH_2CH_2—$, $—CH(CH_3)CH_2—$ and the like.

"Atz" or "Atza" means the substituent group 3-amino-1, 2,4-triazol-5-yl.

The term "nicotinyl" denotes the acyl group derived from nicotinic acid, i.e. pyridine-3-carboxylic acid.

"Picolinyl" refers to the acyl group derived from picolinic acid, i.e. 2-pyridinecarboxylic acid.

"Shikimyl" denotes the acyl residue derived from shikimic acid or 3R-( 3a,4a,5b)-3,4,5-trihydroxy-1-cyclohexene-1-carboxylic acid and "dihydroshikimyl" refers to the fully saturated analog of shikimic acid.

Unless indicated otherwise by a "D" prefix, the stereochemistry of the alpha-carbon atom of the amino acids and aminoacyl residues in peptides described in this specification and the appended claims is the natural or "L" configuration. The Cahn-Ingold-Prelog "R" and "S" designations are used to specify the stereochemistry of chiral centers in certain of the acyl substituents at the N-terminus of the peptides of this invention. The designation "R,S" is meant to indicate a racemic mixture of the two enantiomeric forms. This nomenclature follows that described in R. S. Cahn, C. K. Ingold, and V. Prelog, *Angew. Chem., Int. Ed. Engl.*, 5:385–415 (1966).

For the most part, the names of naturally-occuring and non-naturally-occuring aminoacyl residues used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)," *Biochemistry*, 14(2): 1975). To the extent that the names and abbreviations of amino acids and aminoacyl residues employed in this specification and appended claims differ from those suggestions, they will be made clear to the reader by the following.

Various aminoacyl residues derived from phenylalanine by substitution of the phenyl group are represented by abbreviations such as "D4ClPhe," "D4FPhe," "$D4NO_2Phe$," and "$D4NH_2Phe$," which represent D-3-( 4-chlorophenyl)alanine, D-3-(4-fluorophenyl)alanine, D-3-( 4-nitrophenyl)alanine, and D-3-(4-aminophenyl)alanine, respectively.

"Cit" and "HCit" stand for citrullyl and homocitrullyl (or L-2-amino-( 6-aminocarbonylamino)hexanoic acid), respectively.

"DLys(Nic)" or "D-Lys(N-epsilon nicotinyl)" represents a D-lysine amino acid or aminoacyl residue substituted on the epsilon nitrogen atom of the side chain by a nicotinyl acyl group. Similarly, "DLys(Isonic)," "DLys(Shik)," "DLys(Fur)," and "DLys(THF)" represent D-lysine acylated on the epsilon nitrogen atom by an isonicotinyl, shikimyl, fur-2-oyl, or tetrahydrofur-2-oyl group. "DLys(GlyNic)," "DLys(AzaGlyNic)" and "DLys(AzaGlyShik)" represent aminoacyl residues substituted, respectively, on the epsilon nitrogen atom of a D-lysyl residue by an azaglycyl residue attached directly to the epsilon nitrogen, with a nicotinyl or shikimyl group attached to the N-terminus of the azaglycyl residue. "DLys(Isp)," "DLys(Nisp)" or "D-Lys(N-epsilon isopropyl)" stand for a lysine substituted on the epsilon amino group of the lysine side-chain by an isopropyl group.

"Harg" stands for homoarginyl or L-2-amino-6-guanidinohexanoyl). "HargEt" and "$HargEt_2$" represent L-2-amino-6- $N^g$-ethyl guanidinohexanoic acid and L-2-amino-6-$N^g$, $N^g$-diethylguanidinohexanoic acid, respectively.

"D1Nal" and "D2Nal" represent D-3-(naphth-1-yl)alanine and D- 3-(naphth-2-yl)alanine, respectively. "D3Pal" represents D-3 -(pyrid-3-yl)alanine and "D3Qal" or "D3Qual" stands for D-3-(quinol-3-yl)alanine. "D-(4-Atza-)Phe" or "DAtzPhe" means D-3-(4-(3-amino-1H- 1,2,4-triazol-5-yl)amino)phenyl)alanine and "D-(4-Atzame)Phe" or "D-(AtzMe)Phe" represents D-3-(4-(((3-amino-1H- 1,2, 4'-triazol-5-yl)amino)methyl)phenyl)alanine.

"Sar" and "$SarNH_2$" mean sarcosine or the amide of sarcosine, respectively.

The various abbreviations used for the N-terminal lactam group of peptides of this invention are as follows:

"5LactGly" denotes 2-(N-2'-pyrrolidinonyl)acetyl; "5LactD2 Nal" denotes 2-(N-2'-pyrrolidinonyl)-2-(R)-(2-naphthylmethyl)acetyl; "5LactD3Qal" denotes 2-(N-2'-pyrrolidinonyl)-2-(R)-(3-quinolinylmethyl)acetyl; "5LactD4ClPhe" denotes 2-(N-2'-pyrrolidinonyl)-2-(R)-(4-chlorophenylmethyl)acetyl; "5LactDPhe" denotes 2-(N-2'-pyrrolidinonyl)-2-(R)-benzylacetyl; "5LactD1Nal" denotes 2 (N-2'- pyrrolidinonyl)-2-(R)-(1-naphthylmethyl)acetyl.

"6LactGly" denotes 2-(N-2'-piperidinonyl)acetyl; "6LactD2Nal" denotes 2-(N-2'-piperidinonyl)-2-(R)-(2-naphthylmethyl)acetyl; "6LactD3Qal" denotes 2-(N- 2'-piperidinonyl)-2-(R)-(3-quinolinylmethyl)acetyl; "6LactD4ClPhe" denotes 2-(N-2'-piperidinonyl)-2-(R)-(4-chlorophenylmethyl)acetyl; "6LactDPhe" denotes 2-(N-2'-piperidinonyl)-2-(R)-benzylacetyl; and "6LactD1Nal" denotes 2-(N-2'-piperidinonyl)-2-(R)-(1-naphthylmethyl)acetyl.

"7LactGly" denotes 2-(N-ϵ-caprolactamyl)acetyl; "7LactD2Nal" denotes 2-(N-ϵ-caprolactamyl)-2-(R)-(2-naphthylmethyl)acetyl; "7LactD3Qal" denotes 2-(N-ϵ-caprolactamyl)-2-(R)-(3-quinolinylmethyl)acetyl; "7LactD4ClPhe" denotes (N-ϵ-caprolactamyl)-2-(R)-(4-chlorophenylmethyl)acetyl; "7LactDPhe" denotes (N-ϵ-caprolactamyl)-2-(R)-benzylacetyl; and "7LactD1Nal" denotes (N-ϵ-caprolactamyl)-2-(R)-(1-naphthylmethyl)acetyl.

By the term "pharmaceutically acceptable salt" is meant salts recognized in the pharmaceutical formulation arts as non-toxic and sutable for use in formulations intended for use in human and animal treatment. Suitable acids and bases useful for this purpose are listed, for example, in the review article, "Pharmaceutical Salts" by S. N. Berge, et al., *J. Pharm. Sci.*, 66: 1–19 (1977).

Preferred compounds of the present invention have the structure:

$$X—B—C—D—E—F—G—H—I—J—NH_2$$

wherein X is selected from the group consisting of 2-(N-2'-pyrrolidinonyl)-2-(R)-( 2-naphythylmethyl)acetyl, 2-(N-2'-pyrrolidinonyl)- 2-(R)-(3-quinolinylmethyl)acetyl, 2-(N-2'-piperidinonyl)-2-(R)-(2-naphythylmethyl)acetyl, 2-(N-2'-piperidinonyl)-2-(R)-(3-quinolinylmethyl)acetyl, 2-(N-ϵ-caprolactamyl)-2-(R)-(2-naphythylmethyl)acetyl, and 2-(N-ϵ-caprolactamyl)-2-(R)-(3-quinolinylmethyl)acetyl.

B is an aminoacyl residue selected from the group consisting of D-phenylalanyl, D-3-(4-chlorophenyl)alanyl, and D-3-(4-fluorophenyl)alanyl.

C is an aminoacyl residue selected from the group consisting of D-3-(pyrid-3-yl)alanyl, D-3-(naphth-1-yl)alanyl, and D-tryptophyl.

D is an aminoacyl residue selected from the goup consisting of L-seryl, N-a-methyl-L-seryl, and L-threonyl.

E is an aminoacyl residue selected from the group consisting of L-tyrosyl, L-3-(4-(3-amino-1H-12,2,4-triazol-5-yl)amino)phenyl)alanine, Nα-methyl-L-tyrosyl, and Nα-methyl-L-3-(4-(3-amino-1H-1,2,4-triazol- 5-yl)amino)phenyl)alanine.

F is an aminoacyl residue selected from the group consisting of D-citrullyl, D-homocitrullyl, D-lysyl(N-epsilon nicotinyl), D-lysyl(N-epsilon glycyl nicotinyl), D-lysyl(N-epsilon azaglycyl nicotinyl), D-lysyl(N-epsilon shikimyl), D-lysyl(N-epsilon glycyl shikimyl), D-lysyl(N-epsilon fur-2-oyl), D-lysyl(N-epsilon glycyl fur-2-oyl), D-lysyl(N-epsilon azaglycyl fur-2-oyl), and D-3-(4-(3-amino-1H- 1,2,4-triazol-5-yl)amino)phenyl)alanine.

G is an aminoacyl residue selected from the group consisting of L-leucyl, L-isoleucyl, Nα-methyl-L-leucyl, tert-butyl-L-glycyl, and L-valyl.

H is an aminoacyl residue selected from the group consisting of L-arginyl, L-homoarginyl, L-lysyl(N-epsilon isopropyl), and L-2-amino-6-$N^g$,$N^g$-diethylguanidinohexanoic acid.

I is an aminoacyl residue selected from the group consisting of L-prolyl, and $N^{\alpha}$-methyl-L-alanyl.

J is an aminoacyl residue selected from the group consisting of glycyl, D-alanyl, and sarcosyl.

In a particularly preferred embodiment, compounds of this invention have the structure:

$$X\text{—}B\text{—}D3Pal\text{—}Ser\text{—}E\text{—}F\text{—}G\text{—}H\text{—}Pro\text{—}Ala\text{—}NH_2$$

is wherein X is selected from the group consisting of 2-(N-2'-pyrrolidinonyl)-2-(R)-( 2-naphythylmethyl)acetyl, and 2-(N-2'-piperidinonyl)-2-(R)-( 2-naphythylmethyl)acetyl.

B is an aminoacyl residue selected from the group consisting of D-3-( 4-chlorophenyl)alanyl, and D-3-(4-fluorophenyl)alanyl.

E is an aminoacyl residue selected from the group consisting of L-tyrosyl, L-3-(4-(3-amino-1H-12,2,4-triazol-5-yl)amino)phenyl)alanine, Nα-methyl-L-tyrosyl, and Nα-methyl-L-3-(4-(3-amino-1H-1,2,4-triazol- 5-yl)amino)phenyl)alanine.

F is an aminoacyl residue selected from the group consisting of D-citrullyl, D-homocitrullyl, D-lysyl(N-epsilon nicotinyl), D-lysyl(N-epsilon glycyl nicotinyl), D-lysyl(N-epsilon anaglycyl nicotinyl), D-lysyl(N-epsilon shikimyl), D-lysyl(N-epsilon glycyl shikimyl), D-lysyl(N-epsilon fur-2-oyl), D-lysyl(N-epsilon glycyl fur-2-oyl), D-lysyl(N-epsilon azaglycyl fur-2-oyl), and D-3-(4-(3-amino-1H-1,2,4-triazol-5-yl)amino)phenyl)alanine.

G is an aminoacyl residue selected from the group consisting of L-leucyl, and Nα-methyl-L-leucyl.

H is an aminoacyl residue selected from the group consisting of L-arginyl, L-homoarginyl, L-lysyl(N-epsilon isopropyl), L-2-amino-6-Ng,Ng-diethylguanidinohexanoic acid.

Peptide LHRH antagonists falling within the scope of the present invention include, for example:

5LactD2Nal$^1$-D4ClPhe$^2$-D3Pal$^3$ -Ser$^4$-NMeTyr$^5$-DCit$^6$ -Leu$^7$-Arg$^8$-Pro$^9$-DAla$^{10}$NH$_2$;

5LactD2Nal$^1$-D4ClPhe$^2$-D3Pal$^3$ -Ser$^4$-NMeTyr$^5$-DLys(N-epsilon-Shik)$^6$ -Leu$^7$-Arg$^8$-Pro$^9$-DAla$^{10}$NH$_2$;

5LactD2Nal$^1$-D4ClPhe$^2$-D3Pal$^3$ -Ser$^4$-NMeTyr$^5$-DLys(N-epsilon-Gly-Shik)$^6$ -Leu$^7$-Arg$^8$-Pro$^9$-DAla$^{10}$NH$_2$;

5LactD2Nal$^1$-D4ClPhe$^2$-D3Pal$^3$ -Ser$^4$-NMeTyr$^5$-DLys(N-epsilon-Shik)$^6$ -Leu$^7$-Harg$^8$-Pro$^9$-DAla$^{10}$NH$_2$;

5LactD2Nal$^1$-D4ClPhe$^2$-D3Pal$^3$ -Ser$^4$- NMeTyr$^5$-DLys(N-epsilon-Gly-Shik)$^6$-Leu$^7$-Harg$^8$-Pro$^9$-DAla$^{10}$NH$_2$;

5LactD2Nal$^1$-D4ClPhe$^2$-D3Pal$^3$ -Ser$^4$-Tyr$^5$-DCit$^6$ -Leu$^7$-Arg$^8$-Pro$^9$-DAla$^{10}$NH$_2$;

5LactD2Nal$^1$-D4ClPhe$^2$-D3Pal$^3$ -Ser$^4$-NMeTyr$^5$-DLys(N-epsilon-Nic)$^6$ -Leu$^7$-Lys(N-epsilon-Isopropyl)$^8$-Pro$^9$-DAla$^{10}$NH$_2$;

6LactD2Nal$^1$-D4ClPhe$^2$-D3Pal$^3$ -Ser$^4$-NMeTyr$^5$-DLys(N-epsilon-Shik)$^6$ -Leu$^7$-Arg$^8$-Pro$^9$-DAla$^{10}$NH$_2$;

6LactD2Nal$^1$-D4ClPhe$^2$-D3Pal$^3$ -Ser$^4$-NMeTyr$^5$-DLys(N-epsilon-Gly-Shik)$^6$ -Leu$^7$-Arg$^8$-Pro$^9$-DAla$^{10}$NH$_2$;

6LactD2Nal$^1$-D4ClPhe$^2$-D3Pal$^3$ -Ser$^4$-NMeTyr$^5$-DLys(N-epsilon-Shik)$^6$ -Leu$^7$-Harg$^8$-Pro$^9$-DAla$^{10}$NH$_2$;

6LactD2Nal$^1$-D4ClPhe$^2$-D3Pal$^3$ -Ser$^4$-NMeTyr$^5$-DLys(N-epsilon-Gly-Shik)$^6$ -Leu$^7$-Harg$^8$-Pro$^9$-DAla$^{10}$NH$_2$;

5LactD2Nal$^1$-D4ClPhe$^2$-D3Pal$^3$ -Ser$^4$-Tyr$^5$-DHcit$^6$ -Leu$^7$-Lys(isp)$^8$-Pro$^9$-DAla$^{10}$NH$_2$;

6LactD2Nal$^1$-D4ClPhe$^2$-D3Pal$^3$ -Ser$^4$-NMeTyr$^5$-DLys(N-epsilon-Nic)$^6$ -Leu$^7$-Lys(N-epsilon-Isopropyl)$^8$-Pro$^9$-DAla$^{10}$NH$_2$;

5LactGly$^1$-D4ClPhe$^2$-D1Nal$^3$ -Ser$^4$-NMeTyr$^5$-DCit$^6$ -Leu$^7$-Harg$^8$-Pro$^9$-DAla$^{10}$NH$_2$;

5LactGly$^1$-D4ClPhe$^2$-D3Pal$^3$ -Ser$^4$-NMeTyr$^5$-DLys-(Nic)$^6$ -Leu$^7$-Lys(N-epsilon-Isopropyl)$^8$-Pro$^9$-DAla$^{10}$NH$_2$;

5LactD4Qal$^1$-D4ClPhe$^2$-D3Pal$^3$ -Ser$^4$-NMeTyr$^5$-DLys-(Nic)$^6$ -Leu$^7$-Lys(N-epsilon-Isopropyl)$^8$-Pro$^9$-DAla$^{10}$NH$_2$;

5LactD4ClPhe$^1$-D4ClPhe$^2$-D3Pal$^3$ -Ser$^4$-NMeTyr$^5$-DLys(Nic)$^6$-Leu$^7$-Lys(N-epsilon-Isopropyl)$^8$-Pro$^9$-DAla$^{10}$NH$_2$;

5LactDPhe$^1$-D4ClPhe$^2$-D3Pal$^3$ -Ser$^4$-NMeTyr$^5$-DLys-(Nic)$^6$ -Leu$^7$-Lys(N-epsilon-Isopropyl)$^8$-Pro$^9$-DAla$^{10}$NH$_2$;

5LactD1Nal$^1$-D4ClPhe$^2$-D3Pal$^3$ -Ser$^4$-NMeTyr$^5$-DLys-(Nic)$^6$ -Leu$^7$-Lys(N-epsilon-Isopropyl)$^8$-Pro$^9$-DAla$^{10}$NH$_2$;

6LactGly$^1$D4ClPhe$^2$-D3Pal$^3$ -Ser$^4$-NMeTyr$^5$-DLys(Nic)$^6$ -Leu$^7$-Lys(N-epsilon-Isopropyl)$^8$-Pro$^9$-DAla$^{10}$NH$_2$;

6LactD3Qal$^1$-D4ClPhe$^2$-D3Pal$^3$ -Ser$^4$-NMeTyr$^5$-DLys-(Nic)$^6$ -Leu$^7$-Lys(N-epsilon-Isopropyl)$^8$-Pro$^9$-DAla$^{10}$NH$_2$;

6LactD4ClPhe$^1$-D4ClPhe$^2$-D3Pal$^3$ -Ser$^4$-NMeTyr$^5$-DLys-(Nic)$^6$ -Leu$^7$-Lys(N-epsilon-Isopropyl)$^8$-Pro$^9$-DAla$^{10}$NH$_2$;

6LactDPhe$^1$-D4ClPhe$^2$-D3Pal$^3$ -Ser$^4$-NMeTyr$^5$-DLys(Nic)$^6$ -Leu$^7$-Lys(N-epsilon-Isopropyl)$^8$-Pro$^9$-DAla$^{10}$NH$_2$;

6LactD1Nal$^1$-D4ClPhe$^2$-D3Pal$^3$ -Ser$^4$-NMeTyr$^5$-DLys-(Nic)$^6$ -Leu$^7$-Lys(N-epsilon-Isopropyl)$^8$-Pro$^9$-DAla$^{10}$NH$_2$;

7LactGly$^1$-D4ClPhe$^2$-D3Pal$^3$ -Ser$^4$-NMeTyr$^5$-DLys(Nic)$^6$ -Leu$^7$-Lys(N-epsilon-Isopropyl)$^8$-Pro$^9$-DAla$^{10}$NH$_2$;

7LacytD2Nal$^1$-D4ClPhe$^2$-D3Pal$^3$ -Ser$^4$-NMeTyr$^5$-DLys-(Nic)$^6$ -Leu$^7$-Lys(N-epsilon-Isopropyl)$^8$-Pro$^9$-DAla$^{10}$NH$_2$;

7LactD3Qal$^1$-D4ClPhe$^2$-D3Pal$^3$ -Ser$^4$-NMeTyr$^5$-DLys-(Nic)$^6$ -Leu$^7$-Lys(N-epsilon-Isopropyl)$^8$-Pro$^9$-DAla$^{10}$NH$_2$;

7LactD4ClPhe$^1$-D4ClPhe$^2$-D3Pal$^3$ -Ser$^4$-NMeTyr$^5$-DLys-(Nic)$^6$ -Leu$^7$-Lys(N-epsilon-Isopropyl)$^8$-Pro$^9$-DAla$^{10}$NH$_2$;

7LactDPhe$^1$-D4ClPhe$^2$-D3Pal$^3$ -Ser$^4$-NMeTyr$^5$-DLys-(Nic)$^6$ -Leu$^7$-Lys(N-epsilon-Isopropyl)$^8$-Prop$^9$-DAla$^{10}$NH$_2$;

7LactD1Nal$^1$-D4ClPhe$^2$-D3Pal$^3$ -Ser$^4$-NMeTyr$^5$-DLys-(Nic)$^6$ -Leu$^7$-Lys(N-epsilon-Isopropyl)$^8$-Pro$^9$-DAla$^{10}$NH$_2$;

5LactD2Nal$^1$-DPhe$^2$-D3Pal$^3$ -Ser$^4$-NMeTyr$^5$-DLys(Nic)$^6$ -Leu$^7$-Lys(N-epsilon-isopropyl)$^8$-Pro$^9$-DAla$^{10}$NH$_2$;

5LactD2Nal$^1$-D2Nal$^2$-D3Pal$^3$ -Ser$^4$-NMeTyr$^5$-DLys(Nic)$^6$ -Leu$^7$-Lys(N-epsilon-isopropyl)$^8$-Pro$^9$-DAla$^{10}$NH$_2$;

5LactD2Nal$^1$-D4FPhe$^2$-D3Pal$^3$ -Ser$^4$-NMeTyr$^5$-DLys(Nic)$^6$ -Leu$^7$-Lys(N-epsilon-Isopropyl)$^8$-Pro$^9$-DAla$^{10}$NH$_2$;

5LactD2Nal$^1$-D4ClPhe$^2$-Gly$^3$ -Ser$^4$-NMeTyr$^5$-DLys(Nic)$^6$ -Leu$^7$-Lys(N-epsilon-Isopropyl)$^8$-Pro$^9$-DAla$^{10}$NH$_2$;

5LactD2Nal$^1$-D4ClPhe$^2$-D1Nal$^3$ -Ser$^4$-NMeTyr$^5$-DLys-(Nic)$^6$ -Leu$^7$-Lys(N-epsilon-Isopropyl)$^8$-Pro$^9$-DAla$^{10}$NH$_2$;

5LactD2Nal$^1$-D4ClPhe$^2$-DAla$^3$ -Ser$^4$-NMeTyr$^5$-DLys-(Nic)$^6$ -Leu$^7$-Lys(N-epsilon-Isopropyl)$^8$-Pro$^9$-DAla$^{10}$NH$_2$;

5LactD2Nal$^1$-D4ClPhe$^2$-DTrp3 -Ser$^4$-NMeTyr$^5$-DLys-(Nic)$^6$ -Leu$_7$-Lys(N-epsilon-Isopropyl)$^8$-Pro$^9$-DAla$^{10}$NH$_2$ 5LactD2Nal$^1$-D4ClPhe$^2$-D3Bal$^3$ -Ser$^4$-NMeTyr$^5$-DLys-(Nic)$^6$ -Leu$_7$-Lys(N-epsilon-Isopropyl)$^8$-Pro$^9$-DAla$^{10}$NH$_2$ 5LactD2Nal$^1$-D4ClPhe$^2$-D3Pal$^3$ -NMeSer$^4$-NMeTyr$^5$-DLys(Nic)$^6$ -Leu$^7$-Lys(N-epsilon-Isopropyl)$^8$-Pro$^9$-DAla$^{10}$NH$_2$ 5LactD2Nal$^1$-D4ClPhe$^2$-D3Pal$^3$ -Gly$^4$-NMeTyr$^5$-DLys-(Nic)$^6$-Leu$^7$-Lys(N-epsilon-Isopropyl)$^8$-Pro$^9$-DAla$^{10}$NH$_2$ 5LactD2Nal$^1$-D4ClPhe$^2$-D3Pal$^3$ -Thr$_4$-NMeTyr$^5$-DLys-(Nic)$^6$-Leu$^7$-Lys(N-epsilon-Isopropyl)$^8$-Pro$^9$-DAla$^{10}$NH$_2$ 5LactD2Nal$^1$-D4ClPhe$^2$-D3Pal$^3$ -Ser$_4$-Tyr$^5$-DLys(Nic)$^6$-Leu$^7$-Lys(N-epsilon-Isopropyl)$^8$-Pro$^9$-DAla$^{10}$NH$_2$ 5LactD2Nal$^1$-D4ClPhe$^2$-D3Pal$^3$ -Ser$_4$-Lys(Nic)$^5$-DLys-(Nic)$^6$-Leu$^7$-Lys(N-epsilon-Isopropyl)$^8$-Pro$^9$-DAla$^{10}$NH$_2$ 5LactD2Nal$^1$-D4ClPhe$^2$-D3Pal$^3$ -Ser$_4$-Lys(Pic)$^5$-DLys-(Nic)$^6$-Leu$^7$-Lys(N-epsilon-Isopropyl)$^8$-Pro$^9$-DAla$^{10}$NH$_2$ 5LactD2Nal$^1$-D4ClPhe$^2$-D3Pal$^3$ -Ser$_4$-NMePhe$^5$-DLys-(Nic)$^6$-Leu$^7$-Lys(N-epsilon-Isopropyl)$^8$-Pro$^9$-DAla$^{10}$NH$_2$ 5LactD2Nal$^1$-D4ClPhe$^2$-D3Pal$^3$ -Ser$_4$-Phe(Atz)$^5$-DLys-(Nic)$^6$-Leu$^7$-Lys(N-epsilon-Isopropyl)$^8$-Pro$^9$-DAla$^{10}$NH$_2$ 5LactD2Nal$^1$-D4ClPhe$^2$-D3Pal$^3$ -Ser$_4$-NMePhe(Atz)$^5$-DLys(Nic)$_6$-Leu$^7$-Lys(N-epsilon-Isopropyl)$^8$-Pro$^9$-DAla$^{10}$NH$_2$ 5LactD2Nal$^1$-D4ClPhe$^2$-D3Pal$^3$ -Ser$_4$-NMeTyr$^5$-DCit$^6$-Leu$^7$-Lys(N-epsilon-Isopropyl)$^8$-Pro$^9$-DAla$^{10}$NH$_2$ 5LactD2Nal$^1$-D4ClPhe$^2$-D3Pal$^3$ -Ser$_4$-NMeTyr$^5$-DHcit$^6$-Leu$^7$-Lys(N-epsilon-Isopropyl)$^8$-Pro$^9$-DAla$^{10}$NH$_2$ 5LactD2Nal$^1$-D4ClPhe$^2$-D3Pal$^3$ -Ser$_4$-NMeTyr$^5$-DArg$^6$-Leu$^7$-Lys(N-epsilon-Isopropyl)$^8$-Pro$^9$-DAla$^{10}$NH$_2$ 5LactD2Nal$^1$-D4ClPhe$^2$-D3Pal$^3$ -Ser$_4$-NMeTyr$^5$-DHarg$^6$-Leu$^7$-Lys(N-epsilon-Isopropyl)$^8$-Pro$^9$-DAla$^{10}$NH$_2$ 5LactD2Nal$^1$-D4ClPhe$^2$-D3Pal$^3$ -Ser$_4$-NMeTyr$^5$-DHar-g(Et$_2$)$^6$-Leu$^7$-Lys(N-epsilon-Isopropyl)$^8$-Pro$^9$-DAla$^{10}$NH$_2$ 5LactD2Nal$^1$-D4ClPhe$^2$-D3Pal$^3$ -Ser$_4$-NMeTyr$^5$-DLys(Shik)$_6$-Leu$^7$-Lys(N-epsilon-Isopropyl)$^8$-Pro$^9$-DAla$^{10}$NH$_2$ 5LactD2Nal$^1$-D4ClPhe$^2$-D3Pal$^3$ -Ser$_4$-NMeTyr$^5$-DLys(Pyz)$_6$-Leu$^7$-Lys(N-epsilon-Isopropyl)$^8$-Pro$^9$-DAla$^{10}$NH$_2$ 5LactD2Nal$^1$-D4ClPhe$^2$-D3Pal$^3$ -Ser$^4$-NMeTyr$^5$-DLys-(GlyShik)$^6$ -Leu$^7$-Lys(N-epsilon-Isopropyl)$^8$-Pro$^9$-DAla$^{10}$NH$_2$;

5LactD2Nal$^1$-D4ClPhe$^2$-D3Pal$^3$ -Ser$^4$-NMeTyr$^5$-DLys(G-lyNic)$^6$ -Leu$^7$-Lys(N-epsilon-Isopropyl)$^8$-Pro$^9$-DAla$^{10}$NH$_2$;

5LactD2Nal$^1$-D4ClPhe$^2$-D3Pal$^3$ -Ser$^4$-NMeTyr$^5$-DLys(AzaglyNic)$^6$ -Leu$^7$-Lys(N-epsilon-Isopropyl)$^8$-Pro$^9$-DAla$^{10}$NH$_2$;

5LactD2Nal$^1$-D4ClPhe$^2$-D3Pal$^3$ -Ser$^4$-NMeTyr$^5$-DLys(Azagly-2-Fur)$^6$ -Leu$^7$-Lys(N-epsilon-Isopropyl)$^8$-Pro$^9$-DAla$^{10}$NH$_2$;

5LactD2Nal$^1$-D4ClPhe$^2$-D3Pal$^3$ -Ser$^4$-NMeTyr$^5$-DLy-s(Atz)$^6$ -Leu$^7$-Lys(N-epsilon-Isopropyl)$^8$-Pro$^9$-DAla$^{10}$NH$_2$;

5LactD2Nal$^1$-D4ClPhe$^2$-D3Pal$^3$ -Ser$^4$-NMeTyr$^5$-DLys-(Nic)$^6$ -Ile$^7$-Lys(N-epsilon-Isopropyl)$^8$-Pro$^9$-DAla$^{10}$NH$_2$;

5LactD2Nal$^1$-D4ClPhe$^2$-D3Pal$^3$ -Ser$^4$-NMeTyr$^5$-DLys-(Nic)$^6$ -NMeLeu$^7$-Lys(N-epsilon-Isopropyl)$^8$-Pro$^9$-DAla$^{10}$NH$_2$;

5LactD2Nal$^1$-D4ClPhe$^2$-D3Pal$^3$ -Ser$^4$-NMeTyr$^5$-DLys-(Nic)$^6$ -t-BuGly$^7$-Lys(N-epsilon-Isopropyl)$^8$-Pro$^9$-DAla$^{10}$NH$_2$;

5LactD2Nal$^1$-D4ClPhe$^2$-D3Pal$^3$ -Ser$^4$-NMeTyr$^5$-DLys-(Nic)$^6$ -Val$^7$-Lys(N-epsilon-Isopropyl)$^8$-Pro$^9$-DAla$^{10}$NH$_2$;

5LactD2Nal$^1$-D4ClPhe$^2$-D3Pal$^3$ -Ser$^4$-NMeTyr$^5$-DLys-(Nic)$^6$ -Leu$^7$-Arg$^8$-Pro$^9$-DAla$^{10}$NH$_2$;

5LactD2Nal$^1$-D4ClPhe$^2$-D3Pal$^3$ -Ser$^4$-NMeTyr$^5$-DLys-(Nic)$^6$ -Leu$^7$-Harg$^8$-Pro$^9$-DAla$^{10}$NH$_2$;

5LactD2Nal$^1$-D4ClPhe$^2$-D3Pal$^3$ -Ser$^4$-NMeTyr$^5$-DLys-(Nic)$^6$ -Leu$^7$-Harg(Et$_2$)$^8$-Pro$^9$-DAla$^{10}$NH$_2$;

5LactD2Nal$^1$-D4ClPhe$^2$-D3Pal$^3$ -Ser$^4$-NMeTyr$^5$-DLys-(Nic)$^6$ -Leu$^7$-Lys(N-epsilon-1-hydroxy-isopropyl)$^8$-Pro$^9$-DAla$^{10}$NH$_2$;

5LactD2Nal$^1$-D4ClPhe$^2$-D3Pal$^3$ -Ser$^4$-NMeTyr$^5$-DLys-(Nic)$^6$ -Leu$^7$-Lys(Isp)$^8$-NMeAla$^9$-DAla$^{10}$NH$_2$;

5LactD2Nal$^1$-D4ClPhe$^2$-D3Pal$^3$ -Ser$^4$-NMeTyr$^5$-DLys-(Nic)$^6$ -Leu$^7$-Lys(Isp)$^8$-Pro$^9$-Gly$^{10}$NH$_2$;

5LactD2Nal$^1$-D4ClPhe$^2$-D3Pal$^3$ -Ser$^4$-NMeTyr$^5$-DLys-(Nic)$^6$ -Leu$^7$-Lys(Isp)$^8$-Pro$^9$-Sar$^{10}$NH$_2$;

5LactD2Nal$^1$-D4ClPhe$^2$-D3Pal$^3$ -Ser$^4$-NMeTyr$^5$-DLys-(Nic)$^6$ -Leu$^7$-Lys(Isp)$^8$-Pro$^9$-DSer$^{10}$NH$_2$;

5LactGly$^2$-D4ClPhe$^2$-D3Pal$^3$ -Ser$^4$-Tyr$^5$-DCit$^6$ -Leu$^7$-Arg$^8$-Pro$^9$-DAla$^{10}$NH$_2$;

5LactD3Qal$^1$-D4ClPhe$^2$-D3Pal$^3$ -Ser$^4$-Tyr$^5$-DCit$^6$ -Leu$^7$-Arg$^8$-Pro$^9$-DAla$^{10}$NH$_2$;

5LactD4ClPhe$^1$-D4ClPhe$^2$-D3Pal$^3$ -Ser$^4$-Tyr$^5$-DCit$^6$ -Leu$^7$-Arg$^8$-Pro$^9$-DAla$^{10}$NH$_2$;

5LactDPhe$^1$-D4ClPhe$^2$-D3Pal$^3$ -Ser$^4$-Tyr$^5$-DCit$^6$ -Leu$^7$-Arg$^8$-Pro$^9$-DAla$^{10}$NH$_2$;

5LactD1Nal$^1$-D4ClPhe$^2$-D3Pal$^3$ -Ser$^4$-Tyr$^5$-DCit$^6$ -Leu$^7$-Arg$^8$-Pro$^9$-DAla$^{10}$NH$_2$;

6LactGly$^1$-D4ClPhe$^2$-D3Pal$^3$ -Ser$^4$-Tyr$^5$-DCit$^6$ -Leu$^7$-Arg$^8$-Pro$^9$-DAla$^{10}$NH$_2$;

6LactD3Qal$^1$-D4ClPhe$^2$-D3Pal$^3$ -Ser$^4$-Tyr$^5$-DCit$^6$ -Leu$^7$-Arg$^8$-Pro$^9$-DAla$^{10}$NH$_2$;

6LactD4ClPhe$^1$-D4ClPhe$^2$-D3Pal$^3$ -Ser$^4$-Tyr$^5$-DCit$^6$ -Leu$^7$-Arg$^8$-Pro$^9$-DAla$^{10}$NH$_2$;

6LactDPhe$^1$-D4ClPhe$^2$-D3Pal$^3$ -Ser$^4$-Tyr$^5$-DCit$^6$ -Leu$^7$-Arg$^8$-Pro$^9$-DAla$^{10}$NH$_2$;

6LactD1Nal$^1$-D4ClPhe$^2$-D3Pal$^3$ -Ser$^4$-Tyr$^5$-DCit$^6$ -Leu$^7$-Arg$^8$-Pro$^9$-DAla$^{10}$NH$_2$;

7LactDGly$^1$-D4ClPhe$^2$-D3Pal$^3$ -Ser$^4$-Tyr$^5$-DCit$^6$ -Leu$^7$-Arg$^8$-Pro$^9$-DAla$^{10}$NH$_2$;

7LactD2Nal$^1$-D4ClPhe$^2$-D3Pal$^3$ -Ser$^4$-Tyr$^5$-DCit$^6$ -Leu$^7$-Arg$^8$-Pro$^9$-DAla$^{10}$NH$_2$;

7LactD3Qal$^1$-D4ClPhe$^2$-D3Pal$^3$ -Ser$^4$-Tyr$^5$-DCit$^6$ -Leu$^7$-Arg$^8$-Pro$^9$-DAla$^{10}$NH$_2$;

7LactD4ClPhe$^1$-D4ClPhe$^2$-D3Pal$^3$ -Ser$^4$-Tyr$^5$-DCit$^6$ -Leu$^7$-Arg$^8$-Pro$^9$-DAla$^{10}$NH$_2$;

7LactDPhe$^1$-D4ClPhe$^2$-D3Pal$^3$ -Ser$^4$-Tyr$^5$-DCit$^6$ -Leu$^7$-Arg$^8$-Pro$^9$-DAla$^{10}$NH$_2$;

7LactD1Nal$^1$-D4ClPhe$^2$-D3Pal$^3$ -Ser$^4$-Tyr$^5$-DCit$^6$ -Leu$^7$-Arg$^8$-Pro$^9$-DAla$^{10}$NH$_2$;

6LactD2Nal$^1$-D4ClPhe$^2$-D3Pal$^3$ -Ser$^4$-Tyr$^5$-DCit$^6$ -Leu$^7$-Arg$^8$-Pro$^9$-DAla$^{10}$NH$_2$;

5LactGly$^1$-D4ClPhe$^2$-D3Pal$^3$ -Ser$^4$-Tyr$^5$-DHcit$^6$ -Leu$^7$-Ly-s(Isp)$^8$-Pro$^9$-DAla$^{10}$NH$_2$;

5LactD3Qal$^1$-D4ClPhe$^2$-D3Pal$^3$ -Ser$^4$-Tyr$^5$-DHcit$^6$ -Leu$^7$-Lys(Isp)$^8$-Pro$^9$-DAla$^{10}$NH$_2$;

5LactD4ClPhe$^1$-D4ClPhe$^2$-D3Pal$^3$ -Ser$^4$-Tyr$^5$-DHcit$^6$ -Leu$^7$-Lys(Isp)$^8$-Pro$^9$-DAla$^{10}$NH$_2$;

5LactDPhe$^1$-D4ClPhe$^2$-D3Pal$^3$ -Ser$^4$-Tyr$^5$-DHcit$^6$ -Leu$^7$-Lys(Isp)$^8$-Pro$^9$-DAla$^{10}$NH$_2$;

5LactD1Nal$^{1}$-D4ClPhe$^{2}$-D3Pal$^{3}$ -Ser$^{4}$-Tyr$^{5}$-DHcit$^{6}$ -Leu$^{7}$-Lys(Isp)$^{8}$-Pro$^{9}$-DAla$^{10}$NH$_{2}$;

6LactGly$^{1}$-D4ClPhe$^{2}$-D3Pal$^{3}$ -Ser$^{4}$-Tyr$^{5}$-DHcit$^{6}$ -Leu$^{7}$-Lys(Isp)$^{8}$-Pro$^{9}$-DAla$^{10}$NH$_{2}$;

6LactD3Qal$^{1}$-D4ClPhe$^{2}$-D3Pal$^{3}$ -Ser$^{4}$-Tyr$^{5}$-DHcit$^{6}$ -Leu$^{7}$-Lys(Isp)$^{8}$-Pro$^{9}$-DAla$^{10}$NH$_{2}$;

6LactD4ClPhe$^{1}$-D4ClPhe$^{2}$-D3Pal$^{3}$ -Ser$^{4}$-Tyr$^{5}$-DHcit$^{6}$ -Leu$^{7}$-Lys(Isp)$^{8}$-Pro$^{9}$-DAla$^{10}$NH$_{2}$;

6LactDPhe$^{1}$-D4ClPhe$^{2}$-D3Pal$^{3}$ -Ser$^{4}$-Tyr$^{5}$-DHcit$^{6}$ -Leu$^{7}$-Lys(Isp)$^{8}$-Pro$^{9}$-DAla$^{10}$NH$_{2}$;

6LactD1Nal$^{1}$-D4ClPhe$^{2}$-D3Pal$^{3}$ -Ser$^{4}$-Tyr$^{5}$-DHcit$^{6}$ -Leu$^{7}$-Lys(Isp)$^{8}$-Pro$^{9}$-DAla$^{10}$NH$_{2}$;

7LactGly$^{1}$-D4ClPhe$^{2}$-D3Pal$^{3}$ -Ser$^{4}$-Tyr$^{5}$-DHcit$^{6}$ -Leu$^{7}$-Lys(Isp)$^{8}$-Pro$^{9}$-DAla$^{10}$NH$_{2}$;

7LactD2Nal$^{1}$-D4ClPhe$^{2}$-D3Pal$^{3}$ -Ser$^{4}$-Tyr$^{5}$-DHcit$^{6}$ -Leu$^{7}$-Lys(Isp)$^{8}$-Pro$^{9}$-DAla$^{10}$NH$_{2}$;

7LactD3Qal$^{1}$-D4ClPhe$^{2}$-D3Pal$^{3}$ -Ser$^{4}$-Tyr$^{5}$-DHcit$^{6}$ -Leu$^{7}$-Lys(Isp)$^{8}$-Pro$^{9}$-DAla$^{10}$NH$_{2}$;

7LactD4ClPhe$^{1}$-D4ClPhe$^{2}$-D3Pal$^{3}$ -Ser$^{4}$-Tyr$^{5}$-DHcit$^{6}$ -Leu$^{7}$-Lys(Isp)$^{8}$-Pro$^{9}$-DAla$^{10}$NH$_{2}$;

7LactDPhe$^{1}$-D4ClPhe$^{2}$-D3Pal$^{3}$ -Ser$^{4}$-Tyr$^{5}$-DHcit$^{6}$ -Leu$^{7}$-Lys(Isp)$^{8}$-Pro$^{9}$-DAla$^{10}$NH$_{2}$;

7LactD1Nal$^{1}$-D4ClPhe$^{2}$-D3Pal$^{3}$ -Ser$^{4}$-Tyr$^{5}$-DHcit$^{6}$ -Leu$^{7}$-Lys(Isp)$^{8}$-Pro$^{9}$-DAla$^{10}$NH$_{2}$;

6LactD2Nal$^{1}$-D4ClPhe$^{2}$-D3Pal$^{3}$ -Ser$^{4}$-Tyr$^{5}$-DHcit$^{6}$ -Leu$^{7}$-Lys(Isp)$^{8}$-Pro$^{9}$-DAla$^{10}$NH$_{2}$;

5LactD2Nal$^{1}$-D4ClPhe$^{2}$-D3Pal$^{3}$ -Ser$^{4}$-Phe(Atz)$^{5}$-DPhe(Atz)$^{6}$ -Leu$^{7}$-Lys(N-epsilon-Isopropyl)$^{8}$-Pro$^{9}$-DAla$^{10}$NH$_{2}$;

5LactGly$^{1}$-D4ClPhe$^{2}$-D3Pal$^{3}$ -Ser$^{4}$-Phe(Atz)$^{5}$-DPhe(Atz)$^{6}$ -Leu$^{7}$-Lys(Isp)$^{8}$-Pro$^{9}$-DAla$^{10}$NH$_{2}$;

5LactD3Qal$^{1}$-D4ClPhe$^{2}$-D3Pal$^{3}$ -Ser$^{4}$-Phe(Atz)$^{5}$-DPhe(Atz)$^{6}$ -Leu$^{7}$-Lys(Isp)$^{8}$-Pro$^{9}$-DAla$^{10}$NH$_{2}$;

5LactD4ClPhe$^{1}$-D4ClPhe$^{2}$-D3Pal$^{3}$ -Ser$^{4}$-Phe(Atz)$^{5}$-DPhe(Atz)$^{6}$ -Leu$^{7}$-Lys(Isp)$^{8}$-Pro$^{9}$-DAla$^{10}$NH$_{2}$;

5LactDPhe$^{1}$-D4ClPhe$^{2}$-D3Pal$^{3}$ -Ser$^{4}$-Phe(Atz)$^{5}$-DPhe(Atz)$^{6}$ -Leu$^{7}$-Lys(Isp)$^{8}$-Pro$^{9}$-DAla$^{10}$NH$_{2}$;

5LactD1Nal$^{1}$-D4ClPhe$^{2}$-D3Pal$^{3}$ -Ser$^{4}$-Phe(Atz)$^{5}$-DPhe(Atz)$^{6}$ -Leu$^{7}$-Lys(Isp)$^{8}$-Pro$^{9}$-DAla$^{10}$NH$_{2}$;

6LactGly$^{1}$-D4ClPhe$^{2}$-D3Pal$^{3}$ -Ser$^{4}$-Phe(Atz)$^{5}$-DPhe(Atz)$^{6}$ -Leu$^{7}$-Lys(Isp)$^{8}$-Pro$^{9}$-DAla$^{10}$NH$_{2}$;

6LactD3Qal$^{1}$-D4ClPhe$^{2}$-D3Pal$^{3}$ -Ser$^{4}$-Phe(Atz)$^{5}$-DPhe(Atz)$^{6}$ -Leu$^{7}$-Lys(Isp)$^{8}$-Pro$^{9}$-DAla$^{10}$NH$_{2}$;

6LactD4ClPhe$^{1}$-D4ClPhe$^{2}$-D3Pal$^{3}$ -Ser$^{4}$-Phe(Atz)$^{5}$-DPhe(Atz)$^{6}$ -Leu$^{7}$-Lys(Isp)$^{8}$-Pro$^{9}$-DAla$^{10}$NH$_{2}$;

6LactDPhe$^{1}$-D4ClPhe$^{2}$-D3Pal$^{3}$ -Ser$^{4}$-Phe(Atz)$^{5}$-DPhe(Atz)$^{6}$ -Leu$^{7}$-Lys(Isp)$^{8}$-Pro$^{9}$-DAla$^{10}$NH$_{2}$;

6LactD1Nal$^{1}$-D4ClPhe$^{2}$-D3Pal$^{3}$ -Ser$^{4}$-Phe(Atz)$^{5}$-DPhe(Atz)$^{6}$ -Leu$^{7}$-Lys(Isp)$^{8}$-Pro$^{9}$-DAla$^{10}$NH$_{2}$;

7LactGly$^{1}$-D4ClPhe$^{2}$-D3Pal$^{3}$ -Ser$^{4}$-Phe(Atz)$^{5}$-DPhe(Atz)$^{6}$ -Leu$^{7}$-Lys(Isp)$^{8}$-Pro$^{9}$-DAla$^{10}$NH$_{2}$;

7LactD2Nal$^{1}$-D4ClPhe$^{2}$-D3Pal$^{3}$ -Ser$^{4}$-Phe(Atz)$^{5}$-DPhe(Atz)$^{6}$ -Leu$^{7}$-Lys(Isp)$^{8}$-Pro$^{9}$-DAla$^{10}$NH$_{2}$;

7LactD3Qal$^{1}$-D4ClPhe$^{2}$-D3Pal$^{3}$ -Ser$^{4}$-Phe(Atz)$^{5}$-DPhe(Atz)$^{6}$ -Leu$^{7}$-Lys(Isp)$^{8}$-Pro$^{9}$-DAla$^{10}$NH$_{2}$;

7LactD4ClPhe$^{1}$-D4ClPhe$^{2}$-D3Pal$^{3}$ -Ser$^{4}$-Phe(Atz)$^{5}$-DPhe(Atz)$^{6}$ -Leu$^{7}$-Lys(Isp)$^{8}$-Pro$^{9}$-DAla$^{10}$NH$_{2}$;

7LactDPhe$^{1}$-D4ClPhe$^{2}$-D3Pal$^{3}$ -Ser$^{4}$-Phe(Atz)$^{5}$-DPhe(Atz)$^{6}$ -Leu$^{7}$-Lys(Isp)$^{8}$-Pro$^{9}$-DAla$^{10}$NH$_{2}$;

7LactD1Nal$^{1}$-D4ClPhe$^{2}$-D3Pal$^{3}$ -Ser$^{4}$-Phe(Atz)$^{5}$-DPhe(Atz)$^{6}$ -Leu$^{7}$-Lys(Isp)$^{8}$-Pro$^{9}$-DAla$^{10}$NH$_{2}$;

6LactD2Nal$^{1}$-D4ClPhe$^{2}$-D3Pal$^{3}$ -Ser$^{4}$-Phe(Atz)$^{5}$-DPhe(Atz)$^{6}$ -Leu$^{7}$-Lys(Isp)$^{8}$-Pro$^{9}$-DAla$^{10}$NH$_{2}$;

5LactGly$^{1}$-D4ClPhe$^{2}$-D3Pal$^{3}$ -Ser$^{4}$-NMePhe(Atz)$^{5}$-DPhe(Atz)$^{6}$ -Leu$^{7}$-Lys(Isp)$^{8}$-Pro$^{9}$-DAla$^{10}$NH$_{2}$;

5LactD3Qal$^{1}$-D4ClPhe$^{2}$-D3Pal$^{3}$ -Ser$^{4}$-NMePhe(Atz)$^{5}$-DPhe(Atz)$^{6}$ -Leu$^{7}$-Lys(Isp)$^{8}$-Pro$^{9}$-DAla$^{10}$NH$_{2}$;

5LactD4ClPhe$^{1}$-D4ClPhe$^{2}$-D3Pal$^{3}$ -Ser$^{4}$-NMePhe(Atz)$^{5}$-DPhe(Atz)$^{6}$ -Leu$^{7}$-Lys(Isp)$^{8}$-Pro$^{9}$-DAla$^{10}$NH$_{2}$;

5LactDPhe$^{1}$-D4ClPhe$^{2}$-D3Pal$^{3}$ -Ser$^{4}$-NMePhe(Atz)$^{5}$-DPhe(Atz)$^{6}$ -Leu$^{7}$-Lys(Isp)$^{8}$-Pro$^{9}$-DAla$^{10}$NH$_{2}$;

5LactD1Nal$^{1}$-D4ClPhe$^{2}$-D3Pal$^{3}$ -Ser$^{4}$-NMePhe(Atz)$^{5}$-DPhe(Atz)$^{6}$ -Leu$^{7}$-Lys(Isp)$^{8}$-Pro$^{9}$-DAla$^{10}$NH$_{2}$;

6LactGly$^{1}$-D4ClPhe$^{2}$-D3Pal$^{3}$ -Ser$^{4}$-NMePhe(Atz)$^{5}$-DPhe(Atz)$^{6}$ -Leu$^{7}$-Lys(Isp)$^{8}$-Pro$^{9}$-DAla$^{10}$NH$_{2}$;

6LactD3Qal$^{1}$-D4ClPhe$^{2}$-D3Pal$^{3}$ -Ser$^{4}$-NMePhe(Atz)$^{5}$-DPhe(Atz)$^{6}$ -Leu$^{7}$-Lys(Isp)$^{8}$-Pro$^{9}$-DAla$^{10}$NH$_{2}$;

6LactD4ClPhe$^{1}$-D4ClPhe$^{2}$-D3Pal$^{3}$ -Ser$^{4}$-NMePhe(Atz)$^{5}$-DPhe(Atz)$^{6}$ -Leu$^{7}$-Lys(Isp)$^{8}$-Pro$^{9}$-DAla$^{10}$NH$_{2}$;

6LactDPhe$^{1}$-D4ClPhe$^{2}$-D3Pal$^{3}$ -Ser$^{4}$-NMePhe(Atz)$^{5}$-DPhe(Atz)$^{6}$ -Leu$^{7}$-Lys(Isp)$^{8}$-Pro$^{9}$-DAla$^{10}$NH$_{2}$;

6LactD1Nal$^{1}$-D4ClPhe$^{2}$-D3Pal$^{3}$ -Ser$^{4}$-NMePhe(Atz)$^{5}$-DPhe(Atz)$^{6}$ -Leu$^{7}$-Lys(Isp)$^{8}$-Pro$^{9}$-DAla$^{10}$NH$_{2}$;

7LactGly$^{1}$-D4ClPhe$^{2}$-D3Pal$^{3}$ -Ser$^{4}$-NMePhe(Atz)$^{5}$-DPhe(Atz)$^{6}$ -Leu$^{7}$-Lys(Isp)$^{8}$-Pro$^{9}$-DAla$^{10}$NH$_{2}$;

7LactD2Nal$^{1}$-D4ClPhe$^{2}$-D3Pal$^{3}$ -Ser$^{4}$-NMePhe(Atz)$^{5}$-DPhe(Atz)$^{6}$ -Leu$^{7}$-Lys(Isp)$^{8}$-Pro$^{9}$-DAla$^{10}$NH$_{2}$;

7LactD3Qal$^{1}$-D4ClPhe$^{2}$-D3Pal$^{3}$ -Ser$^{4}$-NMePhe(Atz)$^{5}$-DPhe(Atz)$^{6}$ -Leu$^{7}$-Lys(Isp)$^{8}$-Pro$^{9}$-DAla$^{10}$NH$_{2}$;

7LactD4ClPhe$^{1}$-D4ClPhe$^{2}$-D3Pal$^{3}$ -Ser$^{4}$-NMePhe(Atz)$^{5}$-DPhe(Atz)$^{6}$ -Leu$^{7}$-Lys(Isp)$^{8}$-Pro$^{9}$-DAla$^{10}$NH$_{2}$;

7LactDPhe$^{1}$-D4ClPhe$^{2}$-D3Pal$^{3}$ -Ser$^{4}$-NMePhe(Atz)$^{5}$-DPhe(Atz)$^{6}$ -Leu$^{7}$-Lys(Isp)$^{8}$-Pro$^{9}$-DAla$^{10}$NH$_{2}$;

7LactD1Nal$^{1}$-D4ClPhe$^{2}$-D3Pal$^{3}$ -Ser$^{4}$-NMePhe(Atz)$^{5}$-DPhe(Atz)$^{6}$ -Leu$^{7}$-Lys(Isp)$^{8}$-Pro$^{9}$-DAla$^{10}$NH$_{2}$;

6LactD2Nal$^{1}$-D4ClPhe$^{2}$-D3Pal$^{3}$ -Ser$^{4}$-NMePhe(Atz)$^{5}$-DPhe(Atz)$^{6}$ -Leu$^{7}$-Lys(Isp)$^{8}$-Pro$^{9}$-DAla$^{10}$NH$_{2}$;

5LactD2Nal$^{1}$-D4ClPhe$^{2}$-D3Pal$^{3}$ -Ser$^{4}$-NMePhe(Atz)$^{5}$-DPhe(Atz)$^{6}$ -Leu$^{7}$-Lys(Isp)$^{8}$-Pro$^{9}$-DAla$^{10}$NH$_{2}$;

5LactD2Nal$^{1}$-D4ClPhe$^{2}$-D3Pal$^{3}$ -Ser$^{4}$-Tyr$^{5}$-DHarg(Et$_{2}$)$^{6}$ -Leu$^{7}$-HArg(Et$_{2}$)$^{8}$-Pro$^{9}$-DAla$^{10}$NH$_{2}$;

5LactGly$^{1}$-D4ClPhe$^{2}$-D3Pal$^{3}$ -Ser$^{4}$-NMePhe(Atz)$^{5}$-DPhe(Atz)$^{6}$ -Leu$^{7}$-HArg(Et$_{2}$)$^{8}$-Pro$^{9}$-DAla$^{10}$NH$_{2}$;

5LactD3Qal$^{1}$-D4ClPhe$^{2}$-D3Pal$^{3}$ -Ser$^{4}$-Tyr$^{5}$-DHarg(Et$_{2}$)$^{6}$ -Leu$^{7}$-Lys(Isp)$^{8}$-Pro$^{9}$-DAla$^{10}$NH$_{2}$;

5LactD4ClPhe$^{1}$-D4ClPhe$^{2}$-D3Pal$^{3}$ -Ser$^{4}$-Tyr$^{5}$-DHarg(Et$_{2}$)$^{6}$ -Leu$^{7}$-HArg(Et$_{2}$)$^{8}$-Pro$^{9}$-DAla$^{10}$NH$_{2}$;

5LactDPhe$^{1}$-D4ClPhe$^{2}$-D3Pal$^{3}$ -Ser$^{4}$-Tyr$^{5}$-DHarg(Et$_{2}$)$^{6}$ -Leu$^{7}$-HArg(Et$_{2}$)$^{8}$-Pro$^{9}$-DAla$^{10}$NH$_{2}$;

5LactD1Nal$^{1}$-D4ClPhe$^{2}$-D3Pal$^{3}$ -Ser$^{4}$-Tyr$^{5}$-DHarg(Et$_{2}$)$^{6}$ -Leu$^{7}$-HArg(Et$_{2}$)$^{8}$-Pro$^{9}$-DAla$^{10}$NH$_{2}$;

6LactGly$^{1}$-D4ClPhe$^{2}$-D3Pal$^{3}$ -Ser$^{4}$-Tyr$^{5}$-DHarg(Et$_{2}$)$^{6}$ -Leu$^{7}$-HArg(Et$_{2}$)$^{8}$-Pro$^{9}$-DAla$^{10}$NH$_{2}$;

6LactD3Qal$^{1}$-D4ClPhe$^{2}$-D3Pal$^{3}$ -Ser$^{4}$-Tyr$^{5}$-DHarg(Et$_{2}$)$^{6}$ -Leu$^{7}$-HArg(Et$_{2}$)$^{8}$-Pro$^{9}$-DAla$^{10}$NH$_{2}$;

6LactD4ClPhe$^{1}$-D4ClPhe$^{2}$-D3Pal$^{3}$ -Ser$^{4}$-Tyr$^{5}$-DHarg(Et$_{2}$)$^{6}$ -Leu$^{7}$-HArg(Et$_{2}$)$^{8}$-Pro$^{9}$-DAla$^{10}$NH$_{2}$;

6LactDPhe$^{1}$-D4ClPhe$^{2}$-D3Pal$^{3}$ -Ser$^{4}$-Tyr$^{5}$-DHarg(Et$_{2}$)$^{6}$ -Leu$^{7}$-HArg(Et$_{2}$)$^{8}$-Pro$^{9}$-DAla$^{10}$NH$_{2}$;

6LactD1Nal$^{1}$-D4ClPhe$^{2}$-D3Pal$^{3}$ -Ser$^{4}$-Tyr$^{5}$-DHarg(Et$_{2}$)$^{6}$ -Leu$^{7}$-HArg(Et$_{2}$)$^{8}$-Pro$^{9}$-DAla$^{10}$NH$_{2}$;

7LactGly$^{1}$-D4ClPhe$^{2}$-D3Pal$^{3}$ -Ser$^{4}$-Tyr$^{5}$-DHarg(Et$_{2}$)$^{6}$ -Leu$^{7}$-HArg(Et$_{2}$)$^{8}$-Pro$^{9}$-DAla$^{10}$NH$_{2}$;

7LactD2Nal$^{1}$-D4ClPhe$^{2}$-D3Pal$^{3}$ -Ser$^{4}$-Tyr$^{5}$-DHarg(Et$_{2}$)$^{6}$ -Leu$^{7}$-HArg(Et$_{2}$)$^{8}$-Pro$^{9}$-DAla$^{10}$NH$_{2}$;

7LactD3Qal$^{1}$-D4ClPhe$^{2}$-D3Pal$^{3}$ -Ser$^{4}$-Tyr$^{5}$-DHarg(Et$_{2}$)$^{6}$ -Leu$^{7}$-HArg(Et$_{2}$)$^{8}$-Pro$^{9}$-DAla$^{10}$NH$_{2}$;

7LactD4ClPhe$^{1}$-D4ClPhe$^{2}$-D3Pal$^{3}$ -Ser$^{4}$-Tyr$^{5}$-DHarg(Et$_{2}$)$^{6}$ -Leu$^{7}$-HArg(Et$_{2}$)$^{8}$-Pro$^{9}$-DAla$^{10}$NH$_{2}$;

7LactDPhe$^{1}$-D4ClPhe$^{2}$-D3Pal$^{3}$ -Ser$^{4}$-Tyr$^{5}$-DHarg(Et$_{2}$)$^{6}$ -Leu$^{7}$-HArg(Et$_{2}$)$^{8}$-Pro$^{9}$-DAla$^{10}$NH$_{2}$;

7LactD1Nal$^{1}$-D4ClPhe$^{2}$-D3Pal$^{3}$ -Ser$^{4}$-Tyr$^{5}$-DHarg(Et$_{2}$)$^{6}$ -Leu$^{7}$-HArg(Et$_{2}$)$^{8}$-Pro$^{9}$-DAla$^{10}$NH$_{2}$;

6LactD2Nal$^{1}$-D4ClPhe$^{2}$-D3Pal$^{3}$ -Ser$^{4}$-Tyr$^{5}$-DHarg(Et$_{2}$)$^{6}$ -Leu$^{7}$-HArg(Et$_{2}$)$^{8}$-Pro$^{9}$-DAla$^{10}$NH$_{2}$;

5LactD2Nal$^1$-D4ClPhe$^2$-D3Pal$^3$-Ser$^4$-Tyr$^5$-DLys(Shik)$^6$-Leu$^7$-Arg$^8$-Pro$^9$-DAla$^{10}$NH$_2$;

5LactGly$^1$-D4ClPhe$^2$-D3Pal$^3$-Ser$^4$-Tyr$^5$-DLys(Shik)$^6$-Leu$^7$-Arg$^8$-Pro$^9$-DAla$^{10}$NH$_2$;

5LactD3Qal$^1$-D4ClPhe$^2$-D3Pal$^3$-Ser$^4$-Tyr$^5$-DLys(Shik)$^6$-Leu$^7$-Arg$^8$-Pro$^9$-DAla$^{10}$NH$_2$;

5LactD4ClPhe$^1$-D4ClPhe$^2$-D3Pal$^3$-Ser$^4$-Tyr$^5$-DLys(Shik)$^6$-Leu$^7$-Arg$^8$-Pro$^9$-DAla$^{10}$NH$_2$;

5LactDPhe$^1$-D4ClPhe$^2$-D3Pal$^3$-Ser$^4$-Tyr$^5$-DLys(Shik)$^6$-Leu$^7$-Arg$^8$-Pro$^9$-DAla$^{10}$NH$_2$;

5LactD1Nal$^1$-D4ClPhe$^2$-D3Pal$^3$-Ser$^4$-Tyr$^5$-DLys(Shik)$^6$-Leu$^7$-Arg$^8$-Pro$^9$-DAla$^{10}$NH$_2$;

6LactGly$^1$-D4ClPhe$^2$-D3Pal$^3$-Ser$^4$-Tyr$^5$-DLys(Shik)$^6$-Leu$^7$-Arg$^8$-Pro$^9$-DAla$^{10}$NH$_2$;

6LactD3Qal$^1$-D4ClPhe$^2$-D3Pal$^3$-Ser$^4$-Tyr$^5$-DLys(Shik)$^6$-Leu$^7$-Arg$^8$-Pro$^9$-DAla$^{10}$NH$_2$;

6LactD4ClPhe$^1$-D4ClPhe$^2$-D3Pal$^3$-Ser$^4$-Tyr$^5$-DLys(Shik)$^6$-Leu$^7$-Arg$^8$-Pro$^9$-DAla$^{10}$NH$_2$;

6LactDPhe$^1$-D4ClPhe$^2$-D3Pal$^3$-Ser$^4$-Tyr$^5$-DLys(Shik)$^6$-Leu$^7$-Arg$^8$-Pro$^9$-DAla$^{10}$NH$_2$;

6LactD1Nal$^1$-D4ClPhe$^2$-D3Pal$^3$-Ser$^4$-Tyr$^5$-DLys(Shik)$^6$-Leu$^7$-Arg$^8$-Pro$^9$-DAla$^{10}$NH$_2$;

7LactGly$^1$-D4ClPhe$^2$-D3Pal$^3$-Ser$^4$-Tyr$^5$-DLys(Shik)$^6$-Leu$^7$-Arg$^8$-Pro$^9$-DAla$^{10}$NH$_2$;

7LactD2Nal$^1$-D4ClPhe$^2$-D3Pal$^3$-Ser$^4$-Tyr$^5$-DLys(Shik)$^6$-Leu$^7$-Arg$^8$-Pro$^9$-DAla$^{10}$NH$_2$;

7LactD3Qal$^1$-D4ClPhe$^2$-D3Pal$^3$-Ser$^4$-Tyr$^5$-DLys(Shik)$^6$-Leu$^7$-Arg$^8$-Pro$^9$-DAla$^{10}$NH$_2$;

7LactD4ClPhe$^1$-D4ClPhe$^2$-D3Pal$^3$-Ser$^4$-Tyr$^5$-DLys(Shik)$^6$-Leu$^7$-Arg$^8$-Pro$^9$-DAla$^{10}$NH$_2$;

7LactDPhe$^1$-D4ClPhe$^2$-D3Pal$^3$-Ser$^4$-Tyr$^5$-DLys(Shik)$^6$-Leu$^7$-Arg$^8$-Pro$^9$-DAla$^{10}$NH$_2$;

7LactD1Nal$^1$-D4ClPhe$^2$-D3Pal$^3$-Ser$^4$-Tyr$^5$-DLys(Shik)$^6$-Leu$^7$-Arg$^8$-Pro$^9$-DAla$^{10}$NH$_2$;

6LactD2Nal$^1$-D4ClPhe$^2$-D3Pal$^3$-Ser$^4$-Tyr$^5$-DLys(Shik)$^6$-Leu$^7$-Arg$^8$-Pro$^9$-DAla$^{10}$NH$_2$;

5LactD2Nal$^1$-D4ClPhe$^2$-D3Pal$^3$-Ser$^4$-Tyr$^5$-DLys(GlyShik)$^6$-Leu$^7$-Arg$^8$-Pro$^9$-DAla$^{10}$NH$_2$;

5LactGly$^1$-D4ClPhe$^2$-D3Pal$^3$-Ser$^4$-Tyr$^5$-DLys(GlyShik)$^6$-Leu$^7$-Arg$^8$-Pro$^9$-DAla$^{10}$NH$_2$;

5LactD3Qal$^1$-D4ClPhe$^2$-D3Pal$^3$-Ser$^4$-Tyr$^5$-DLys(GlyShik)$^6$-Leu$^7$-Arg$^8$-Pro$^9$-DAla$^{10}$NH$_2$;

5LactD4ClPhe$^1$-D4ClPhe$^2$-D3Pal$^3$-Ser$^4$-Tyr$^5$-DLys(GlyShik)$^6$-Leu$^7$-Arg$^8$-Pro$^9$-DAla$^{10}$NH$_2$;

5LactDPhe$^1$-D4ClPhe$^2$-D3Pal$^3$-Ser$^4$-Tyr$^5$-DLys(GlyShik)$^6$-Leu$^7$-Arg$^8$-Pro$^9$-DAla$^{10}$NH$_2$;

5LactD1Nal$^1$-D4ClPhe$^2$-D3Pal$^3$-Ser$^4$-Tyr$^5$-DLys(GlyShik)$^6$-Leu$^7$-Arg$^8$-Pro$^9$-DAla$^{10}$NH$_2$;

6LactGly$^1$-D4ClPhe$^2$-D3Pal$^3$-Ser$^4$-Tyr$^5$-DLys(GlyShik)$^6$-Leu$^7$-Arg$^8$-Pro$^9$-DAla$^{10}$NH$_2$;

6LactD3Qal$^1$-D4ClPhe$^2$-D3Pal$^3$-Ser$^4$-Tyr$^5$-DLys(GlyShik)$^6$-Leu$^7$-Arg$^8$-Pro$^9$-DAla$^{10}$NH$_2$;

6LactD4ClPhe$^1$-D4ClPhe$^2$-D3Pal$^3$-Ser$^4$-Tyr$^5$-DLys(GlyShik)$^6$-Leu$^7$-Arg$^8$-Pro$^9$-DAla$^{10}$NH$_2$;

6LactD3Phe$^1$-D4ClPhe$^2$-D3Pal$^3$-Ser$^4$-Tyr$^5$-DLys(GlyShik)$^6$-Leu$^7$-Arg$^8$-Pro$^9$-DAla$^{10}$NH$_2$;

6LactD1Nal$^1$-D4ClPhe$^2$-D3Pal$^3$-Ser$^4$-Tyr$^5$-DLys(GlyShik)$^6$-Leu$^7$-Arg$^8$-Pro$^9$-DAla$^{10}$NH$_2$;

7LactGly$^1$-D4ClPhe$^2$-D3Pal$^3$-Ser$^4$-Tyr$^5$-DLys(GlyShik)$^6$-Leu$^7$-Arg$^8$-Pro$^9$-DAla$^{10}$NH$_2$;

7LactD2Nal$^1$-D4ClPhe$^2$-D3Pal$^3$-Ser$^4$-Tyr$^5$-DLys(GlyShik)$^6$-Leu$^7$-Arg$^8$-Pro$^9$-DAla$^{10}$NH$_2$;

7LactD3Qal$^1$-D4ClPhe$^2$-D3Pal$^3$-Ser$^4$-Tyr$^5$-DLys(GlyShik)$^6$-Leu$^7$-Arg$^8$-Pro$^9$-DAla$^{10}$NH$_2$;

7LactD4ClPhe$^1$-D4ClPhe$^2$-D3Pal$^3$-Ser$^4$-Tyr$^5$-DLys(GlyShik)$^6$-Leu$^7$-Arg$^8$-Pro$^9$-DAla$^{10}$NH$_2$;

7LactDPhe$^1$-D4ClPhe$^2$-D3Pal$^3$-Ser$^4$-Tyr$^5$-DLys(GlyShik)$^6$-Leu$^7$-Arg$^8$-Pro$^9$-DAla$^{10}$NH$_2$;

7LactD1Nal$^1$-D4ClPhe$^2$-D3Pal$^3$-Ser$^4$-Tyr$^5$-DLys(GlyShik)$^6$-Leu$^7$-Arg$^8$-Pro$^9$-DAla$^{10}$NH$_2$;

6LactD2Nal$^1$-D4ClPhe$^2$-D3Pal$^3$-Ser$^4$-Tyr$^5$-DLys(GlyShik)$^6$-Leu$^7$-Arg$^8$-Pro$^9$-DAla$^{10}$NH$_2$;

5LactD2Nal$^1$-D4ClPhe$^2$-D3Pal$^3$-Ser$^4$-Tyr$^5$-DLys(Shik)$^6$-Leu$^7$-Harg$^8$-Pro$^9$-DAla$^{10}$NH$_2$;

5LactGly$^1$-D4ClPhe$^2$-D3Pal$^3$-Ser$^4$-Tyr$^5$-DLys(Shik)$^6$-Leu$^7$-Harg$^8$-Pro$^9$-DAla$^{10}$NH$_2$;

5LactD3Qal$^1$-D4ClPhe$^2$-D3Pal$^3$-Ser$^4$-Tyr$^5$-DLys(Shik)$^6$-Leu$^7$-Harg$^8$-Pro$^9$-DAla$^{10}$NH$_2$;

5LactD4ClPhe$^1$-D4ClPhe$^2$-D3Pal$^3$-Ser$^4$-Tyr$^5$-DLys(Shik)$^6$-Leu$^7$-Harg$^8$-Pro$^9$-DAla$^{10}$NH$_2$;

5LactDPhe$^1$-D4ClPhe$^2$-D3Pal$^3$-Ser$^4$-Tyr$^5$-DLys(Shik)$^6$-Leu$^7$-Harg$^8$-Pro$^9$-DAla$^{10}$NH$_2$;

5LactD1Nal$^1$-D4ClPhe$^2$-D3Pal$^3$-Ser$^4$-Tyr$^5$-DLys(Shik)$^6$-Leu$^7$-Harg$^8$-Pro$^9$-DAla$^{10}$NH$_2$;

6LactGly$^1$-D4ClPhe$^2$-D3Pal$^3$-Ser$^4$-Tyr$^5$-DLys(Shik)$^6$-Leu$^7$-Harg$^8$-Pro$^9$-DAla$^{10}$NH$_2$;

6LactD3Qal$^1$-D4ClPhe$^2$-D3Pal$^3$-Ser$^4$-Tyr$^5$-DLys(Shik)$^6$-Leu$^7$-Harg$^8$-Pro$^9$-DAla$^{10}$NH$_2$;

6LactD4ClPhe$^1$-D4ClPhe$^2$-D3Pal$^3$-Ser$^4$-Tyr$^5$-DLys(Shik)$^6$-Leu$^7$-Harg$^8$-Pro$^9$-DAla$^{10}$NH$_2$;

6LactDPhe$^1$-D4ClPhe$^2$-D3Pal$^3$-Ser$^4$-Tyr$^5$-DLys(Shik)$^6$-Leu$^7$-Harg$^8$-Pro$^9$-DAla$^{10}$NH$_2$;

6LactD1Nal$^1$-D4ClPhe$^2$-D3Pal$^3$-Ser$^4$-Tyr$^5$-DLys(Shik)$^6$-Leu$^7$-Harg$^8$-Pro$^9$-DAla$^{10}$NH$_2$;

7LactGly$^1$-D4ClPhe$^2$-D3Pal$^3$-Ser$^4$-Tyr$^5$-DLys(Shik)$^6$-Leu$^7$-Harg$^8$-Pro$^9$-DAla$^{10}$NH$_2$;

7LactD2Nal$^1$-D4ClPhe$^2$-D3Pal$^3$-Ser$^4$-Tyr$^5$-DLys(Shik)$^6$-Leu$^7$-Harg$^8$-Pro$^9$-DAla$^{10}$NH$_2$;

7LactD3Qal$^1$-D4ClPhe$^2$-D3Pal$^3$-Ser$^4$-Tyr$^5$-DLys(Shik)$^6$-Leu$^7$-Harg$^8$-Pro$^9$-DAla$^{10}$NH$_2$;

7LactD4ClPhe$^1$-D4ClPhe$^2$-D3Pal$^3$-Ser$^4$-Tyr$^5$-DLys(Shik)$^6$-Leu$^7$-Harg$^8$-Pro$^9$-DAla$^{10}$NH$_2$;

7LactDPhe$^1$-D4ClPhe$^2$-D3Pal$^3$-Ser$^4$-Tyr$^5$-DLys(Shik)$^6$-Leu$^7$-Harg$^8$-Pro$^9$-DAla$^{10}$NH$_2$;

7LactD1Nal$^1$-D4ClPhe$^2$-D3Pal$^3$-Ser$^4$-Tyr$^5$-DLys(Shik)$^6$-Leu$^7$-Harg$^8$-Pro$^9$-DAla$^{10}$NH$_2$;

6LactD2Nal$^1$-D4ClPhe$^2$-D3Pal$^3$-Ser$^4$-Tyr$^5$-DLys(Shik)$^6$-Leu$^7$-Harg$^8$-Pro$^9$-DAla$^{10}$NH$_2$;

5LactD2Nal$^1$-D4ClPhe$^2$-D3Pal$^3$-Ser$^4$-Tyr$^5$-DLys(GlyShik)$^6$-Leu$^7$-Harg$^8$-Pro$^9$-DAla$^{10}$NH$_2$;

5LactGly$^1$-D4ClPhe$^2$-D3Pal$^3$-Ser$^4$-Tyr$^5$-DLys(GlyShik)$^6$-Leu$^7$-Harg$^8$-Pro$^9$-DAla$^{10}$NH$_2$;

5LactD3Qal$^1$-D4ClPhe$^2$-D3Pal$^3$-Ser$^4$-Tyr$^5$-DLys(GlyShik)$^6$-Leu$^7$-Harg$^8$-Pro$^9$-DAla$^{10}$NH$_2$;

5LactD4ClPhe$^1$-D4ClPhe$^2$-D3Pal$^3$-Ser$^4$-Tyr$^5$-DLys(GlyShik)$^6$-Leu$^7$-Harg$^8$-Pro$^9$-DAla$^{10}$NH$_2$;

5LactDPhe$^1$-D4ClPhe$^2$-D3Pal$^3$-Ser$^4$-Tyr$^5$-DLys(GlyShik)$^6$-Leu$^7$-Harg$^8$-Pro$^9$-DAla$^{10}$NH$_2$;

5LactD1Nal$^1$-D4ClPhe$^2$-D3Pal$^3$-Ser$^4$-Tyr$^5$-DLys(GlyShik)$^6$-Leu$^7$-Harg$^8$-Pro$^9$-DAla$^{10}$NH$_2$;

6LactGly$^1$-D4ClPhe$^2$-D3Pal$^3$-Ser$^4$-Tyr$^5$-DLys(GlyShik)$^6$-Leu$^7$-Harg$^8$-Pro$^9$-DAla$^{10}$NH$_2$;

6LactD3Qal$^1$-D4ClPhe$^2$-D3Pal$^3$-Ser$^4$-Tyr$^5$-DLys(GlyShik)$^6$-Leu$^7$-Harg$^8$-Pro$^9$-DAla$^{10}$NH$_2$;

6LactD4ClPhe$^1$-D4ClPhe$^2$-D3Pal$^3$-Ser$^4$-Tyr$^5$-DLys(GlyShik)$^6$-Leu$^7$-Harg$^8$-Pro$^9$-DAla$^{10}$NH$_2$;

6LactDPhe$^1$-D4ClPhe$^2$-D3Pal$^3$-Ser$^4$-Tyr$^5$-DLys(GlyShik)$^6$-Leu$^7$-Harg$^8$-Pro$^9$-DAla$^{10}$NH$_2$;

6LactD1Nal$^1$-D4ClPhe$^2$-D3Pal$^3$-Ser$^4$-Tyr$^5$-DLys(GlyShik)$^6$-Leu$^7$-Harg$^8$-Pro$^9$-DAla$^{10}$NH$_2$;

7LactGly$^1$-D4ClPhe$^2$-D3Pal$^3$-Ser$^4$-Tyr$^5$-DLys(GlyShik)$^6$-Leu$^7$-Harg$^8$-Pro$^9$-DAla$^{10}$NH$_2$;

7LactD2Nal$^1$-D4ClPhe$^2$-D3Pal$^3$-Ser$^4$-Tyr$^5$-DLys(GlyShik)$^6$-Leu$^7$-Harg$^8$-Pro$^9$-DAla$^{10}$NH$_2$;

7LactD3Qal$^1$-D4ClPhe$^2$-D3Pal$^3$-Ser$^4$-Tyr$^5$-DLys(GlyShik)$^6$-Leu$^7$-Harg$^8$-Pro$^9$-DAla$^{10}$NH$_2$;

7LactD4ClPhe$^1$-D4ClPhe$^2$-D3Pal$^3$ -Ser$^4$-Tyr$^5$-DLys(Gly-Shik)$^6$ -Leu$^7$-Harg$^8$-Pro$^9$-DAla$^{10}$NH$_2$;

7LactDPhe$^1$-D4ClPhe$^2$-D3Pal$^3$ -Ser$^4$-Tyr$^5$-DLys(GlyShik)$^6$ -Leu$^7$-Harg$^8$-Pro$^9$-DAla$^{10}$NH$_2$;

7LactD1Nal$^1$-D4ClPhe$^2$-D3Pal$^3$ -Ser$^4$-Tyr$^5$-DLys(Gly-Shik)$^6$ -Leu$^7$-Harg$^8$-Pro$^9$-DAla$^{10}$NH$_2$;

6LactD2Nal$^1$-D4ClPhe$^2$-D3Pal$^3$ -Ser$^4$-Tyr$^5$-DLys(Gly-Shik)$^6$ -Leu$^7$-Harg$^8$-Pro$^9$-DAla$^{10}$NH$_2$;

the Most preferred compounds in accordance with the present invention are:

5LactD2Nal$^1$-D4ClPhe$^2$-D3Pal$^3$ -Ser$^4$-NMeTyr$^5$-DCit$^6$ -Leu$^7$-Arg$^8$-Pro$^9$-DAla$^{10}$NH$_2$;

5LactD2Nal$^1$-D4ClPhe$^2$-D3Pal$^3$ -Ser$^4$-NMeTyr$^5$-DLys(N-epsilon-Shik)$^6$ -Leu$^7$-Arg$^8$-Pro$^9$-DAla$^{10}$NH$_2$;

5LactD2Nal$^1$-D4ClPhe$^2$-D3Pal$^3$ -Ser$^4$-NMeTyr$^5$-DLys(N-epsilon-Gly-Shik)$^6$ -Leu$^7$-Arg$^8$-Pro$^9$-DAla$^{10}$NH$_2$;

5LactD2Nal$^1$-D4ClPhe$^2$-D3Pal$^3$ -Ser$^4$-NMeTyr$^5$-DLys(N-epsilon-Shik)$^6$ -Leu$^7$-Harg$^8$-Pro$^9$-DAla$^{10}$NH$_2$;

5LactD2Nal$^1$-D4ClPhe$^2$-D3Pal$^3$ -Ser$^4$-NMeTyr$^5$-DLys(N-epsilon-Gly-Shik)$^6$ -Leu$^7$-Harg$^8$-Pro$^9$-DAla$^{10}$NH$_2$;

5LactD2Nal$^1$-D4ClPhe$^2$-D3Pal$^3$ -Ser$^4$-Tyr$^5$-DCit$^6$ -Leu$^7$-Arg$^8$-Pro$^9$-DAla$^{10}$NH$_2$;

5LactD2Nal$^1$-D4ClPhe$^2$-D3Pal$^3$ -Ser$^4$-NMeTyr$^5$-DLys(N-epsilon-Nic)$^6$ -Leu$^7$-Lys(N-epsilon-Isopropyl)$^8$-Pro$^9$-DAla$^{10}$NH$_2$;

6LactD2Nal$^1$-D4ClPhe$^2$-D3Pal$^3$ -Ser$^4$-NMeTyr$^5$-DLys(N-epsilon-Shik)$^6$ -Leu$^7$-Arg$^8$-Pro$^9$-DAla$^{10}$NH$_2$;

6LactD2Nal$^1$-D4ClPhe$^2$-D3Pal$^3$ -Ser$^4$-NMeTyr$^5$-DLys(N-epsilon-Gly-Shik)$^6$ -Leu$^7$-Arg$^8$-Pro$^9$-DAla$^{10}$NH$_2$;

6LactD2Nal$^1$-D4ClPhe$^2$-D3Pal$^3$ -Ser$^4$-NMeTyr$^5$-DLys(N-epsilon-Shik)$^6$ -Leu$^7$-Harg$^8$-Pro$^9$-DAla$^{10}$NH$_2$;

6LactD2Nal$^1$-D4ClPhe$^2$-D3Pal$^3$ -Ser$^4$-NMeTyr$^5$-DLys(N-epsilon-Gly-Shik)$^6$ -Leu$^7$-Harg$^8$-Pro$^9$-DAla$^{10}$NH$_2$;

5LactD2Nal$^1$-D4ClPhe$^2$-D3Pal$^3$ -Ser$^4$-Tyr$^5$-DHcit$^6$ -Leu$^7$-Lys(isp)$^8$-Pro$^9$-DAla$^{10}$NH$_2$;

6LactD2Nal$^1$-D4ClPhe$^2$-D3Pal$^3$ -Ser$^4$-NMeTyr$^5$-DLys(N-epsilon-Nic)$^6$ -Leu$^7$-Lys(N-epsilon-Isopropyl)$^8$-Pro$^9$-DAla$^{10}$NH$_2$;

5LactGly$^1$-D4ClPhe$^2$-D1Nal$^3$ -Ser$^4$-NMeTyr$^5$-DCit$^6$ -Leu$^7$-Arg$^8$-Pro$^9$-DAla$^{10}$NH$_2$;

5LactD2Nal$^1$-D4ClPhe$^2$-D3Pal$^3$ -Ser$^4$-NMePhe(Atz)$^5$-DLys(Nic)$^6$ -Leu$^7$-Lys(N-epsilon-Isopropyl)$^8$-Pro$^9$-DAla$^{10}$NH$_2$;

5LactD2Nal$^1$-D4ClPhe$^2$-D3Pal$^3$ -Ser$^4$-NMeTyr$^5$-DLys(Atz)$^6$ -Leu$^7$-Lys(N-epsilon-Isopropyl)$^8$-Pro$^9$-DAla$^{10}$NH$_2$;

5LactD2Nal$^1$-D4ClPhe$^2$-D3Pal$^3$ -Ser$^4$-NMeTyr$^5$-DLys-(Nic)$^6$ -Leu$^7$-Lys(N-epsilon-1-hydroxy-isopropyl)$^8$-Pro$^9$-DAla$^{10}$NH$_2$;

5LactD2Nal$^1$-D4ClPhe$^2$-D3Pal$^3$ -Ser$^4$-NMeTyr$^5$-DLys-(Nic)$^6$ -Leu$^7$-Lys(Isp)$^8$-NMeAla$^9$-DAla$^{10}$NH$_2$;

5LactD2Nal$^1$-D4ClPhe$^2$-D3Pal$^3$ -Ser$^4$-Phe(Atz)$^5$-DPhe(Atz)$^6$ -Leu$^7$-Lys(N-epsilon-Isopropyl)$^8$-Pro$^9$-DAla$^{10}$NH$_2$;

5LactD2Nal$^1$-D4ClPhe$^2$-D3Pal$^3$ -Ser$^4$-Tyr$^5$-DHarg(Et$_2$)$^6$ -Leu$^7$-HArg(Et$_2$)$^8$-Pro$^9$-DAla$^{10}$NH$_2$;

5LactD2Nal$^1$-D4ClPhe$^2$-D3Pal$^3$ -Ser$^4$-Tyr$^5$-DLys(Shik)$^6$ -Leu$^7$-Arg$^8$-Pro$^9$-DAla$^{10}$NH$_2$;

5LactD2Nal$^1$-D4ClPhe$^2$-D3Pal$^3$ -Ser$^4$-Tyr$^5$-DLys(Gly-Shik)$^6$ -Leu$^7$-Arg$^8$-Pro$^9$-DAla$^{10}$NH$_2$;

5LactD2Nal$^1$-D4ClPhe$^2$-D3Pal$^3$ -Ser$^4$-Tyr$^5$-DLys(Gly-Shik)$^6$ -Leu$^7$-Harg$^8$-Pro$^9$-DAla$^{10}$NH$_2$;

LHRH Antagonist Activity

Representative compounds of the present invention were evaluated in an in vitro test for LHRH antagonist potency (pA2). The test employed the method detailed in F. Haviv, et al. *J. Med. Chem.*, 32:2340–2344 (1989). The values of pA$_2$ are the negative logarithms of the concentration of the particular antagonist test compound required to shift the response curve produced by the agonist leuprolide to two-fold higher concentration. (Leuprolide is disclosed and claimed in U.S. Pat. No. 4,005,063.) Typically pA$_2$ values of 9.5 or greater are indicative of good LHRH antagonist potency, with values of 10.0 or greater being preferred.

Representative compounds of the present invention were tested by the method described above and the results are presented in Table 1.

TABLE 1

| Example | pA$_2$ |
|---|---|
| 1 | 11.09 |
| 2 | 10.58 |
| 3 | 10.68 |
| 4 | 11.16 |
| 5 | 11.19 |
| 6 | 10.82 |
| 7 | 10.43 |
| 8 | 10.89 |
| 9 | 10.45 |
| 10 | 10.68 |
| 11 | 10.68 |
| 12 | 10.75 |
| 13 | 10.75 |
| 14 | 10.75 |

The compounds of the present invention act as LHRH antagonists and are useful for suppressing levels of gonadotropins and androgens in mammals.

In the practice of the method of this invention an amount of a compound of the invention effective to suppress levels of sex hormones in a mammal, is administered to the host in need of such treatment. These compounds or compositions may be administered by any of a variety of routes depending upon the specific end use, including orally, parenterally (including subcutaneous, intramuscular and intraveneous administration), vaginally (particularly for contraception), rectally, buccally (including sublingually), transdermally or intranasally. The most suitable route in any given case will depend upon the use, particular active ingredient, the subject involved, and the judgment of the medical practitioner. The compound or composition may also be administered by means of slow-release, depot or implant formulations as described more fully herein below.

In general, to modulate levels of sex hormones in male or female mammals for the uses herein above described, it is expedient to administer the active ingredient in amounts between about 0.01 and 10 mg/kg body weight per day, preferably between about 0. 1 and 5.0 mg/kg body weight per day. This administration may be accomplished by a single daily administration, by distribution over several applications or by slow release in order to achieve the most effective results.

The exact dose and regimen for administration of these compounds and compositions will necessarily be dependent upon the needs of the individual subject being treated, the type of treatment, the degree of affliction or need and the judgment of the medical practitioner. In general, parenteral administration requires lower dosage than other methods of administration which are more dependent upon absorption.

A further aspect of the present invention relates to pharmaceutical compositions containing as active ingredient a compound of the present invention which compositions comprise such compound in admixture with a pharmaceutically acceptable, non-toxic carrier. As mentioned above, such compositions may be prepared for use for parenteral (subcutaneous, intramuscular or intraveneous) administration, particularly in the form of liquid solutions or suspensions; for use in vaginal or rectal administration, particularly in semisolid forms such as creams and suppositories; for oral or buccal administration, as particularly in the form of tablets or capsules, or intranasally, particularly in the form of powders, nasal drops or aerosols.

The compositions may conveniently be administered in unit dosage form and may be prepared by any of the methods well-known in the pharmaceutical art, for example as described in Remington's Pharmaceutical Sciences, Mack Publishing Company, Easton, Pa., 1970. Formulations for parenteral administration may contain as common excipients sterile water or saline, polyalkylene glycols such as polyethylene glycol, oils of vegetable origin, hydrogenated naphthalenes and the like. Formulations for inhalation administration may be solid and contain as excipients, for example, lactose, may be aqueous or oily solutions for administration in the form of nasal drops. For buccal administration typical excipients include sugars, calcium stearate, magnesium stearate, pregelatinated starch, and the like.

It is particularly desirable to deliver the compounds of the present invention to the subject over prolonged periods of time, for example, for periods of one week to one year from a single administration. Various slow release, depot or implant dosage forms may be utilized. For example, a dosage form may contain a pharmaceutically acceptable non-toxic salt of a compound of the invention which has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzylethylenediamine or ethylenediamine; or (c) combinations of (a) and (b) e.g. a zinc tannate salt. Additionally, the compounds of the present invention or, preferably, a relatively insoluble salt such as those just described, may be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed or encapsulated in a slow degrading, non-toxic, non-antigenic polymer such as a polylactic acid/polyglycolic acid polymer for example as described in U.S. Pat. No. No. 3,773,919. The compounds of the invention or, preferably, relatively insoluble salts such as those described above may also be formulated in cholesterol matrix pellets, particularly for use in animals. Additional slow release, depot or implant formulations, e.g. liposomes, are well known in the literature. See, for example, Sustained and Controlled Release Druq Delivery Systems, J. R. Robinson ed., Marcel Dekker, Inc., New York, 1978. Particular reference with respect to LHRH type compounds may be found, for example, in U.S. Pat. No. 4,010,125.

Synthesis of the Compounds of the Invention

In general, the compounds of the present invention are synthesized by techniques known to those skilled in the art as, for example, by so-called "solid phase" peptide synthesis or by usual methods of solution phase chemistry. A summary of available solid phase peptide synthetic techniques may be found in J. M. Stewart and J. D. Young, *Solid Phase Peptide Synthesis,* W. H. Freeman Co., San Francisco, 1963 and *J. Meienhofer, Hormonal Proteins and Peptides,* Vol. 2., p. 46, Academic Press (New York), 1973. For classical solution synthesis see G. Schroder and K. Lupke, *The Peptides,* vol. 1, Academic Pres (New York), 1965.

In general, these methods comprise the sequential addition of one or more amino acids or suitably protected amino acids to a growing peptide chain bound to a suitable resin. The starting amino acids are commercially available or, where novel in the compounds of this invention, are synthesized by methods detailed below from readily available starting materials.

Normally, either the amino or carboxyl group of the first amino acid is protected by a suitable protecting group. The protected or derivatized amino acid can then be either attached to an inert solid support (resin) or utilized in solution by adding the next amino acid in the sequence having the complimentary (amino or carboxyl) group suitably protected, under conditions conducive for forming the amide linkage. The protecting group is then removed from this newly added amino acid residue and the next amino acid (suitably protected) is added, and so forth. After all the desired amino acids have been linked in the proper sequence, any remaining protecting groups are removed sequentially or concurrently, and the peptide chain, if synthesized by the solid phase method, is cleaved from the solid support to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing peptides involves solid phase peptide synthesis. In this method of preparing peptides, the alpha-amino function of the amino acids is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are t-butyloxycarbonyl (BOC), benzyloxycarbonyl (Cbz), biphenylisopropyloxycarbonyl, t-amyloxycarbonyl, isobornyloxycarbonyl, (alpha,alpha)-dimethyl-3,5dimethoxybenzyloxycarbonyl, o-nitrophenylsulfenyl, 2-cyano-t-butyloxycarbonyl, 9-fluorenylmethyloxycarbonyl and the like. The t-butyloxycarbonyl ("BOC" or "t-BOC") protecting group is preferred.

Particularly preferred side chain protecting groups are, for side-chain amino groups as in lysine and arginine: nitro, p-toluene-sulfonyl, 4-methoxybenzenesulfonyl, Cbz, BOC and adamantyloxycarbonyl; for tyrosine: benzyl, o-bromobenzyloxycarbonyl, 2,6-dichlorobenzyl, isopropyl, cyclohexyl, cyclopentyl and acetyl; for serine: benzyl and tetrahydropyranyl; for histidine: benzyl, Cbz, p-toluenesulfonyl and 2,4-dinitrophenyl; for tryptophan: formyl.

In the solid phase peptide synthesis method, the C-terminal amino acid is attached to a suitable solid support. Suitable solid supports useful for the above synthesis are those materials which are inert to the reagents and reaction conditions of the stepwise condensation-deprotection reactions, as well as being insoluble in the solvent media used. Suitable solid supports are cloromethylpolystyrenedivinylbenzene polymer, hydroxymethyl-polystyrene-divinylbenzene polymer, and the like. Chloromethyl-polystyrene-1% divinylbenzene polymer is especially preferred. For the special case where the C-terminus of the compound is glycinamide, a particularly useful support is the benzhydrylamino-polystyrenedivinylbenzene polymer described by P. Rivaille, et al, *Helv. Chim. Acta.,* 54, 2772 (1971). The coupling to the chloromethyl polystyrene-divinylbenzene type of resin is made by means of the reaction of the alpha-N-protected amino acid, especially the BOC-amino acid, as its cesium, tetramethylammonium, triethylammonium, 1,5-diazabicyclo-[5.4.0]undec-5-ene, or similar salt. The coupling reaction is accomplished in a solvent such as ethanol, acetonitrile, N,N-dimethylformamide (DMF), and the like, with the chloromethyl resin at an elevated temperature, for example between about 40° and 60° C., for from about 12 to 48 hours. Preferred reagents and reaction conditions involve the coupling of an alpha-N-BOC amino acid cesium salt with the resin in DMF at about 50° C for about 24 hours. The alpha-N-BOC-amino acid is attached to the benzhydrylamine resin by means of N,N'-dicyclohexylcarbodiimide (DCC) or N,N'-diisopropylcarbodiimide (DIC) with or without 1-hydroxybenzotriazole (HOBt), benzotriazol -1-yloxy-tris(dimethylamino)phosphonium-hexafluorophosphate (BOP) or bis(2-oxo-3-oxazolidinyl)phosphine chloride (BOPCl), mediated coupling for from about 1 to about 24 hours, preferably about 12 hours at a temperature of between about 10° and 50° C., most preferably 25° C. in a solvent such as dichloromethane or DMF, preferably dichloromethane. The coupling of the carboxyl group to the N-methyl-Ser(OBzl) attached to the peptide resin requires catalysis by 4-dimethylaminopyridine (DMAP), in addition to the carbodiimide reagent.

The coupling of successive protected amino acids can be carried out in an automatic polypeptide synthesizer as is well known in the art. The removal of the alpha-N-protecting groups may be performed in the presence of, for example, a solution of trifluoroacetic acid in methylene chloride, hydrogen chloride in dioxane, hydrogen chloride in acetic acid, or other strong acid solution, preferably 50% trifluoroacetic acid in dichloromethane at about ambient temperature. Each protected amino acid is preferably introduced in 0.4M concentration and approximately 3.5 molar excess and the coupling may be carried out in dichloromethane, dichloromethane/DMF mixtures, DMF and the like, especially in methylene chloride at about ambient temperature. The coupling agent is normally DCC in dichloromethane but may be N,N'-di-isopropylcarbodiimide (DIC) or other carbodiimide either alone or in the presence of HOBt, N-hydroxysuccinimide, other N-hydroxyimides or oximes. Alternately, protected amino acid active ester (e.g. p-nitrophenyl, pentafluorophenyl and the like) or symmetrical anhydrides may be used.

Synthesis of Intermediates

A. Preparation of 2-(N-2'-pyrrolidinonyl)acetic acid (5Lact-Gly)

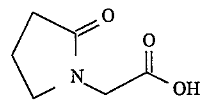

2-Pyrrolidinone (3.28 mL, 43.2 mmol) was added to a solution of NaH (3.31 g 60% in mineral oil, 82.8 mmol) in toluene (50 mL) under nitrogen. The solution was heated to 60° for 1 h. Bromoacetic acid (5.00 g, 36.0 mmol) in toluene (20 mL) was added to the solution and the mixture stirred for 3h at 60°. The mixture was poured into water. The organic layer was extracted with saturated aqueous $NaHCO_3$. The combined aqueous extracts were acidified to pH 2 with 6N HCl and extracted with ethyl acetate. The ethyl acetate extracts were combined dried with anhydrous $MgSO_4$ and concentrated under reduced pressure. The product was obtained as a solid and recrystallized from ethyl acetate-hexane, for a yield of (3.14 g) 61%. MS m/z 144 $(MH)^+$. Anal. Calcd. for $C_6H_9NO_3$: C, 50.34; H, 6.33; N, 9.78. Found C, 50.14; H, 6.20; N, 9.82. Mp. 144–147°.

B. Preparation of 2-(N-2'-pyrrolidinonyl)-2-(R)-(2-naphthylmethyl)acetic acid (5LactD2Nal).

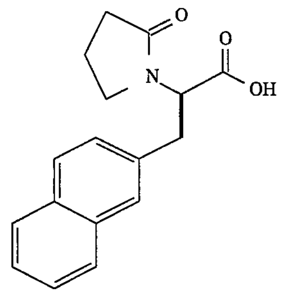

A solution of D-2-Naphthylalanine (5.10 g, 9.23.69 mmol) in THF/H20 (120 mL) was cooled to 0° and the pH adjusted to 9 with 2 M NaOH. 4-Chlorobutyryl chloride (3.72 mL, 33.17 mmol) was added dropwise while maintaining the pH at 9 with 2N NaOH. Upon the completion of the addition of 4-chlorobutyryl chloride, the solution was warmed to room temperature and stirred for 15 min. The reaction was acidified to pH 2-3 (4N HCl) and extracted with chloroform, dried over anhydrous $Na_2SO_4$ and filtered. The chloroform was condensed under reduced pressure to yield a crude product which was used in the next step without further purification. MS m/z 320 $(MH)^+$. A solution of 4-Cl-Butyryl-D-2-Naphthylalanine (7.6 g, 23.7 mmol), in THF (65 mL), was added dropwise to a solution of Nail (60% dispersion, 3.8 g, 95 mmol) in THF (45 mL) at 0° under nitrogen. The reaction mixture was warmed to room temperature and stirred for 24 h, then was quenched with cold 1N $NaHSO_4$ (100 mL) with rapid stirring. The mixture was extracted with chloroform. The organic extracts were dried with $Na_2SO_4$, filtered and concentrated under reduced pressure. The resulting solid was triturated with cold ethyl acetate to yield 2(N- 2'-pyrrolidinonyl)-2-(R)-(2-naphthylmethyl)-acetic acid (5Lact-D2Nal), a white powder; (5.35 g) 80%. MS m/z 284 $(MH)^+$. Anal. Calcd. for $C_{17}H_{17}NO_3$: C, 72.60; H, 6.40; N, 4.94. Found: C, 72.10; H, 6.22; N, 4.94. Optical rotation $[\alpha]^{20}D$–14.3(c 1.0, MeOH).

C. Preparation of 2(-N-piperidinonyl)-2-(R)-(2-naphthylmethyl)acetic acid (6LactD2Nal).

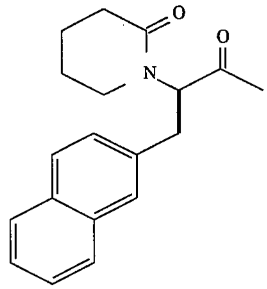

A solution of D-2-Naphthylalanine (5.00 g, 23.22 mmol) in THF/H20 (120 mL) was cooled to 0° and the pH adjusted to 9 with 2 M NaOH. 5-chlorovaleryl chloride (4.2 mL, 32.51 mmol) was added dropwise while maintaining the pH at 9 with 2N NaOH. Upon the completion of the addition of 5-chlorovaleryl chloride, the solution was warmed to room temperature and stirred for 15 min. The reaction was acidified to pH 2-3 (4N HCl) and extracted with chloroform, dried over $Na_2SO_4$ and filtered. The chloroform was condensed under reduced pressure to yield a crude product which was used in the next step without further purification. MS m/z 332.

A solution of 4-Cl-valeryl-D-2-Naphthylalanine (7.6 g, 23.7 mmol), in THF (65 mL), was added dropwise to a solution of Nail (60% dispersion, 3.8 g, 95 mmol) in THF (45 mL) at 0° under nitrogen. The reaction mixture was warmed to room temperature and stirred for 24 h, then was quenched with cold 1N $NaHSO_4$ (100 mL) with rapid stirring. The mixture was extracted with chloroform. The organic extracts were dried with $Na_2SO_4$, filtered and concentrated under reduced pressure. The resulting solid was triturated with cold ethyl acetate to yield 2 (N-piperidinonyl)-2-(R)-(2-naphthylmethyl)acetic acid (6Lact-D2Nal) (5.98g) 85%. MS m/z 298 $(MH)^+$. Anal. Calcd. for $C_{18}H_{19}NO_3$+0.25 $H_2O$: C 71.62; H, 6.51; N, 4.64. Found: C, 71.93, H, 6.52, N, 4.62. Optical rotation $[\alpha]^{20}$ D+94.9 (c 1.0, MeOH).

D. Preparation of 2(N-2'-pyrrolidinonyl)-2-(R)-( 3-quinolinylmethyl)acetic acid (5-LactQual)

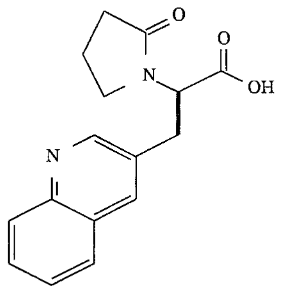

The procedure described in Example (b) is used, but substituting D-3-quinolinylalanine for D-2-naphthylalanine.

E. Preparation of 2-(N-2'-pyrrolidinonyl)- 2-(R)-(4-chlorophenylmethyl)acetic acid (5LactD4ClPhe)

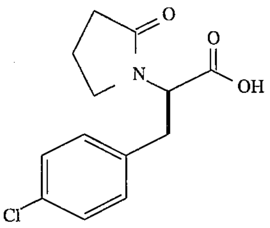

The procedure described in Example (b) is used, but substituting D-4-chlorophenyl-alanine for D-2-naphthylalanine.

F. Preparation of 2-(N-2'-pyrrolidinonyl)- 2-(R)-benzylacetic acid (5LactDPhe)

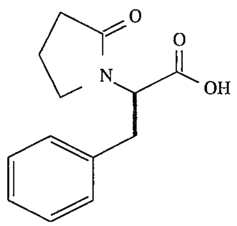

The procedure described in Example (b) is used, but substituting D-phenylalanine for D-2-naphthylalanine.

G. Preparation of 2-(N-2'-pyrrolidinonyl)-2-(R)-( 1-naphthylmethyl)acetic acid (5LactD1Nal)

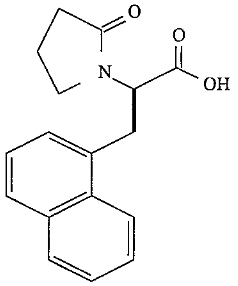

The procedure described in Example (b) is used, but substituting D-1-naphthylalanine for D-2-naphthylalanine.

H. Preparation of 2-(N-2'-piperidinonyl)acetic acid (6Lact-Gly)

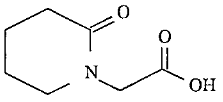

The procedure described in Example (a) is used, but substituting 2-piperidinone for 2-pyrrolidinone.

I. Preparation of 2(-N-piperidinonyl)-2.(R)-(3-quinolinylmethyl)acetic acid 6LactD3Qual)

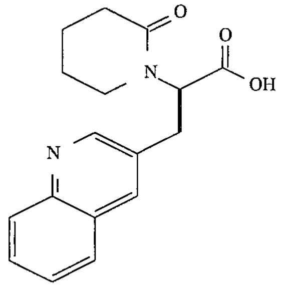

The procedure described in Example (c) is used, but substituting D-3-quinolinylalanine for D-2-naphthylalanine.

J. Preparation of 2(-N-piperidinonyl)-2-(R)-( 4-chlorophenylmethyl)-acetic acid (6LactD4ClPhe)

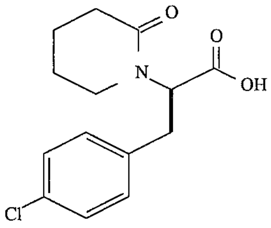

The procedure described in Example (c) is used, but substituting D-4-chlorophenyl-alanine for D-2-naphthylalanine.

K. Preparation of 2-(N-2'-piperidinonyl)-2-(R)-benzylacetic acid (6LactDPhe)

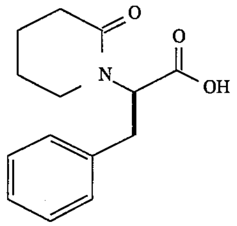

The procedure described in Example (c) is used, but substituting D-phenylalanine for D-2-naphthylalanine.

L. Preparation of 2-(N-2'-piperidinonyl)-2,(R)-( 1-naphthylmethyl)acetic acid (6LactD1Nal)

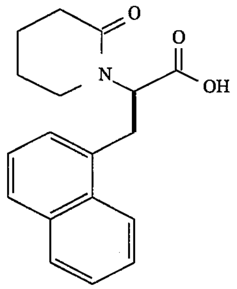

The procedure described in Example (c) is used, but substituting D-1-naphthylalanine for D-2-naphthylalanine.

M. Preparation of 2-($N^g$-caprolactamyl)acetic acid (7LactGly)

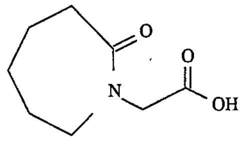

The procedure described in Example (a) is used, but substituting ϵ-caprolactam for 2-pyrrolidinone.

N. Preparation of 2-($N^ϵ$-caprolactamyl)-2-(R)-( 2-naphthylmethyl)-acetic acid (7LactD2Nal)

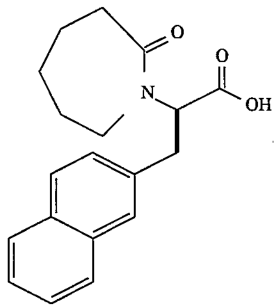

The procedure described in Example (b) is used, but substituting 6-chlorohexanoyl chloride for 4-chlorobutyrl chloride.

O. Preparation of 2-($N^ϵ$-caprolactamyl)-2-(R)-( 3-quinolinylmethyl)-acetic acid (7LactD3Qual)

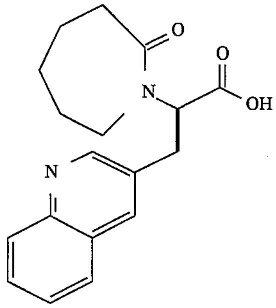

The procedure described in Example (n) is used, but substituting D-3 -quinolinylalanine for D-2-naphthylalanino.

P. Preparation of (2-($N^ϵ$-caprolactamyl)-2-(R)-( 4-chlorophenylmethyl)-acetic acid (7LactD4ClPhe).

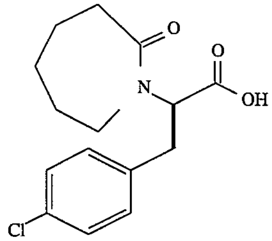

The procedure described in Example (n) is used, but substituting D-4-chlorophenyl-alanine for D-2-naphthylalanine.

Q. Preparation of 2-($N^ϵ$-Caprolactamyl)-2-(R)-benzylacetic acid (7LactDPhe)

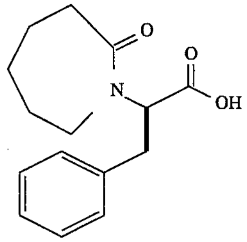

The procedure described in Example (n) is used, but substituting D-phenylalanine for D-2-naphthylalanine.

R. Preparation of 2-($N^ϵ$-caprolactamyl)-2-(R)-(1-naphthylmethyl)-acetic acid

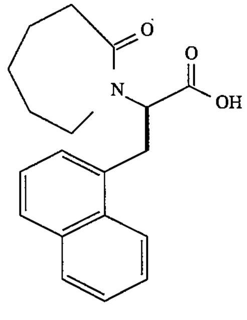

The procedure described in Example (n) is used, but substituting D-1-naphthylalanine for D-2-naphthylalanine.

EXAMPLE 1

Preparation of 5LactD2Nal$^1$-D4ClPhe$^2$-D3Pal$^3$ -Ser$^4$-NMeTyr$^5$-DCit$^6$ -Leu$^7$-Arg$^8$-Pro$^9$-DAla$^{10}$NH$_2$ In the reaction vessel of a Milligen-Biosearch 9500 peptide synthesizer was placed 1 g (0.6 mmol) of D-Ala-NH-resin (4-methyl-benzhydrylamine resin). Amino acids were added sequentially according to the following synthetic cycle:

1. Deblocking, to remove the t-BOC group from the alpha-amino function of the peptide, was carried out using a solution of 45% trifluoroacetic acid (TFA), 2.5% anisole, 2.0% dimethyl phosphite, and 50.5% methylene chloride. The resin was prewashed with the deblocking solution for one minute and then the deblocking reaction is run for 20 minutes.
2. Base wash, to remove and neutralize the TFA used for deprotection, was carried out using a solution of 10% N,N'-diisopropylethylamine in methylene chloride. The resin was washed with base three times for one minute each time after a deblocking step.
3. Coupling reaction was carried out using a 3-fold molar excess of 0.3 M DMF solution of a t-BOC protected amino acid derivative along with a 3-fold molar excess of 0.3 M methylene chloride solution of diisopropylcarbodiimide as activator. The activated amino acid is then coupled to the free alpha amino group of the peptide-resin. The reaction time is as described in the synthesis protocol.
4. Wash, each reaction step was followed by three washes of one minute each: one of methylene chloride, one of (1:1) methylene chloride/DMF, and one of DMF.

Synthesis Protocol

The protected amino acids were coupled to the resin according the following order, number, and duration of couplings:

Amino Acid Coupling 1. BOC-Pro two-1 h 2. BOC-Arg(Tos) two-1h 3. BOC -Leu two-1 h 4. BOC-DCit two-1h 5. BOC-NMe-Tyr(O-2,6-diCl-Bzl) two-1h 6. BOC-Ser(OBzl) two-1h 7. BOC-D-3Pal two-6h 8. BOC-D-4ClPhe two-2h 9. 5LactD2Nal two-4h Upon completion of the synthesis the peptide-resin was then dried overnight over $P_2O_5$ under vacuum and then treated with dry HF in the presence of anisole at 0° C. for 1 h to cleave the peptide from the resin. The excess of reagent was removed in vacuo. The resin was washed first with ether, then stirred at room temperature with a solution of (1:1:0.1) water/acetonitrile/acetic acid (50 ml) for 15 minutes, and filtered. The filtrate was lyophilized to give the crude peptide as a fluffy powder. This was purified by HPLC using a (25×2.5 cm) Dynamax C-18 column (8 micron) with solvent mixtures varying in a gradient ranging from 89% $H_2O$/11% $CH_3CN$/0.1% TFA over a period of 20 minutes. The UV detector was set at 260 nM. The product is eluted as a single peak, collected and lyophilized to give pure 5LactD2Nal-D4ClPhe-D3Pal-Ser-NMeTyr-DCit-Leu-Arg-Pro-DAlaNH$_2$ as the trifluoroacetate salt; $R_t$=20.70 min; FAB Mass Spec. m/e 1470 (M+H)$^+$. Amino Acid Anal: 1.01 Ala; 1.01 Pro; 0.97 Arg; 1.01 Leu; 0.97 Cit; 0.96 NMeTyr; 0.53 Ser; 1.00 D3Pal; 1.06 D4ClPhe.

EXAMPLE 2

Preparation of 5LactD2Nal$^1$-D4ClPhe$^2$-D3Pal$^3$ -Ser$^4$-NMeTyr$^5$-DLys(N-epsilon-Shik)$^6$ -Leu$_7$-Arg$^8$-Pro$^9$-DAla$^{10}$NH$_2$ The procedure described in Example 1 was used with the substitution of BOC-D-Lys(N-epsilon-FMOC) for DCit using two 1 hr coupling. Upon completion of the synthesis the resin was treated with 30% piperdine in DMF solution for 4 to 24 h to remove the FMOC protecting group. After several washes with methylene chloride the peptide-resin is coupled with shikimic acid with the two-4h protocol. The resin was treated as in example 1. The crude peptide was purified by HPLC to yield 5LactD2Nal$^1$-D4ClPhe$^2$-D3Pal$^3$ -Ser$^4$-NMeTyr$^5$-DLys(N-epsilon-Shik)$^6$ -Leu$^7$-Arg$^5$-Pro$^9$-DAla$^{10}$NH$_2$ as the trifluoroacetate salt; $R_t$=19.39 min; FAB Mass Spec. m/e 1597 (M+H)$^+$. Amino Acid Anal: 1.01 Ala; 0.99 Pro; 0.97 Arg; 0.99 Leu; 1.02 Lys; 1.51 NMeTyr; 0.49 Ser; 0.96 D3Pal; 1.01 D4ClPhe.

EXAMPLE 3

Preparation of 5LactD2Nal$^1$-D4ClPhe$^2$-D3Pal$^3$ -Ser$^4$-NMeTyr$^5$-DLys(N-epsilon-Gly-Shik)$^6$ -Leu$^7$-Arg$^8$-Pro$^9$-DAla$^{10}$NH$_2$ The procedure described in Example 2 was used except that after the completion of the synthesis the peptide-resin was treated with 30% piperdine to remove the Fmoc group, then was washed several times with methylene chloride. The peptide-resin is coupled first with BOC-Gly and then with shikimic acid using the two-2h protocol. The peptide was cleaved from the resin using the procedure described in Example 1. The crude peptide was purified by HPLC to yield 5LactD2Nal$^1$-D4ClPhe$^2$-D3Pal$^3$ -Ser$^4$-NMeTyr$^5$-DLys(N-epsilon-Gly-Shik)$^6$ -Leu$^7$-Arg$^8$-Pro$^9$-DAla$^{10}$NH$_2$ as the trifluoroacetate salt; $R_t$=19.25 min; FAB Mass Spec. m/e 1654 (M+H)$^+$. Amino Acid Anal: 1.01 Ala; 0.97 Pro; 0.97 Arg; 0.98 Leu; 1.02 Lys; 1.52 NMeTyr; 0.52 Ser; 0.94 D3Pal; 0.99 D4ClPhe; 1.03 Gly.

EXAMPLE 4

Preparation of 5LactD2Nal$^1$-D4ClPhe$^2$-D3Pal$^3$ -Ser$^4$-NMeTyr$^5$-DLys(N-epsilon-Shik)$^6$ -Leu$^7$-Harg$^8$-Pro$^9$-DAla$^{10}$NH$_2$ The procedure and the protocol described in Example 2 was used except for the substitution of BOC-Harg($NO_2$) for BOC-Arg(Tos). After workup the crude peptide was purified by HPLC to yield 5LactD2Nal$^1$-D4ClPhe$^2$-D3Pal$^3$ -Ser$^4$-NMeTyr$^5$-DLys(N-epsilon-Shik)$^6$ -Leu$^7$-Harg$^8$-Pro$^9$-DAla$^{10}$NH$_2$ as the trifluoroacetate salt; $R_t$=18.94 min; FAB Mass spec. m/e 1612 (M+H$^+$. Amino Acid. Anal: 1.00 Ala; 1.01 Pro; 1.00 Leu; 0.99 Lys; 1.10 NMeTyr; 0.43 Ser; 1.15 D3Pal; 0.90 D4ClPhe.

EXAMPLE 5

Preparation of 5LactD2Nal$^1$-D4ClPhe$^2$-D3Pal$^3$ -Ser$^4$-NMeTyr$^5$-DLys(N-epsilon-Gly-Shik)$^6$ -Leu$_7$-Harg$^8$-Pro$^9$-DAla$^{10}$NH$_2$ The procedure and the protocol described in Example 3 was used except for the substitution of BOC-Harg($NO_2$) for BOC-Arg(Tos). After workup the crude peptide was purified by HPLC to yield 5LactD2Nal$^1$-D4ClPhe$^2$-D3Pal$^3$ -Ser$^4$-NMeTyr$^5$-DLys(N-epsilon-Gly-Shik)$^6$ -Leu$^7$-Harg$^8$-Pro$^9$-DAla$^{10}$NH$_2$ as the trifluoroacetate salt; $R_t$=18.94 min; FAB Mass spec. m/e 1669 (M+H)$^+$. Amino Acid Anal: 1.00 Ala; 1.00 Pro; 0.97 Gly; 1.01 Leu; 1.01 Lys; 1.07 NMeTyr; 0.45 Ser; 1.14 D3Pal; 0.89 D4ClPhe.

EXAMPLE 6

Preparation of 5LactD2Nal$^1$-D4ClPhe$^2$-D3Pal$^3$ -Ser$^4$-Tyr$^5$-DCit$^6$ -Leu$^7$-Arg$^8$-Pro$^9$-DAla$^{10}$NH$_2$ The procedure and the protocol described in Example 1 was used except for the substitution of BOC-Tyr(O-2,6-diCl-Bzl) for BOC-NMe-Tyr(O-2,6-diCl-Bzl). After workup the crude peptide was purified by HPLC to yield $5LactD2Nal^1$-$D4ClPhe^2$-$D3Pal^3$ -$Ser^4$-$Tyr^5$-$DCit^6$ -$Leu^7$-$Arg^8$-$Pro^9$-$DAla^{10}NH_2$ as the trifluoroaceate salt; $R_t$=18.95 min; FAB Mass spec. m/e 1599 $(M+H)^+$. Amino Acid Anal: 0.97 Ala; 1.01 Pro; 0.97 Arg; 1.03 Leu; 1.08 Cit; 1.01 Tyr; 0.48 Ser; 1.12 D3Pal; 1.27 D4ClPhe.

EXAMPLE 7

Preparation of $5LactD2Nal^1$-$D4ClPhe^2$-$D3Pal^3$ -$Ser^4$-$NMeTyr^5$-DLys(N-epsilon-$Nic)^6$ -$Leu^7$-Lys(N-epsilon-$Isopropyl)^8$-$Pro^9$-$DAla^{10}NH_2$ The procedure and the protocol described in Example 1 was used except for the substitutions of BOC-D-Lys(N-epsilon-FMOC) for Boc-DCit and BOC-Lys(N-epsilon-Cbz, isopropyl) for Arg(Tos). Upon completion of the synthesis the resin was treated with 30% piperidine in DMF solution for 4 to 24 h to remove the FMOC protecting group. After several washes with methylene chloride the peptide-resin was coupled with nicotinic acid with the two-2 h protocol. The crude peptide was purified by HPLC to yield $5LactD2Nal^1$-$D4ClPhe^2$-$D3Pal^3$ -$Ser^4$-$NMeTyr^5$-DLys(N-epsilon-$Nic)^6$ -$Leu^7$-Lys(N-epsilon-$Isopropyl)^8$-$Pro^9$ -$DAla^{10}NH_2$ as the trifluoroacetate salt; $R_t$=19.78; FAB Mass spec. m/e 1560 $(M+H)^+$. Amino Acid Anal: 0.99 Ala; 1.00 Pro; 0.77 Lys(Isp); 1.00 Leu; 1.00 Lys; 1.06 NMeTyr; 0.43 Set; 0.94 D3Pal; 0.86 D4ClPhe.

EXAMPLE 8

Preparation of $6LactD2Nal^1$-$D4ClPhe^2$-$D3Pal^3$ -$Ser^4$-$NMeTyr^5$-DLys(N-epsilon-$Shik)^6$ -$Leu^7$-$Arg^8$-$Pro^9$-$DAla^{10}NH_2$ The procedure described in Example 2 was used except for the substitution of 6LactD2Nal for 5LactD2Nal. After workup the crude peptide was purified by HPLC to yield $6LactD2Nal^1$-$D4ClPhe^2$-$D3Pal^3$ -$Ser^4$-$NMeTyr^5$-DLys(N-epsilon-$Shik)^6$ -$Leu^7$-$Arg^8$-$Pro^9$-$DAla^{10}NH_2$ as the trifluoroacetate salt; $R_t$=21.04 min; FAB Mass spec. m/e 1611 $(M+H)^+$. Amino Acid Anal: 0.98 Ala; 1.01 Pro; 0.97 Arg; 1.02 Leu; 1.00 Lys; 1.21 NMeTyr; 0.43 Ser; 1.13 D3Pal; 1.24 D4ClPhe.

EXAMPLE 9

Preparation of $6LactD2Nal^1$-$D4ClPhe^2$-$D3Pal^3$ -$Ser^4$-$NMeTyr^5$-DLys(N-epsilon-Gly-$Shik)^6$ -$Leu^7$-$Arg^8$-$Pro^9$-$DAla^{10}NH_2$ The procedure described in Example 3 was used except for the substitution of 6LactD2Nal for 5LactD2Nal. After workup the crude peptide was purified by HPLC to yield $6LactD2Nal^1$-$D4ClPhe^2$-$D3Pal^3$ -$Ser^4$-$NMeTyr^5$-DLys(N-epsilon-Gly-$Shik)^6$ -$Leu^7$-$Arg^8$-$Pro^9$-$DAla^{10}NH_2$ as the trifluoroacetate salt; $R_t$=20.63 min; FAB Mass spec. m/e 1668 $(M+H)^+$. Amino Acid Anal: 1.00 Ala; 1.02 Pro; 0.97 Arg; 1.04 Leu; 1.02 Lys; 1.20 NMeTyr; 0.43 Ser; 1.14 D3Pal; 1.25 D4ClPhe; 0.96 Gly.

EXAMPLE 10

Preparation of $6LactD2Nal^1$-$D4ClPhe^2$-$D3Pal^3$ -$Ser^4$-$NMeTyr^5$-DLys(N-epsilon-$Shik)^6$ -$Leu^7$-$Harg^8$-$Pro^9$-$DAla^{10}NH_2$ The procedure described in Example 4 was used except for the substitution of 6LactD2Nal for 5LactD2Nal. After workup the crude peptide was purified by HPLC to yield $6LactD2Nal^1$-D4Cl $Phe^2$-$D3Pal^3$ -$Ser^4$-$NMeTyr^5$-DLys(N-epsilon-$Shik)^6$ -$Leu^7$-$Harg^8$-$Pro^9$-$DAla^{10}NH_2$ as the trifluoroacetate salt; $R_t$=21.20 min; FAB Mass spec. m/e 1625 $(M+H)^+$. Amino Acid Anal: 0.97 Ala; 1.00 Pro; 1.01 Leu; 1.02 Lys; 1.20 NMeTyr; 0.46 Set; 1.12 D3Pal; 1.22 D4ClPhe.

EXAMPLE 11

Preparation of $6LactD2Nal^1$-$D4ClPhe^2$-$D3Pal^3$ -$Ser^4$-$NMeTyr^5$-DLys(N-epsilon-Gly-$Shik)^6$ -$Leu^7$-$Harg^8$-$Pro^9$-$DAla^{10}NH_2$ The procedure described in Example 5 was used except for the substitution of 6LactD2Nal for 5LactD2Nal. After workup the crude peptide was purified by HPLC to yield $6LactD2Nal^1$-$D4ClPhe^2$-$D3Pal^3$ -$Ser^4$-$NMeTyr^5$-DLys(N-epsilon-Gly-$Shik)^6$ -$Leu^7$-$Harg^8$-$Pro^9$-$DAla^{10}NH_2$ as the trifluoroacetate salt; $R_t$=21.19 min; FAB Mass spec. m/e 1682 $(M+H)^+$. Amino Acid Anal: 0.99 Ala; 0.99 Pro; 0.98 Gly; 1.01Leu; 1.03 Lys; 1.17 NMeTyr; 0.45 Ser; 1.12 D3Pal; 1.24 D4ClPhe.

EXAMPLE 12

Preparation of $5LactD2Nal^1$-$D4ClPhe^2$-$D3Pal^3$ -$Ser^4$-$Tyr^5$-$DHcit^6$ -$Leu^7$-$Lys(isp)^8$-$Pro^9$-$DAla^{10}NH_2$ The procedure described in Example 6 was used except for the substitutions of DHcit for DCit, and Lys(N-epsilon-Cbz,isopropyl) for Arg(Tos). After workup the crude peptide was purified by HPLC to yield $5LactD2Nal^1$-$D4ClPhe^2$-$D3Pal^3$ -$Ser^4$-$Tyr^5$-$DHcit^6$ -$Leu^7$-$Lys(isp)^8$-$Pro^9$-$DAla^{10}NH_2$ as the trifluoroacetate salt; $R_t$=20.19 min; FAB Mass spec. m/e 1484 $(M+H)^+$. Amino Acid Anal: 0.98 Ala; 1.00 Pro; 0.62 Lys(Isp); 1.03 Leu; 0.99 Lys; 1.01 Tyr; 0.47 Ser; 1.12 D3Pal; 1.23 D4ClPhe.

EXAMPLE 13

Preparation of $6LactD2Nal^1$-$D4ClPhe^2$-$D3Pal^3$ -$Ser^4$-$NMeTyr^5$-DLys(N-epsilon-$Nic)^6$ -$Leu^7$-Lys(N-epsilon-$Isopropyl)^8$-$Pro^9$-$DAla^{10}NH_2$ The procedure described in Example 7 was used except for the substitution of 6LactD2Nal for 5LactD2Nal. After workup the crude peptide was purified by HPLC to yield $6LactD2Nal^1$-D4Cl $Phe^2$-$D3Pal^3$ -$Ser^4$-$NMeTyr^5$-DLys(N-epsilon-$Nic)^6$ -$Leu^7$-Lys(N-epsilon-$Isopropyl)^8$-$Pro^9$-$DAla^{10}NH_2$ as the trifluroacetate salt; $R_t$=22.06 min; FAB Mass spec. m/e 1574 $(M+H)^+$. Amino Acid Anal: 1.00 Ala; 0.97 Pro; 0.75 Lys(isp); 1.01 Leu; 1.01Lys; 1.01 NMeTyr; 0.45 Ser; 0.94 D3Pal; 0.89 D4ClPhe.

EXAMPLE 14

Preparation of $5LactGly^1$-$D4ClPhe^2$-$D1Nal^3$ -$Ser^4$-$NMeTyr^5$-$DCit^6$ -$Leu^7$-$Arg^8$-$Pro^9$-$DAla^{10}NH_2$ The procedure and the protocol described in Example 1 was used except for the substitutions of 5LactGly for 5LactD2Nal and BocD1Nal for D3Pal. After workup the crude peptide was purified by HPLC to yield $5LactGly^1$-$D4ClPhe^2$-$D1Nal^3$ -$Ser^4$-$NMeTyr^5$-$DCit^6$ -$Leu^7$-$Arg^8$-$Pro^9$-$DAla^{10}NH_2$ as the trifluroacetate salt; $R_t$=17.45 min; FAB Mass spec. m/e 1380 $(M+H)^+$. Amino Acid Anal: 0.98 Ala; 1.04 Pro; 0.98 Arg; 1.00 Leu; 0.95 Cit; 0.94 NMeTyr; 0.44 Ser; 1.06 D4ClPhe.

EXAMPLE 15

The procedure described in Example 7 is used, but substituting the appropriate groups for 2(N-pyrrolidinone)-2-(R)-(2-naphthylmethyl)-acetic acid (5LactD2Nal), after work-up and HPLC purification the following compounds are obtained as the trifluoroacetate salt:

(a) 5LactGly$^1$-D4ClPhe$^2$-D3Pal$^3$ -Ser$^4$-NMeTyr$^5$-DLys(Nic)$^6$ -Leu$_7$-Lys(N-epsilon-Isopropyl)$^8$-Pro$^9$-DAla$^{10}$NH$_2$
(b) 5LacD3Qal$^1$-D4ClPhe$^2$-D3Pal$^3$ -Ser$^4$-NMeTyr$^5$-DLys(Nic)$^6$ -Leu$_7$-Lys(N-epsilon-Isopropyl)$^8$-Pro$^9$-DAla$^{10}$NH$_2$
(c) 5LactD4ClPhe$^1$-D4ClPhe$^2$-D3Pal$^3$ -Ser$^4$-NMeTyr$^5$-DLys(Nic)$^6$ -Leu$^7$-Lys(N-epsilon-Isopropyl)$^8$-Pro$^9$-DAla$^{10}$NH$_2$
(d) 5LactDPhe$^1$-D4ClPhe$^2$-D3Pal$^3$ -Ser$^4$-NMeTyr$^5$-DLys(Nic)$^6$ -Leu$_7$-Lys(N-epsilon-Isopropyl)$^8$-Pro$^9$-DAla$^{10}$NH$_2$
(e) 5LactD1Nal$^1$-D4ClPhe$^2$-D3Pal$^3$ -Ser$^4$-NMeTyr$^5$-DLys(Nic)$^6$ -Leu$_7$-Lys(N-epsilon-Isopropyl)$^8$-Pro$^9$-DAla$^{10}$NH$_2$
(g) 6LactGly$^1$-D4ClPhe$^2$-D3Pal$^3$ -Ser$^4$-NMeTyr$^5$-DLys(Nic)$^6$ -Leu$_7$-Lys(N-epsilon-Isopropyl)$^8$-Pro$^9$-DAla$^{10}$NH$_2$
(h) 6LactD3Qal$^1$-D4ClPhe$^2$-D3Pal$^3$ -Ser$^4$-NMeTyr$^5$-DLys(Nic)$^6$ -Leu$_7$-Lys(N-epsilon-Isopropyl)$^8$-Pro$^9$-DAla$^{10}$NH$_2$
(i) 6LactD4ClPhe$^1$-D4ClPhe$^2$-D3Pal$^3$ -Ser$^4$-NMeTyr$^5$-DLys(Nic)$^6$ -Leu$_7$-Lys(N-epsilon-Isopropyl)$^8$-Pro$^9$-DAla$^{10}$NH$_2$
(j) 6LactDPhe$^1$-D4ClPhe$^2$-D3Pal$^3$ -Ser$^4$-NMeTyr$^5$-DLys(Nic)$^6$ -Leu$_7$-Lys(N-epsilon-Isopropyl)$^8$-Pro$^9$-DAla$^{10}$NH$_2$
(k) 6LactD1Nal$^1$-D4ClPhe$^2$-D3Pal$^3$ -Ser$^4$-NMeTyr$^5$-DLys(Nic)$^6$ -Leu$_7$-Lys(N-epsilon-Isopropyl)$^8$-Pro$^9$-DAla$^{10}$NH$_2$
(l) 7LactGly$^1$-D4ClPhe$^2$-D3Pal$^3$ -Ser$^4$-NMeTyr$^5$-DLys(Nic)$^6$ -Leu$_7$-Lys(N-epsilon-Isopropyl)$^8$-Pro$^9$-DAla$^{10}$NH$_2$
(m) 7LactD2Nal$^1$-D4ClPhe$^2$-D3Pal$^3$ -Ser$^4$-NMeTyr$^5$-DLys(Nic)$^6$ -Leu$_7$-Lys(N-epsilon-Isopropyl)$^8$-Pro$^9$-DAla$^{10}$NH$_2$
(n) 7LactD3Qal$^1$-D4ClPhe$^2$-D3Pal$^3$ -Ser$^4$-NMeTyr$^5$-DLys(Nic)$^6$ -Leu$_7$-Lys(N-epsilon-Isopropyl)$^8$-Pro$^9$-DAla$^{10}$NH$_2$
(o) 7LactD4ClPhe$^1$-D4ClPhe$^2$-D3Pal$^3$ -Ser$^4$-NMeTyr$^5$-DLys(Nic)$^6$ -Leu$_7$-Lys(N-epsilon-Isopropyl)$^8$-Pro$^9$-DAla$^{10}$NH$_2$
(p) 7LactDPhe$^1$-D4ClPhe$^2$-D3Pal$^3$ -Ser$^4$-NMeTyr$^5$-DLys(Nic)$^6$ -Leu$_7$-Lys(N-epsilon-Isopropyl)$^8$-Pro$^9$-DAla$^{10}$NH$_2$
(q) 7LactD1Nal$^1$-D4ClPhe$^2$-D3Pal$^3$ -Ser$^4$-NMeTyr$^5$-DLys(Nic)$^6$ -Leu$_7$-Lys(N-epsilon-Isopropyl)$^8$-Pro$^9$-DAla$^{10}$NH$_2$

EXAMPLE 16

The procedure described in Example 7 is used, but substituting the appropriate BOC-amino acids for BOC-D4ClPhe, after work-up and HPLC purification the following compounds are obtained as the trifluoroacetate salt:

(a) 5LactD2Nal$^1$-DPhe$^2$-D3Pal$^3$ -Ser$^4$-NMeTyr$^5$-DLys(Nic)$^6$ -Leu$_7$-Lys(N-epsilon-Isopropyl)$^8$-Pro$^9$-DAla$^{10}$NH$_2$
(b) 5LactD2Nal$^1$-D2Nal$^2$-D3Pal$^3$ -Ser$^4$-NMeTyr$^5$-DLys(Nic)$^6$ -Leu$_7$-Lys(N-epsilon-Isopropyl)$^8$-Pro$^9$-DAla$^{10}$NH$_2$
(c) 5LactD2Nal$^1$-D4FPhe$^2$-D3Pal$^3$ -Ser$^4$-NMeTyr$^5$-DLys(Nic)$^6$ -Leu$_7$-Lys(N-epsilon-Isopropyl)$^8$-Pro$^9$-DAla$^{10}$NH$_2$

EXAMPLE 17

The procedure described in Example 7 is used, but substituting the appropriate BOC-amino acids for BOC-D3Pal, after work-up and HPLC purification the following compounds are obtained as the trifluoroacetate salt:

(a) 5LactD2Nal$^1$-D4ClPhe$^2$-Gly$^3$ -Ser$^4$-NMeTyr$^5$-DLys(Nic)$^6$ -Leu$_7$-Lys(N-epsilon-Isopropyl)$^8$-Pro$^9$-DAla$^{10}$NH$_2$
(b) 5LactD2Nal$^1$-D4ClPhe$^2$-D1Nal$^3$ -Ser$^4$-NMeTyr$^5$-DLys(Nic)$^6$ -Leu$_7$-Lys(N-epsilon-Isopropyl)$^8$-Pro$^9$-DAla$^{10}$NH$_2$
(c) 5LactD2Nal$^1$-D4ClPhe$^2$-DAla$^3$ -Ser$^4$-NMeTyr$^5$-DLys(Nic)$^6$ -Leu$_7$-Lys(N-epsilon-Isopropyl)$^8$-Pro$^9$-DAla$^{10}$NH$_2$
(d) 5LactD2Nal$^1$-D4ClPhe$^2$-DTrp3 -Ser$^4$-NMeTyr$^5$-DLys(Nic)$^6$ -Leu$_7$-Lys(N-epsilon-Isopropyl)$^8$-Pro$^9$-DAla$^{10}$NH$_2$
(e) 5LactD2Nal$^1$-D4ClPhe$^2$-D3Bal$^3$ -Ser$^4$-NMeTyr$^5$-DLys(Nic)$^6$ -Leu$_7$-Lys(N-epsilon-Isopropyl)$^8$-Pro$^9$-DAla$^{10}$NH$_2$

EXAMPLE 18

The procedure described in Example 7 is used, but substituting the appropriate BOC-amino acids for BOC-Ser(OBzl), after work-up and HPLC purification the following compounds are obtained as the trifluoroacetate salt:

(a) 5LactD2Nal$^1$-D4ClPhe$^2$-D3Pal$^3$ -NMeSer$^4$-NMeTyr$^5$-DLys(Nic)$^6$ -Leu$^7$-Lys(N-epsilon-Isopropyl)$^8$-Pro$^9$-DAla$^{10}$NH$_2$
(b) 5LactD2Nal$^1$-D4ClPhe$^2$-D3Pal$^3$ -Gly$^4$-NMeTyr$^5$-DLys(Nic)$^6$ -Leu$_7$-Lys(N-epsilon-Isopropyl)$^8$-Pro$^9$-DAla$^{10}$NH$_2$
(c) 5LactD2Nal$^1$-D4ClPhe$^2$-D3Pal$^3$ -Thr$^4$-NMeTyr$^5$-DLys(Nic)$^6$ -Leu$_7$-Lys(N-epsilon-Isopropyl)$^8$-Pro$^9$-DAla$^{10}$NH$_2$

EXAMPLE 19

The procedure described in Example 7 is used, but substituting the appropriate BOC-amino acids for BOC-NMeTyr(O-2,6-diCl-Bzl), after work-up and HPLC purification the following compounds are obtained as the trifluoroacetate salt:

(a) 5LactD2Nal$^1$-D4ClPhe$^2$-D3Pal$^3$ -Ser$^4$-Tyr$^5$-DLys(Nic)$^6$ -Leu$_7$-Lys(N-epsilon-Isopropyl)$^8$-Pro$^9$-DAla$^{10}$NH$_2$
(b) 5LactD2Nal$^1$-D4ClPhe$^2$-D3Pal$^3$ -Ser$^4$-Lys(Nic)$^5$-DLys(Nic)$^6$ -Leu$_7$-Lys(N-epsilon-Isopropyl)$^8$-Pro$^9$-DAla$^{10}$NH$_2$
(c) 5LactD2Nal$^1$-D4ClPhe$^2$-D3Pal$^3$ -Ser$^4$-Lys(Pic)$^5$-DLys(Nic)$^6$ -Leu$_7$-Lys(N-epsilon-Isopropyl)$^8$-Pro$^9$-DAla$^{10}$NH$_2$
(d) 5LactD2Nal$^1$-D4ClPhe$^2$-D3Pal$^3$ -Ser$^4$-NMePhe$^5$-DLys(Nic)$^6$ -Leu$_7$-Lys(N-epsilon-Isopropyl)$^8$-Pro$^9$-DAla$^{10}$NH$_2$

EXAMPLE 20

Preparation of 5LactD2Nal$^1$-D4ClPhe$^2$-D3Pal$^3$ -Ser$^4$-Phe(Atz)$^5$-DLys(Nic)$^6$ -Leu$_7$-Lys(N-epsilon-Isopropyl)$^8$-Pro$^9$-DAla$^{10}$NH$_2$ The procedure described in Example 7 is used, but substituting BOC-Phe( 4-NH-FMOC) for BOC-NMeTyr(O-2,6-diCl-Bzl). Upon completion of the synthesis the resin is treated with 30% piperidine in DMF solution for 4 to 24 h to remove the FMOC protecting group. The resin is washed three times each with (1:1) DCM/DMF and DCM, then treated with a solution of diphenyl cyanocarbonimidate (0.43 g in 15 mL DMF), and the mixture bubbled for 16 h. The resin is washed three times each with (1:1) DCM/DMF, MeOH, and DCM, then treated with neat hydrazine (10 mL) for 8 hours. The resin is again washed three times each with (1:1) DCM/DMF, MeOH, and DCM, and dried in vacuo overnight over $P_2O_5$. After HF treatment and HPLC purification 5LactD2Nal$^1$-D4ClPhe$^2$-D3Pal$^3$ -Ser$^4$-Phe(Atz)$^5$-DLys(Nic)$^6$ -Leu$^7$-Lys(N-epsilon-Isopropyl)$^8$-Pro$^9$-DAla$^{10}$NH$_2$ is obtained as the trifluoroacetate salt.

EXAMPLE 21

Preparation of 5LactD2Nal$^1$-D4ClPhe$^2$-D3Pal$^3$ -Ser$^4$-NMePhe(Atz)$^5$-DLys(Nic)$^6$ -Leu$_7$-Lys(N-epsilon-Isopropyl)$^8$-Pro$^9$-DAla$^{10}$NH$_2$ The procedure described in Example 20 is used, but substituting BOC-NMePhe(NH-FMOC) for BOC-Phe(N-H-FMOC), after work-up and HPLC purification 5LactD2Nal$^1$-D4ClPhe$^2$-D3Pal$^3$ -Ser$^4$-NMePhe(Atz)$^5$-DLys(Nic)$^6$ -Leu$^7$-Lys(N-epsilon-Isopropyl)$^8$-Pro$^9$-DAla$^{10}$NH$_2$ is obtained as the trifluoroacetate salt.

EXAMPLE 22

The procedure described in Example 7 is used, but substituting the appropriate BOC-amino acids for BOC-DLys(Nic), after work-up and HPLC purification the following compounds are obtained as the trifluoroacetate salt:

(a) 5LactD2Nal$^1$-D4ClPhe$^2$-D3Pal$^3$-Ser$^4$-NMeTyr$^5$-DCit$^6$-Leu$^7$-Lys(N-epsilon-Isopropyl)$^8$-Pro$^9$-DAla$^{10}$NH$_2$ (b) 5LactD2Nal$^1$-D4ClPhe$^2$-D3Pal$^3$-Ser$^4$-NMeTyr$^5$-DHcit$^6$-Leu$^7$-Lys(N-epsilon-Isopropyl)$^8$-Pro$^9$-DAla$^{10}$NH$_2$ (c) 5LactD2Nal$^1$-D4ClPhe$^2$-D3Pal$^3$-Ser$^4$-NMeTyr$^5$-DArg$^6$-Leu$^7$-Lys(N-epsilon-Isopropyl)$^8$-Pro$^9$-DAla$^{10}$NH$_2$ (d) 5LactD2Nal$^1$-D4ClPhe$^2$-D3Pal$^3$-Ser$^4$-NMeTyr$^5$-DHarg$^6$-Leu$^7$-Lys(N-epsilon-Isopropyl)$^8$-Pro$^9$-DAla$^{10}$NH$_2$ (e) 5LactD2Nal$^1$-D4ClPhe$^2$-D3Pal$^3$-Ser$^4$-NMeTyr$^5$-DHarg(Et$_2$)$^6$-Leu$^7$-Lys(N-epsilon-Isopropyl)$^8$-Pro$^9$-DAla$^{10}$NH$_2$

EXAMPLE 23

The procedure described in Example 7 is used, but substituting BOC-DLys(N-epsilon-FMOC) for BOC-DLys-(Nic). Upon completion of the synthesis the resin is treated with 30% piperidine in DMF solution for 4 to 24 h to remove the FMOC protecting group. After several washes with methylene chloride the peptide-resin is coupled with the appropriate acids to provide after work-up and HPLC purification the following compounds as the trifluoroacetate salt:

(a) 5LactD2Nal$_1$-D4ClPhe$^2$-D3Pal$^3$-Ser$^4$-NMeTyr$^5$-DLys(Shik)$_6$-Leu$^7$-Lys(N-epsilon-Isopropyl)$^8$-Pro$^9$-DAla$^{10}$NH$_2$ (b) 5LactD2Nal$_1$-D4ClPhe$^2$-D3Pal$^3$-Ser$^4$-NMeTyr$^5$-DLys(Pyz)$_6$-Leu$^7$-Lys(N-epsilon-Isopropyl)$^8$-Pro$^9$-DAla$^{10}$NH$_2$

EXAMPLE 24

The procedure described in Example 23 is used. Upon completion of the synthesis the peptide-resin is treated with 30% piperidine in DMF solution for 4 to 24 h to remove the FMOC protecting group. After several washes with methylene chloride the peptide-resin is coupled with BOC-Gly and deblocked. After base washing the peptide-resin is coupled to the appropriate acids to provide after work-up and HPLC purification the following compounds as the trifluoroacetate salt:

(a) 5LactD2Nal$_1$-D4ClPhe$^2$-D3Pal$^3$-Ser$^4$-NMeTyr$^5$-DLys-(GlyShik)$_6$-Leu$^7$-Lys(N-epsilon-Isopropyl)$^8$-Pro$^9$-DAla$^{10}$NH$_2$ (b) 5LactD2Nal$_1$-D4ClPhe$^2$-D3Pal$^3$-Ser$^4$-NMeTyr$^5$-DLys-(GlyNic)$_6$-Leu$^7$-Lys(N-epsilon-Isopropyl)$^8$-Pro$^9$-DAla$^{10}$NH$_2$

EXAMPLE 25

The procedure described in Example 23 is used. Upon completion of the synthesis the resin was treated with 30% piperidine in DMF solution for 4 to 24 h to remove the FMOC protecting group. After several washes with methylene chloride the peptide-resin is treated with a solution of carbonyldiimidazole (0.9 g) in DMF (18 ml) for 15 minutes, washed (×3) with methylene chloride, and then reacted overnight with the appropriate acid hydrazides to provide after work-up and HPLC purification the following compounds as the trifluoroacetate salt:

(a) 5LactD2Nal$^1$-D4ClPhe$^2$-D3Pal$^3$ -Ser$^4$-NMeTyr$^5$-DLys(AzaglyNic)$^6$ -Leu$^7$-Lys(N-epsilon-Isopropyl)$^8$-Pro$^9$-DAla$^{10}$NH$_2$ (a) 5LactD2Nal$^1$-D4ClPhe$^2$-D3Pal$^3$ -Ser$^4$-NMeTyr$^5$-DLys(Azagly-2-Fur)$^6$ -Leu$^7$-Lys(N-epsilon-Isopropyl)$^8$-Pro$^9$-DAla$^{10}$NH$_2$

EXAMPLE 26

Preparation of 5LactD2Nal$^1$-D4ClPhe$^2$-D3Pal$^3$ -Ser$^4$-NMeTyr$^5$-DLys(Atz)$^6$ -Leu$^7$-Lys(N-epsilon-Isopropyl)$^8$-Pro$^9$-DAla$^{10}$NH$_2$ The procedure described in Example 23 is used, upon completion of the synthesis the resin is treated with 30% piperidine in DMF solution for 4 to 24 h to remove the FMOC protecting group. The resin is washed three times each with (1:1) DCM/DMF and DCM, then treated with a solution of diphenyl cyanocarbonimidate (0.43 g in 15 mL DMF), and the mixture bubbled for 16 h. The resin is washed three times each with (1:1) DCM/DMF, MeOH, and DCM, then treated with neat hydrazine (10 mL) for 8 hours. The resin is again washed three times each with (1:1) DCM/DMF, MeOH, and DCM, and dried in vacuo overnight over $P_2O_5$. After HF treatment and HPLC purification 5LactD2Nal$^1$-D4ClPhe$^2$-D3Pal$^3$ -Ser$^4$-NMeTyr$^5$-DLys(Atz)$^6$ -Leu$^7$-Lys(N-epsilon-Isopropyl)$^8$-Pro$^9$-DAla$^{10}$NH$_2$ is obtained as the trifluoroacetate salt.

EXAMPLE 27

The procedure described in Example 7 is used, but substituting the appropriate BOC-amino acid for BOC-Leu, after work-up and HPLC purification the following compounds are obtained as the trifluoroacetate salt:

(a) 5LactD2Nal$^1$-D4ClPhe$^2$-D3Pal$^3$ -Ser$^4$-NMeTyr$^5$-DLys-(Nic)$^6$ -Ile$^7$-Lys(N-epsilon-Isopropyl)$^8$-Pro$^9$-DAla$^{10}$NH$_2$ (b) 5LactD2Nal$^1$-D4ClPhe$^2$-D3Pal$^3$ -Ser$^4$-NMeTyr$^5$-DLys-(Nic)$^6$ -NMeLeu$_7$-Lys(N-epsilon-Isopropyl)$^8$-Pro$^9$-DAla$^{10}$NH$_2$ (c) 5LactD2Nal$^1$-D4ClPhe$^2$-D3Pal$^3$ -Ser$^4$-NMeTyr$^5$-DLys-(Nic)$^6$ -t-BuGly$_7$-Lys(N-epsilon-Isopropyl)$^8$-Pro$^9$-DAla$^{10}$NH$_2$ (d) 5LactD2Nal$^1$-D4ClPhe$^2$-D3Pal$^3$ -Ser$^4$-NMeTyr$^5$-DLys-(Nic)$^6$ -Val$^7$-Lys(N-epsilon-Isopropyl)$^8$-Pro$^9$-DAla$^{10}$NH$_2$

EXAMPLE 28

The procedure described in Example 7 is used, but substituting the appropriate BOC-amino acid for BOC-Lys(Isp, CBZ), after work-up and HPLC purification the following compounds are obtained as the trifluoroacetate salt:

(a) 5LactD2Nal$^1$-D4ClPhe$^2$-D3Pal$^3$ -Ser$^4$-NMeTyr$^5$-DLys-(Nic)$^6$ -Leu$^7$-Arg$^8$-Pro$^9$-DAla$^{10}$NH$_2$ (b) 5LactD2Nal$^1$-D4ClPhe$^2$-D3Pal$^3$ -Ser$^4$-NMeTyr$^5$-DLys-(Nic)$^6$ -Leu$^7$-Harg$^8$-Pro$^9$-DAla$^{10}$NH$_2$ (c) 5LactD2Nal$^1$-D4ClPhe$^2$-D3Pal$^3$ -Ser$^4$-NMeTyr$^5$-DLys-(Nic)$^6$ -Leu$^7$-Harg(Et$_2$)$^8$-Pro$^9$-DAla$^{10}$NH$_2$

EXAMPLE 29

Preparation of 5LactD2Nal$^1$-D4ClPhe$^2$-D3Pal$^3$ -Ser$^4$-NMeTyr$^5$-DLys(Nic)$^6$ -Leu$_7$-Lys(N-epsilon-1-hydroxy-isopropyl)$^8$-Pro$^9$-DAla$^{10}$NH$_2$ The procedure described in Example 7 is used, but substituting BOC-Lys(N-epsilon-FMOC) for BOC-Lys(N-epsilon-Cbz, isopropyl). Upon completion of the synthesis the peptide-resin is treated with 30% piperidine in DMF solution for 4 to 24 h to remove the FMOC protecting group. The peptide-resin is washed with methylene chloride and treated with a solution of 0.41 mL (6.00 retool) acetol, 0.38 g (6.00 mmol) sodium cyanoborohydride, and 0.57 mL acetic acid in 27 mL DMF. The mixture is bubbled for 2h. The peptide-resin is washed with DMF and methylene chloride. After work-up and HPLC purification 5LactD2Nal$^1$-D4ClPhe$^2$-D3Pal$^3$ -Ser$^4$-NMeTyr$^5$-DLys(Nic)$^6$ -Leu$^7$-Lys(N-epsilon-1-hydroxy-isopropyl)$^8$-Pro$^9$-DAla$^{10}$NH$_2$ is obtained as the trifluoroacetate salt.

EXAMPLE 30

Preparation of 5LactD2Nal$^1$-D4ClPhe$^2$-D3Pal$^3$ -Ser$^4$-NMeTyr$^5$-DLys(Nic)$^6$ -Leu$^7$-Lys(Isp)$^8$-NMeAla$^9$-DAla$^{10}$NH$_2$ The procedure described in Example 7 is used, but substituting BOC-NMeAla for BOC-Pro, after work-up and HPLC purification 5LactD2Nal$^1$-D4ClPhe$^2$-D3Pal$^3$ -Ser$^4$-NMeTyr$^5$-DLys(Nic)$^6$ -Leu$^7$-Lys(Isp)$^8$-NMeAla$^9$-DAla$^{10}$NH$_2$ is obtained as the trifluoroacetate salt.

EXAMPLE 31

The procedure described in Example 7 is used, but substituting the different BOC-amino acid-resins for BOC-D-Ala-NH-resin (4-methyl-benzhydrylamine resin), after work-up and HPLC purification the following compounds are obtained as the trifluoroacetate salt:
(a) 5LactD2Nal$^1$-D4ClPhe$^2$-D3Pal$^3$ -Ser$^4$-NMeTyr$^5$-DLys(Nic)$^6$-Leu$^7$ -Lys(Isp)$^8$-Pro$^9$-Gly$^{10}$NH$_2$
(b) 5LactD2Nal$^1$-D4ClPhe$^2$-D3Pal$^3$ -Ser$^4$-NMeTyr$^5$-DLys(Nic)$^6$-Leu$^7$ -Lys(Isp)$^8$-Pro$^9$-Sar$^{10}$NH$_2$
(c) 5LactD2Nal$^1$-D4ClPhe$^2$-D3Pal$^3$ -Ser$^4$-NMeTyr$^5$-DLys(Nic)$^6$-Leu$^7$ -Lys(Isp)$^8$-Pro$^9$-DSer$^{10}$NH$_2$

EXAMPLE 32

The procedure described in Example 6 is used, but substituting the appropriate acids for 2(N-pyrrolidinone)-2-(R)-(2-naphthylmethyl)acetic acid (5LactD2Nal), after work-up and HPLC purification the following compounds are obtained as the trifluoroacetate salt:
(a) 5LactGly$^1$-D4ClPhe$^2$-D3Pal$^3$ -Ser$^4$-Tyr$^5$-DCit$^6$-Leu$^7$-Arg$^8$-Pro$^9$ -DAla$^{10}$NH$_2$
(b) 5LactD3Qal$^1$-D4ClPhe$^2$-D3Pal$^3$ -Ser$^4$-Tyr$^5$-DCit$^6$ -Leu7-Arg$^8$-Pro$^9$-DAla$^{10}$NH$_2$
(c) 5LactD4ClPhe$^1$-D4ClPhe$^2$-D3Pal$^3$ -Ser$^4$-Tyr$^5$-DCit$^6$ -Leu7-Arg$^8$-Pro$^9$-DAla$^{10}$NH$_2$
(d) 5LactDPhe$^1$-D4ClPhe$^2$-D3Pal$^3$ -Ser$^4$-Tyr$^5$-DCit$^6$ -Leu7-Arg$^8$-Pro$^9$-DAla$^{10}$NH$_2$
(e) 5LactD1Nal$^1$-D4ClPhe$^2$-D3Pal$^3$ -Ser$^4$-Tyr$^5$-DCit$^6$ -Leu7-Arg$^8$-Pro$^9$-DAla$^{10}$NH$_2$
(f) 6LactGly$^1$-D4ClPhe$^2$-D3Pal$^3$ -Ser$^4$-Tyr$^5$-DCit$^6$ -Leu7-Arg$^8$-Pro$^9$-DAla$^{10}$NH$_2$
(g) 6LactD3Qal$^1$-D4ClPhe$^2$-D3Pal$^3$ -Ser$^4$-Tyr$^5$-DCit$^6$ -Leu7-Arg$^8$-Pro$^9$-DAla$^{10}$NH$_2$
(h) 6LactD4ClPhe$^1$-D4ClPhe$^2$-D3Pal$^3$ -Ser$^4$-Tyr$^5$-DCit$^6$ -Leu7-Arg$^8$-Pro$^9$-DAla$^{10}$NH$_2$
(i) 6LactD4Phe$^1$-D4ClPhe$^2$-D3Pal$^3$ -Ser$^4$-Tyr$^5$-DCit$^6$ -Leu7-Arg$^8$-Pro$^9$-DAla$^{10}$NH$_2$
(j) 6LactD1Nal$^1$-D4ClPhe$^2$-D3Pal$^3$ -Ser$^4$-Tyr$^5$-DCit$^6$ -Leu7-Arg$^8$-Pro$^9$-DAla$^{10}$NH$_2$
(k) 7LactGly$^1$-D4ClPhe$^2$-D3Pal$^3$ -Ser$^4$-Tyr$^5$-DCit$^6$ -Leu7-Arg$^8$-Pro$^9$-DAla$^{10}$NH$_2$
(l) 7LactD2Nal$^1$-D4ClPhe$^2$-D3Pal$^3$ -Ser$^4$-Tyr$^5$-DCit$^6$ -Leu7-Arg$^8$-Pro$^9$-DAla$^{10}$NH$_2$
(m) 7LactD3Qal$^1$-D4ClPhe$^2$-D3Pal$^3$ -Ser$^4$-Tyr$^5$-DCit$^6$ -Leu7-Arg$^8$-Pro$^9$-DAla$^{10}$NH$_2$
(n) 7LactD4ClPhe$^1$-D4ClPhe$^2$-D3Pal$^3$ -Ser$^4$-Tyr$^5$-DCit$^6$ -Leu$^7$-Arg$^8$-Pro$^9$-DAla$^{10}$NH$_2$
(o) 7LactDPhe$^1$-D4ClPhe$^2$-D3Pal$^3$ -Ser$^4$-Tyr$^5$-DCit$^6$ -Leu$^7$-Arg$^8$-Pro$^9$-DAla$^{10}$NH$_2$
(p) 7LactD1Nal$^1$-D4ClPhe$^2$-D3Pal$^3$ -Ser$^4$-Tyr$^5$-DCit$^6$ -Leu$^7$-Arg$^8$-Pro$^9$-DAla$^{10}$NH$_2$
(q) 7LactD2Nal$^1$-D4ClPhe$^2$-D3Pal$^3$ -Ser$^4$-Tyr$^5$-DCit$^6$ -Leu$^7$-Arg$^8$-Pro$^9$-DAla$^{10}$NH$_2$

EXAMPLE 33

The procedure described in Example 12 is used, but substituting the appropriate acids for 2(N-pyrrolidinone)-2-(R)-(2-naphthylmethyl)-acetic acid (5LactD2Nal), after work-up and HPLC purification the following compounds are obtained as the trifluoroacetate salt:
(a) 5LactGly$^1$-D4ClPhe$^2$-D3Pal$^3$ -Ser$^4$-Tyr$^5$-DHcit$^6$-Leu$^7$-Lys(Isp)$^8$-Pro$^9$ -DAla$^{10}$NH$_2$
(b) 5Lact3Qal$^1$-D4ClPhe$^2$-D3Pal$^3$ -Ser$^4$-Tyr$^5$-DHcit$^6$-Leu$^7$-Lys(Isp)$^8$-Pro$^9$ -DAla$^{10}$NH$_2$
(c) 5LactD4ClPhe$^1$-D4ClPhe$^2$-D3Pal$^3$ -Ser$^4$-Tyr$^5$-DHcit$^6$-Leu$^7$-Lys(Isp)$^8$-Pro$^9$ -DAla$^{10}$NH$_2$
(d) 5LactDPhe$^1$-D4ClPhe$^2$-D3Pal$^3$ -Ser$^4$-Tyr$^5$-DHcit$^6$-Leu$^7$-Lys(Isp)$^8$-Pro$^9$ -DAla$^{10}$NH$_2$
(e) 5LactD1Nal$^1$-D4ClPhe$^2$-D3Pal$^3$ -Ser$^4$-Tyr$^5$-DHcit$^6$-Leu$^7$-Lys(Isp)$^8$-Pro$^9$ -DAla$^{10}$NH$_2$
(f) 6LactGly$^1$-D4ClPhe$^2$-D3Pal$^3$ -Ser$^4$-Tyr$^5$-DHcit$^6$-Leu$^7$-Lys(Isp)$^8$-Pro$^9$ -DAla$^{10}$NH$_2$
(g) 6LactD3Qal$^1$-D4ClPhe$^2$-D3Pal$^3$ -Ser$^4$-Tyr$^5$-DHcit$^6$-Leu$^7$-Lys(Isp)$^8$-Pro$^9$ -DAla$^{10}$NH$_2$
(h) 6LactD4ClPhe$^1$-D4ClPhe$^2$-D3Pal$^3$ -Ser$^4$-Tyr$^5$-DHcit$^6$-Leu$^7$-Lys(Isp)$^8$-Pro$^9$ -DAla$^{10}$NH$_2$
(i) 6LactDPhe$^1$-D4ClPhe$^2$-D3Pal$^3$ -Ser$^4$-Tyr$^5$-DHcit$^6$-Leu$^7$-Lys(Isp)$^8$-Pro$^9$ -DAla$^{10}$NH$_2$
(j) 6LactD1Nal$^1$-D4ClPhe$^2$-D3Pal$^3$ -Ser$^4$-Tyr$^5$-DHcit$^6$-Leu$^7$-Lys(Isp)$^8$-Pro$^9$ -DAla$^{10}$NH$_2$
(k) 7LactGly$^1$-D4ClPhe$^2$-D3Pal$^3$ -Ser$^4$-Tyr$^5$-DHcit$^6$-Leu$^7$-Lys(Isp)$^8$-Pro$^9$ -DAla$^{10}$NH$_2$
(l) 7LactD2Nal$^1$-D4ClPhe$^2$-D3Pal$^3$ -Ser$^4$-Tyr$^5$-DHcit$^6$-Leu$^7$-Lys(Isp)$^8$-Pro$^9$ -DAla$^{10}$NH$_2$
(m) 7LactD3Qal$^1$-D4ClPhe$^2$-D3Pal$^3$ -Ser$^4$-Tyr$^5$-DHcit$^6$-Leu$^7$-Lys(Isp)$^8$-Pro$^9$ -DAla$^{10}$NH$_2$
(n) 7LactD4ClPhe$^1$-D4ClPhe$^2$-D3Pal$^3$ -Ser$^4$-Tyr$^5$-DHcit$^6$-Leu$^7$-Lys(Isp)$^8$-Pro$^9$ -DAla$^{10}$NH$_2$
(o) 7LactDPhe$^1$-D4ClPhe$^2$-D3Pal$^3$ -Ser$^4$-Tyr$^5$-DHcit$^6$-Leu$^7$-Lys(Isp)$^8$-Pro$^9$ -DAla$^{10}$NH$_2$
(p) 7LactD1Nal$^1$-D4ClPhe$^2$-D3Pal$^3$ -Ser$^4$-Tyr$^5$-DHcit$^6$-Leu$^7$-Lys(Isp)$^8$-Pro$^9$ -DAla$^{10}$NH$_2$
(q) 6LactD2Nal$^1$-D4ClPhe$^2$-D3Pal$^3$ -Ser$^4$-Tyr$^5$-DHcit$^6$-Leu$^7$-Lys(Isp)$^8$-Pro$^9$ -DAla$^{10}$NH$_2$

EXAMPLE 34

Preparation of 5LactD2Nal$^1$-D4ClPhe$^2$-D3Pal$^3$ -Ser$^4$-Phe(Atz)$^5$-DPhe(Atz)$^6$ -Leu7-Lys(N-epsilon-Isopropyl)$^8$-Pro$^9$-DAla$^{10}$NH$_2$ The procedure described in Example 20 is used, but substituting BOC-D-Phe(4-NH-FMOC) for BOC-DLys(N-epsilon-Nic) the peptide-resin is assembled. Upon completion of the synthesis the peptide-resin is treated with 30% piperidine in DMF solution for 4 to 24 h to remove the FMOC protecting group. The peptide-resin is washed three times each with (1:1) DCM/DMF and DCM, then treated with a solution of diphenyl cyanocarbonimidate (0.86g in 15 mL DMF), and the mixture bubbled for 16 h. The peptide-resin is washed three times each with (1:1) DCM/DMF, MeOH, and DCM, then treated with neat hydrazine (20 mL) for 8 hours. The peptide-resin is again washed three times each with (1:1) DCM/DMF, MeOH, and DCM, and dried in vacuo overnight over $P_2O_5$. After HF treatment and HPLC purification 5LactD2Nal$^1$-D4ClPhe$^2$-D3Pal$^3$ -Ser$^4$-Phe(Atz)$^5$-Phe(Atz)$^6$ -Leu$^7$-Lys(N-epsilon-Isopropyl)$^8$-Pro$^9$-DAla$^{10}$NH$_2$ is obtained as the trifluoroacetate salt:

EXAMPLE 35

The procedure described in Example 34 is used, but substituting the appropriate acids for 2(N-pyrrolidinone)-2-(R)-(2-naphthylmethyl)-acetic acid (5LactD2Nal), after work-up and HPLC purification the following compounds are obtained as the trifluoroacetate salt:

(a) 5LactGly$^1$-D4ClPhe$^2$-D3Pal$^3$ -Ser$^4$-Phe(Atz)$^5$-DPhe(Atz)$^6$ -Leu$^7$-Lys(Isp)$^8$-Pro$^9$-DAla$^{10}$NH$_2$
(b) 5LactD3Qal$^1$-D4ClPhe$^2$-D3Pal$^3$ -Ser$^4$-Phe(Atz)$^5$-DPhe(Atz)$^6$ -Leu$^7$-Lys(Isp)$^8$-Pro$^9$-DAla$^{10}$NH$_2$
(c) 5LactD4ClPhe$^1$-D4ClPhe$^2$-D3Pal$^3$ -Ser$^4$-Phe(Atz)$^5$-DPhe(Atz)$^6$ -Leu$^7$-Lys(Isp)$^8$-Pro$^9$-DAla$^{10}$NH$_2$
(d) 5LactDPhe$^1$-D4ClPhe$^2$-D3Pal$^3$ -Ser$^4$-Phe(Atz)$^5$-DPhe(Atz)$^6$ -Leu$^7$-Lys(Isp)$^8$-Pro$^9$-DAla$^{10}$NH$_2$
(e) 5LactD1Nal$^1$-D4ClPhe$^2$-D3Pal$^3$ -Ser$^4$-Phe(Atz)$^5$-DPhe(Atz)$^6$ -Leu$^7$-Lys(Isp)$^8$-Pro$^9$-DAla$^{10}$NH$_2$
(f) 6LactGly$^1$-D4ClPhe$^2$-D3Pal$^3$ -Ser$^4$-Phe(Atz)$^5$-DPhe(Atz)$^6$ -Leu$^7$-Lys(Isp)$^8$-Pro$^9$-DAla$^{10}$NH$_2$
(g) 6LactD3Qal$^1$-D4ClPhe$^2$-D3Pal$^3$ -Ser$^4$-Phe(Atz)$^5$-DPhe(Atz)$^6$ -Leu$^7$-Lys(Isp)$^8$-Pro$^9$-DAla$^{10}$NH$_2$
(h) 6LactD4ClPhe$^1$-D4ClPhe$^2$-D3Pal$^3$ -Ser$^4$-Phe(Atz)$^5$-DPhe(Atz)$^6$ -Leu$^7$-Lys(Isp)$^8$-Pro$^9$-DAla$^{10}$NH$_2$
(i) 6LactDPhe$^1$-D4ClPhe$^2$-D3Pal$^3$ -Ser$^4$-Phe(Atz)$^5$-DPhe(Atz)$^6$ -Leu$^7$-Lys(Isp)$^8$-Pro$^9$-DAla$^{10}$NH$_2$
(j) 6LactD1Nal$^1$-D4ClPhe$^2$-D3Pal$^3$ -Ser$^4$-Phe(Atz)$^5$-DPhe(Atz)$^6$ -Leu$^7$-Lys(Isp)$^8$-Pro$^9$-DAla$^{10}$NH$_2$
(k) 7LactGly$^1$-D4ClPhe$^2$-D3Pal$^3$ -Ser$^4$-Phe(Atz)$^5$-DPhe(Atz)$^6$ -Leu$^7$-Lys(Isp)$^8$-Pro$^9$-DAla$^{10}$NH$_2$
(l) 7LactD2Nal$^1$-D4ClPhe$^2$-D3Pal$^3$ -Ser$^4$-Phe(Atz)$^5$-DPhe(Atz)$^6$ -Leu$^7$-Lys(Isp)$^8$-Pro$^9$-DAla$^{10}$NH$_2$
(m) 7LactD3Qal$^1$-D4ClPhe$^2$-D3Pal$^3$ -Ser$^4$-Phe(Atz)$^5$-DPhe(Atz)$^6$ -Leu$^7$-Lys(Isp)$^8$-Pro$^9$-DAla$^{10}$NH$_2$
(n) 7LactD4ClPhe$^1$-D4ClPhe$^2$-D3Pal$^3$ -Ser$^4$-Phe(Atz)$^5$-DPhe(Atz)$^6$ -Leu$^7$-Lys(Isp)$^8$-Pro$^9$-DAla$^{10}$NH$_2$
(o) 7LactDPhe$^1$-D4ClPhe$^2$-D3Pal$^3$ -Ser$^4$-Phe(Atz)$^5$-DPhe(Atz)$^6$ -Leu$^7$-Lys(Isp)$^8$-Pro$^9$-DAla$^{10}$NH$_2$
(p) 7LactD1Nal$^1$-D4ClPhe$^2$-D3Pal$^3$ -Ser$^4$-Phe(Atz)$^5$-DPhe(Atz)$^6$ -Leu$^7$-Lys(Isp)$^8$-Pro$^9$-DAla$^{10}$NH$_2$
(q) 6LactD2Nal$^1$-D4ClPhe$^2$-D3Pal$^3$ -Ser$^4$-Phe(Atz)$^5$-DPhe(Atz)$^6$ -Leu$^7$-Lys(Isp)$^8$-Pro$^9$-DAla$^{10}$NH$_2$

EXAMPLE 36

The procedure described in Example 35 was used, but substituting BOC-NMePhe( 4-NH-Fmoc) for BOC-Phe(4-NH-Fmoc), after work-up and HPLC purification the following compounds are obtained as the trifluoroacetate salt:

(a) 5LactGly$^1$-D4ClPhe$^2$-D3Pal$^3$ -Ser$^4$-NMePhe(Atz)$^5$-DPhe(Atz)$^6$ -Leu$^7$-Lys(Isp)$^8$-Pro$^9$-DAla$^{10}$NH$_2$
(b) 5LactD3Qal$^1$-D4ClPhe$^2$-D3Pal$^3$ -Ser$^4$-NMePhe(Atz)$^5$-DPhe(Atz)$^6$ -Leu$^7$-Lys(Isp)$^8$-Pro$^9$-DAla$^{10}$NH$_2$
(c) 5LactD4ClPhe$^1$-D4ClPhe$^2$-D3Pal$^3$ -Ser$^4$-NMePhe(Atz)$^5$-DPhe(Atz)$^6$ -Leu$^7$-Lys(Isp)$^8$-Pro$^9$-DAla$^{10}$NH$_2$
(d) 5LactDPhe$^1$-D4ClPhe$^2$-D3Pal$^3$ -Ser$^4$-NMePhe(Atz)$^5$-DPhe(Atz)$^6$ -Leu$^7$-Lys(Isp)$^8$-Pro$^9$-DAla$^{10}$NH$_2$
(e) 5LactD1Nal$^1$-D4ClPhe$^2$-D3Pal$^3$ -Ser$^4$-NMePhe(Atz)$^5$-DPhe(Atz)$^6$ -Leu$^7$-Lys(Isp)$^8$-Pro$^9$-DAla$^{10}$NH$_2$
(f) 6LactGly$^1$-D4ClPhe$^2$-D3Pal$^3$ -Ser$^4$-NMePhe(Atz)$^5$-DPhe(Atz)$^6$ -Leu$^7$-Lys(Isp)$^8$-Pro$^9$-DAla$^{10}$NH$_2$
(g) 6LactD3Qal$^1$-D4ClPhe$^2$-D3Pal$^3$ -Ser$^4$-NMePhe(Atz)$^5$-DPhe(Atz)$^6$ -Leu$^7$-Lys(Isp)$^8$-Pro$^9$-DAla$^{10}$NH$_2$
(h) 6LactD4ClPhe$^1$-D4ClPhe$^2$-D3Pal$^3$ -Ser$^4$-NMePhe(Atz)$^5$-DPhe(Atz)$^6$ -Leu$^7$-Lys(Isp)$^8$-Pro$^9$-DAla$^{10}$NH$_2$
(i) 6LactDPhe$^1$-D4ClPhe$^2$-D3Pal$^3$ -Ser$^4$-NMePhe(Atz)$^5$-DPhe(Atz)$^6$ -Leu$^7$-Lys(Isp)$^8$-Pro$^9$-DAla$^{10}$NH$_2$
(j) 6LactD1Nal$^1$-D4ClPhe$^2$-D3Pal$^3$ -Ser$^4$-NMePhe(Atz)$^5$-DPhe(Atz)$^6$-Leu$^7$ -Lys(Isp)$^8$-Pro$^9$-DAla$^{10}$NH$_2$
(k) 7LactGly$^1$-D4ClPhe$^2$-D3Pal$^3$ -Ser$^4$-NMePhe(Atz)$^5$-DPhe(Atz)$^6$-Leu$^7$ -Lys(Isp)$^8$-Pro$^9$-DAla$^{10}$NH$_2$
(l) 7LactD2Nal$^1$-D4ClPhe$^2$-D3Pal$^3$ -Ser$^4$-NMePhe(Atz)$^5$-DPhe(Atz)$^6$-Leu$^7$ -Lys(Isp)$^8$-Pro$^9$-DAla$^{10}$NH$_2$
(m) 7LactD3Qal$^1$-D4ClPhe$^2$-D3Pal$^3$ -Ser$^4$-NMePhe(Atz)$^5$-DPhe(Atz)$^6$-Leu$^7$ -Lys(Isp)$^8$-Pro$^9$-DAla$^{10}$NH$_2$
(n) 7LactD4ClPhe$^1$-D4ClPhe$^2$-D3Pal$^3$ -Ser$^4$-NMePhe(Atz)$^5$-DPhe(Atz)$^6$-Leu$^7$ -Lys(Isp)$^8$-Pro$^9$-DAla$^{10}$NH$_2$
(o) 7LactDPhe$^1$-D4ClPhe$^2$-D3Pal$^3$ -Ser$^4$-NMePhe(Atz)$^5$-DPhe(Atz)$^6$-Leu$^7$ -Lys(Isp)$^8$-Pro$^9$-DAla$^{10}$NH$_2$
(p) 7LactD1Nal$^1$-D4ClPhe$^2$-D3Pal$^3$ -Ser$^4$-NMePhe(Atz)$^5$-DPhe(Atz)$^6$-Leu$^7$ -Lys(Isp)$^8$-Pro$^9$-DAla$^{10}$NH$_2$
(q) 6LactD2Nal$^1$-D4ClPhe$^2$-D3Pal$^3$ -Ser$^4$-NMePhe(Atz)$^5$-DPhe(Atz)$^6$-Leu$^7$ -Lys(Isp)$^8$-Pro$^9$-DAla$^{10}$NH$_2$
(r) 5LactD2Nal$^1$-D4ClPhe$^2$-D3Pal$^3$ -Ser$^4$-NMePhe(Atz)$^5$-DPhe(Atz)$^6$-Leu$^7$ -Lys(Isp)$^8$-Pro$^9$-DAla$^{10}$NH$_2$

EXAMPLE 37

Preparation of 5LactD2Nal$^1$-D4ClPhe$^2$-D3Pal$^3$ -Ser$^4$-Tyr$^5$-DHarg(Et$_2$)$^6$-Leu$^7$ -HArg(Et$_2$)$^8$-Pro$^9$-DAla$^{10}$NH$_2$

EXAMPLE 37

Preparation of 5LactD2Nal$^1$-D4ClPhe$^2$-D3Pal$^3$ -Ser$^4$-Tyr$^5$-DHarg (Et$_2$)$^6$ -Leu$^7$-HArg(Et$_2$)$^8$-Pro$^9$-DAla$^{10}$NH$_2$ The procedure described in Example 6 is used, but substituting BOC-D-Harg(Et$_2$) for BOC-DLys(N-epsilon-Nic) and BOC-Harg(Et$_2$) for BOC-Lys(n-epsilon-Cbz,isopropyl). After HF treatment and HPLC purification 5LactD2Nal$^1$-D4ClPhe$^2$-D3Pal$^3$ -Ser$^4$-Tyr$^5$-DHarg(Et$_2$)$^6$ -Leu$^7$-HArg(Et$_2$)$^8$-Pro$^9$-DAla$^{10}$NH$_2$ is obtained as the trifluoroacetate salt.

EXAMPLE 38

The procedure described in Example 37 is used, but substituting the appropriate acids for 2(N-pyrrolidinone)-2-(R)-(2-naphthylmethyl)-acetic acid (5LactD2Nal), after work-up and HPLC purification the following compounds are obtained as the trifluoroacetate salt:

(a) 5LactGly$^1$-D4ClPhe$^2$-D3Pal$^3$ -Ser$^4$-Tyr$^5$-DHarg(Et$_2$)$^6$-Leu$^7$-HArg(Et$_2$)$^8$ -Pro$^9$-DAla$^{10}$NH$_2$
(b) 5LactD3Qal$^1$-D4ClPhe$^2$-D3Pal$^3$ -Ser$^4$-Tyr$^5$-DHarg(Et$_2$)$^6$-Leu$^7$-HArg(Et$_2$)$^8$ -Pro$^9$-DAla$^{10}$NH$_2$
(c) 5LactD4ClPhe$^1$-D4ClPhe$^2$-D3Pal$^3$ -Ser$^4$-Tyr$^5$-DHarg(Et$_2$)$^6$-Leu$^7$-HArg(Et$_2$)$^8$ -Pro$^9$-DAla$^{10}$NH$_2$
(d) 5LactDPhe$^1$-D4ClPhe$^2$-D3Pal$^3$ -Ser$^4$-Tyr$^5$-DHarg(Et$_2$)$^6$-Leu$^7$-HArg(Et$_2$)$^8$ -Pro$^9$-DAla$^{10}$NH$_2$
(e) 5LactD1Nal$^1$-D4ClPhe$^2$-D3Pal$^3$ -Ser$^4$-Tyr$^5$-DHarg(Et$_2$)$^6$-Leu$^7$-HArg(Et$_2$)$^8$ -Pro$^9$-DAla$^{10}$NH$_2$
(f) 6LactGly$^1$-D4ClPhe$^2$-D3Pal$^3$ -Ser$^4$-Tyr$^5$-DHarg(Et$_2$)$^6$-Leu$^7$-HArg(Et$_2$)$^8$ -Pro$^9$-DAla$^{10}$NH$_2$
(g) 6LactD3Qal$^1$-D4ClPhe$^2$-D3Pal$^3$ -Ser$^4$-Tyr$^5$-DHarg(Et$_2$)$^6$-Leu$^7$-HArg(Et$_2$)$^8$ -Pro$^9$-DAla$^{10}$NH$_2$
(h) 6LactD4ClPhe$^1$-D4ClPhe$^2$-D3Pal$^3$ -Ser$^4$-Tyr$^5$-DHarg(Et$_2$)$^6$-Leu$^7$-HArg(Et$_2$)$^8$ -Pro$^9$-DAla$^{10}$NH$_2$
(i) 6LactDPhe$^1$-D4ClPhe$^2$-D3Pal$^3$ -Ser$^4$-Tyr$^5$-DHarg(Et$_2$)$^6$-Leu$^7$-HArg(Et$_2$)$^8$ -Pro$^9$-DAla$^{10}$NH$_2$
(j) 6LactD1Nal$^1$-D4ClPhe$^2$-D3Pal$^3$ -Ser$^4$-Tyr$^5$-DHarg(Et$_2$)$^6$-Leu$^7$-HArg(Et$_2$)$^8$ -Pro$^9$-DAla$^{10}$NH$_2$ (k) 7LactGly$^1$-D4ClPhe$^2$-D3Pal$^3$ -Ser$^4$-Tyr$^5$-DHarg(Et$_2$)$^6$-Leu$^7$-HArg(Et$_2$)$^8$ -Pro$^9$-DAla$^{10}$NH$_2$
(l) 7LactD2Nal$^1$-D4ClPhe$^2$-D3Pal$^3$ -Ser$^4$-Tyr$^5$-DHarg(Et$_2$)$^6$-Leu$^7$-HArg(Et$_2$)$^8$ -Pro$^9$-DAla$^{10}$NH$_2$
(m) 7LactD3Qal$^1$-D4ClPhe$^2$-D3Pal$^3$ -Ser$^4$-Tyr$^5$-DHarg(Et$_2$)$^6$-Leu$^7$-HArg(Et$_2$)$^8$ -Pro$^9$-DAla$^{10}$NH$_2$
(n) 7LactD4ClPhe$^1$-D4ClPhe$^2$-D3Pal$^3$ -Ser$^4$-Tyr$^5$-DHarg(Et$_2$)$^6$-Leu$^7$-HArg(Et$_2$)$^8$ -Pro$^9$-DAla$^{10}$NH$_2$
(o) 7LactDPhe$^1$-D4ClPhe$^2$-D3Pal$^3$ -Ser$^4$-Tyr$^5$-DHarg(Et$_2$)$^6$-Leu$^7$-HArg(Et$_2$)$^8$ -Pro$^9$-DAla$^{10}$NH$_2$
(p) 7LactD1Nal$^1$-D4ClPhe$^2$-D3Pal$^3$ -Ser$^4$-Tyr$^5$-DHarg(Et$_2$)$^6$-Leu$^7$-HArg(Et$_2$)$^8$ -Pro$^9$-DAla$^{10}$NH$_2$
(q) 6Lact2Nal$^1$-D4ClPhe$^2$-D3Pal$^3$ -Ser$^4$-Tyr$^5$-DHarg(Et$_2$)$^6$-Leu$^7$-HArg(Et$_2$)$^8$ -Pro$^9$-DAla$^{10}$NH$_2$

EXAMPLE 39

Preparation of 5LactD2Nal$^1$-D4ClPhe$^2$-D3Pal$^3$ -Ser$^4$-Tyr$^5$-DLys(Shik)$^6$ -Leu$^7$-Arg$^8$-Pro$^9$-DAla$^{10}$NH$_2$ The procedure described in Example 6 is used, but substituting BOC-D-Lys(N-epsilon-FMOC) for BOC-DCit using two 1 hr coupling. Upon completion of the synthesis the peptide-resin is treated with 30% piperidine in DMF solution for 4 to 24 h to remove the FMOC protecting group. After several washes with methylene chloride the peptide-resin is coupled with shikimic acid with the two-4h protocol. After HF treatment and HPLC purification 5LactD2Nal$^1$-D4ClPhe$^2$-D3Pal$^3$ -Ser$^4$-Tyr$^5$-DLys(Shik)$^6$ -Leu$^7$-Arg$^8$-Pro$^9$-DAla$^{10}$NH$_2$ is obtained as the trifluoroacetate salt.

EXAMPLE 40

The procedure described in Example 39 is used, but substituting the appropriate acids for 2(N-pyrrolidinone)-2-(R)-(2-naphthylmethyl)-acetic acid (5LactD2Nal), after work-up and HPLC purification the following compounds are obtained as the trifluoroacetate salt:
(a) 5LactGly$^1$-D4ClPhe$^2$-D3Pal$^3$ -Ser$^4$-Tyr$^5$-DLys(Shik)$^6$ -Leu$_7$-Arg$^8$-Pro$^9$-DAla$^{10}$NH$_2$
(b) 5LactD3Qal$^1$-D4ClPhe$^2$-D3Pal$^3$ -Ser$^4$-Tyr$^5$-DLys(Shik)$^6$ -Leu$^7$-Arg$^8$-Pro$^9$-DAla$^{10}$NH$_2$
(c) 5LactD4ClPhe$^1$-D4ClPhe$^2$-D3Pal$^3$ -Ser$^4$-Tyr$^5$-DLys(Shik)$^6$ -Leu$^7$-Arg$^8$-Pro$^9$-DAla$^{10}$NH$_2$
(d) 5LactDPhe$^1$-D4ClPhe$^2$-D3Pal$^3$ -Ser$^4$-Tyr$^5$-DLys(Shik)$^6$ -Leu$_7$-Arg$^8$-Pro$^9$-DAla$^{10}$NH$_2$
(e) 5LactD1Nal$^1$-D4ClPhe$^2$-D3Pal$^3$ -Ser$^4$-Tyr$^5$-DLys(Shik)$^6$ -Leu$^7$-Arg$^8$-Pro$^9$-DAla$^{10}$NH$_2$
(f) 6LactGly$^1$-D4ClPhe$^2$-D3Pal$^3$ -Ser$^4$-Tyr$^5$-DLys(Shik)$^6$ -Leu$_7$-Arg$^8$-Pro$^9$-DAla$^{10}$NH$_2$
(g) 6LactD3Qal$^1$-D4ClPhe$^2$-D3Pal$^3$ -Ser$^4$-Tyr$^5$-DLys(Shik)$^6$ -Leu$^7$-Arg$^8$-Pro$^9$-DAla$^{10}$NH$_2$
(h) 6LactD4ClPhe$^1$-D4ClPhe$^2$-D3Pal$^3$ -Ser$^4$-Tyr$^5$-DLys(Shik)$^6$ -Leu$^7$-Arg$^8$-Pro$^9$-DAla$^{10}$NH$_2$
(i) 6LactDPhe$^1$-D4ClPhe$^2$-D3Pal$^3$ -Ser$^4$-Tyr$^5$-DLys(Shik)$^6$ -Leu$_7$-Arg$^8$-Pro$^9$-DAla$^{10}$NH$_2$
(j) 6LactD1Nal$^1$-D4ClPhe$^2$-D3Pal$^3$ -Ser$^4$-Tyr$^5$-DLys(Shik)$^6$ -Leu$^7$-Arg$^8$-Pro$^9$-DAla$^{10}$NH$_2$
(k) 7LactGly$^1$-D4ClPhe$^2$-D3Pal$^3$ -Ser$^4$-Tyr$^5$-DLys(Shik)$^6$ -Leu$_7$-Arg$^8$-Pro$^9$-DAla$^{10}$NH$_2$
(l) 7LactD2Nal$^1$-D4ClPhe$^2$-D3Pal$^3$ -Ser$^4$-Tyr$^5$-DLys(Shik)$^6$ -Leu$^7$-Arg$^8$-Pro$^9$-DAla$^{10}$NH$_2$
(m) 7LactD3Qal$^1$-D4ClPhe$^2$-D3Pal$^3$ -Ser$^4$-Tyr$^5$-DLys(Shik)$^6$ -Leu$^7$-Arg$^8$-Pro$^9$-DAla$^{10}$NH$_2$
(n) 7LactD4ClPhe$^1$-D4ClPhe$^2$-D3Pal$^3$ -Ser$^4$-Tyr$^5$-DLys(Shik)$^6$ -Leu$^7$-Arg$^8$-Pro$^9$-DAla$^{10}$NH$_2$
(o) 7LactDPhe$^1$-D4ClPhe$^2$-D3Pal$^3$ -Ser$^4$-Tyr$^5$-DLys(Shik)$^6$ -Leu$_7$-Arg$^8$-Pro$^9$-DAla$^{10}$NH$_2$
(p) 7LactD1Nal$^1$-D4ClPhe$^2$-D3Pal$^3$ -Ser$^4$-Tyr$^5$-DLys(Shik)$^6$ -Leu$^7$-Arg$^8$-Pro$^9$-DAla$^{10}$NH$_2$
(q) 6LactD2Nal$^1$-D4ClPhe$^2$-D3Pal$^3$ -Ser$^4$-Tyr$^5$-DLys(Shik)$^6$ -Leu$^7$-Arg$^8$-Pro$^9$-DAla$^{10}$NH$_2$

EXAMPLE 41

Preparation of 5LactD2Nal$^1$-D4ClPhe$^2$-D3Pal$^3$ -Ser$^4$-Tyr$^5$-DLys(GlyShik)$^6$ -Leu$^7$-Arg$^8$-Pro$^9$-DAla$^{10}$NH$_2$ The procedure described in Example 3 is used, but substituting BOC-Tyr(O-2,6-diCl-Bzl) for BOC-NMeTyr(O-2,6-diCl-Bzl). After HF treatment and HPLC purification 5LactD2Nal$^1$-D4ClPhe$^2$-D3Pal$^3$ -Ser$^4$-Tyr$^5$-DLys(GlyShik)$^6$ -Leu$^7$-Arg$^8$-Pro$^9$-DAla$^{10}$NH$_2$ is obtained as the trifluoroacetate salt.

EXAMPLE 42

The procedure described in Example 41 is used, but substituting the appropriate acids for 2(N-pyrrolidinone)-2-(R)-(2-naphthylmethyl)-acetic acid (5LactD2Nal), after work-up and HPLC purification the following compounds are obtained as the trifluoroacetate salt:
(a) 5LactGly$^1$-D4ClPhe$^2$-D3Pal$^3$ -Ser$^4$-Tyr$^5$-DLys(GlyShik)$^6$ -Leu$^7$-Arg$^8$-Pro$^9$-DAla$^{10}$NH$_2$
(b) 5LactD3Qal$^1$-D4ClPhe$^2$-D3Pal$^3$ -Ser$^4$-Tyr$^5$-DLys(GlyShik)$^6$ -Leu$^7$-Arg$^8$-Pro$^9$-DAla$^{10}$NH$_2$
(c) 5LactD4ClPhe$^1$-D4ClPhe$^2$-D3Pal$^3$ -Ser$^4$-Tyr$^5$-DLys(GlyShik)$^6$ -Leu$^7$-Arg$^8$-Pro$^9$-DAla$^{10}$NH$_2$
(d) 5LactDPhe$^1$-D4ClPhe$^2$-D3Pal$^3$ -Ser$^4$-Tyr$^5$-DLys(GlyShik)$^6$ -Leu$^7$-Arg$^8$-Pro$^9$-DAla$^{10}$NH$_2$
(e) 5LactD1Nal$^1$-D4ClPhe$^2$-D3Pal$^3$ -Ser$^4$-Tyr$^5$-DLys(GlyShik)$^6$ -Leu$^7$-Arg$^8$-Pro$^9$-DAla$^{10}$NH$_2$
(f) 6LactGly$^1$-D4ClPhe$^2$-D3Pal$^3$ -Ser$^4$-Tyr$^5$-DLys(GlyShik)$^6$ -Leu$^7$-Arg$^8$-Pro$^9$-DAla$^{10}$NH$_2$
(g) 6LactD3Qal$^1$-D4ClPhe$^2$-D3Pal$^3$ -Ser$^4$-Tyr$^5$-DLys(GlyShik)$^6$ -Leu$^7$-Arg$^8$-Pro$^9$-DAla$^{10}$NH$_2$
(h) 6LactD4ClPhe$^1$-D4ClPhe$^2$-D3Pal$^3$ -Ser$^4$-Tyr$^5$-DLys(GlyShik)$^6$ -Leu$^7$-Arg$^8$-Pro$^9$-DAla$^{10}$NH$_2$
(i) 6LactDPhe$^1$-D4ClPhe$^2$-D3Pal$^3$ -Ser$^4$-Tyr$^5$-DLys(GlyShik)$^6$ -Leu$^7$-Arg$^8$-Pro$^9$-DAla$^{10}$NH$_2$
(j) 6LactD1Nal$^1$-D4ClPhe$^2$-D3Pal$^3$ -Ser$^4$-Tyr$^5$-DLys(GlyShik)$^6$ -Leu$^7$-Arg$^8$-Pro$^9$-DAla$^{10}$NH$_2$
(k) 7LactGly$^1$-D4ClPhe$^2$-D3Pal$^3$ -Ser$^4$-Tyr$^5$-DLys(GlyShik)$^6$ -Leu$^7$-Arg$^8$-Pro$^9$-DAla$^{10}$NH$_2$
(l) 7LactD2Nal$^1$-D4ClPhe$^2$-D3Pal$^3$ -Ser$^4$-Tyr$^5$-DLys(GlyShik)$^6$ -Leu$^7$-Arg$^8$-Pro$^9$-DAla$^{10}$NH$_2$
(m) 7LactD3Qal$^1$-D4ClPhe$^2$-D3Pal$^3$ -Ser$^4$-Tyr$^5$-DLys(GlyShik)$^6$ -Leu$^7$-Arg$^8$-Pro$^9$-DAla$^{10}$NH$_2$
(n) 7LactD4ClPhe$^1$-D4ClPhe$^2$-D3Pal$^3$ -Ser$^4$-Tyr$^5$-DLys(GlyShik)$^6$ -Leu$^7$-Arg$^8$-Pro$^9$-DAla$^{10}$NH$_2$
(o) 7LactDPhe$^1$-D4ClPhe$^2$-D3Pal$^3$ -Ser$^4$-Tyr$^5$-DLys(GlyShik)$^6$ -Leu$^7$-Arg$^8$-Pro$^9$-DAla$^{10}$NH$_2$
(p) 7LactD1Nal$^1$-D4ClPhe$^2$-D3Pal$^3$ -Ser$^4$-Tyr$^5$-DLys(GlyShik)$^6$ -Leu$^7$-Arg$^8$-Pro$^9$-DAla$^{10}$NH$_2$
(q) 6LactD2Nal$^1$-D4ClPhe$^2$-D3Pal$^3$ -Ser$^4$-Tyr$^5$-DLys(GlyShik)$^6$ -Leu$^7$-Arg$^8$-Pro$^9$-DAla$^{10}$NH$_2$

EXAMPLE 43

Preparation of 5LactD2Nal$^1$-D4ClPhe$^2$-D3Pal$^3$ -Ser$^4$-Tyr$^5$-DLys(Shik)$^6$ -Leu$^7$-Harg$^8$-Pro$^9$-DAla$^{10}$NH$_2$ The procedure described in Example 4 is used, but substituting BOC-Tyr(O-2,6-diCl-Bzl) for BOC-NMeTyr(O-2,6-diCl-Bzl). After HF treatment and HPLC purification 5LactD2Nal$^1$-D4ClPhe$^2$-D3Pal$^3$ -Ser$^4$-Tyr$^5$-DLys(Shik)$^6$ -Leu$^7$-Harg$^8$-Pro$^9$-DAla$^{10}$NH$_2$ is obtained as the trifluoroacetate salt.

EXAMPLE 44

The procedure described in Example 43 is used, but substituting the appropriate acids for 2(N-pyrrolidinone)-2-(R)-(2-naphthylmethyl)-acetic acid (5LactD2Nal), after work-up and HPLC purification the following compounds are obtained as the trifluoroacetate:

(a) 5LactGly1-D4ClPhe$^2$-D3Pal$^3$ -Ser$^4$-Tyr$^5$-DLys(Shik)$^6$ -Leu$^7$-Harg$^8$-Pro$^9$-DAla$^{10}$NH$_2$
(b) 5LactD3Qal$^1$-D4ClPhe$^2$-D3Pal$^3$ -Ser$^4$-Tyr$^5$-DLys(Shik)$^6$ -Leu$^7$-Harg$^8$-Pro$^9$-DAla$^{10}$NH$_2$
(c) 5LactD4ClPhe$^1$-D4ClPhe$^2$-D3Pal$^3$ -Ser$^4$-Tyr$^5$-DLys(Shik)$^6$ -Leu$^7$-Harg$^8$-Pro$^9$-DAla$^{10}$NH$_2$
(d) 5LactDPhe$^1$-D4ClPhe$^2$-D3Pal$^3$ -Ser$^4$-Tyr$^5$-DLys(Shik)$^6$ -Leu$^7$-Harg$^8$-Pro$^9$-DAla$^{10}$NH$_2$
(c) 5LactD1Nal$^1$-D4ClPhe$^2$-D3Pal$^3$ -Ser$^4$-Tyr$^5$-DLys(Shik)$^6$ -Leu$^7$-Harg$^8$-Pro$^9$-DAla$^{10}$NH$_2$
(f) 6LactGly$^1$-D4ClPhe$^2$-D3Pal$^3$ -Ser$^4$-Tyr$^5$-DLys(Shik)$^6$ -Leu$^7$-Harg$^8$-Pro$^9$-DAla$^{10}$NH$_2$
(h) 6LactD4ClPhe$^1$-D4ClPhe$^2$-D3Pal$^3$ -Ser$^4$-Tyr$^5$-DLys(Shik)$^6$ -Leu$^7$-Harg$^8$-Pro$^9$-DAla$^{10}$NH$_2$
(i) 6LactDPhe$^1$-D4ClPhe$^2$-D3Pal$^3$ -Ser$^4$-Tyr$^5$-DLys(Shik)$^6$ -Leu7-Harg$^8$-Pro$^9$-DAla$^{10}$NH$_2$
(j) 6LactD1Nal$^1$-D4ClPhe$^2$-D3Pal$^3$ -Ser$^4$-Tyr$^5$-DLys(Shik)$^6$ -Leu$^7$-Harg$^8$-Pro$^9$-DAla$^{10}$NH$_2$
(k) 7LactGly$^1$-D4ClPhe$^2$-D3Pal$^3$ -Ser$^4$-Tyr$^5$-DLys(Shik)$^6$ -Leu7-Harg$^8$-Pro$^9$-DAla$^{10}$NH$_2$
(m) 7LactD3Qal$^1$-D4ClPhe$^2$-D3Pal$^3$ -Ser$^4$-Tyr$^5$-DLys(Shik)$^6$ -Leu$^7$-Harg$^8$-Pro$^9$-DAla$^{10}$NH$_2$
(n) 7LactD4ClPhe$^1$-D4ClPhe$^2$-D3Pal$^3$ -Ser$^4$-Tyr$^5$-DLys(Shik)$^6$ -Leu$^7$-Harg$^8$-Pro$^9$-DAla$^{10}$NH$_2$
(o) 7LactDPhe$^1$-D4ClPhe$^2$-D3Pal$^3$ -Ser$^4$-Tyr$^5$-DLys(Shik)$^6$ -Leu7-Harg$^8$-Pro$^9$-DAla$^{10}$NH$_2$
(p) 7LactD1Nal$^1$-D4ClPhe$^2$-D3Pal$^3$ -Ser$^4$-Tyr$^5$-DLys(Shik)$^6$ -Leu$^7$-Harg$^8$-Pro$^9$-DAla$^{10}$NH$_2$
(q) 6LactD2Nal$^1$-D4ClPhe$^2$-D3Pal$^3$ -Ser$^4$-Tyr$^5$-DLys(Shik)$^6$ -Leu$^7$-Harg$^8$-Pro$^9$-DAla$^{10}$NH$_2$

EXAMPLE 45

Preparation of 5LactD2Nal$^1$-D4ClPhe$^2$-D3Pal$^3$ -Ser$^4$-Tyr$^5$-DLys(GlyShik)$^6$ -Leu$^7$-Harg$^8$-Pro$^9$-DAla$^{10}$NH$_2$ The procedure described in Example 5 is used, but substituting BOC-Tyr(O-2,6-diCl-Bzl) for BOC-NMeTyr(O-2,6-diCl-Bzl). After HF treatment and HPLC purification 5LactD2Nal$^1$-D4ClPhe$^2$-D3Pal$^3$ -Ser$^4$-Tyr$^5$-DLys(GlyShik)$^6$ -Leu$^7$-Harg$^8$-Pro$^9$-DAla$^{10}$NH$_2$ is obtained as the trifluoroacetate salt.

EXAMPLE 46

The procedure described in Example 45 is used, but substituting the appropriate acids for 2(N-pyrrolidinone)-2-(R)-(2-naphthylmethyl)-acetic acid (5LactD2Nal), after work-up and HPLC purification the following compounds are obtained as the trifluoroacetate:

(a) 5LactGly$^1$-D4ClPhe$^2$-D3Pal$^3$ -Ser$^4$-Tyr$^5$-DLys(GlyShik)$^6$ -Leu$^7$-Harg$^8$-Pro$^9$-DAla$^{10}$NH$_2$
(b) 5LactD3Qal$^1$-D4ClPhe$^2$-D3Pal$^3$ -Ser$^4$-Tyr$^5$-DLys(GlyShik)$^6$ -Leu$^7$-Harg$^8$-Pro$^9$-DAla$^{10}$NH$_2$
(c) 5LactD4ClPhe$^1$-D4ClPhe$^2$-D3Pal$^3$ -Ser$^4$-Tyr$^5$-DLys-(GlyShik)$^6$ -Leu$^7$-Harg$^8$-Pro$^9$-DAla$^{10}$NH$_2$
(d) 5LactDPhe$^1$-D4ClPhe$^2$-D3Pal$^3$ -Ser$^4$-Tyr$^5$-DLys(GlyShik)$^6$ -Leu$^7$-Harg$^8$-Pro$^9$-DAla$^{10}$NH$_2$
(e) 5LactD1Nal$^1$-D4ClPhe$^2$-D3Pal$^3$ -Ser$^4$-Tyr$^5$-DLys(GlyShik)$^6$ -Leu$^7$-Harg$^8$-Pro$^9$-DAla$^{10}$NH$_2$
(f) 6LactGly$^1$-D4ClPhe$^2$-D3Pal$^3$ -Ser$^4$-Tyr$^5$-DLys(GlyShik)$^6$ -Leu$^7$-Harg$^8$-Pro$^9$-DAla$^{10}$NH$_2$
(g) 6LactD3Qal$^1$-D4ClPhe$^2$-D3Pal$^3$ -Ser$^4$-Tyr$^5$-DLys(GlyShik)$^6$ -Leu$^7$-Harg$^8$-Pro$^9$-DAla$^{10}$NH$_2$
(h) 6LactD4ClPhe$^1$-D4ClPhe$^2$-D3Pal$^3$ -Ser$^4$-Tyr$^5$-DLys-(GlyShik)$^6$ -Leu$^7$-Harg$^8$-Pro$^9$-DAla$^{10}$NH$_2$
(i) 6LactDPhe$^1$-D4ClPhe$^2$-D3Pal$^3$ -Ser$^4$-Tyr$^5$-DLys(GlyShik)$^6$ -Leu$^7$-Harg$^8$-Pro$^9$-DAla$^{10}$NH$_2$
(j) 6LactD1Nal$^1$-D4ClPhe$^2$-D3Pal$^3$ -Ser$^4$-Tyr$^5$-DLys(GlyShik)$^6$ -Leu$^7$-Harg$^8$-Pro$^9$-DAla$^{10}$NH$_2$
(k) 7LactGly$^1$-D4ClPhe$^2$-D3Pal$^3$ -Ser$^4$-Tyr$^5$-DLys(GlyShik)$^6$ -Leu$^7$-Harg$^8$-Pro$^9$-DAla$^{10}$NH$_2$
(l) 7LactD2Nal$^1$-D4ClPhe$^2$-D3Pal$^3$ -Ser$^4$-Tyr$^5$-DLys(GlyShik)$^6$ -Leu$^7$-Harg$^8$-Pro$^9$-DAla$^{10}$NH$_2$
(m) 7LactD3Qal$^1$-D4ClPhe$^2$-D3Pal$^3$ -Ser$^4$-Tyr$^5$-DLys(GlyShik)$^6$ -Leu$^7$-Harg$^8$-Pro$^9$-DAla$^{10}$NH$_2$
(n) 7LactD4ClPhe$^1$-D4ClPhe$^2$-D3Pal$^3$ -Ser$^4$-Tyr$^5$-DLys-(GlyShik)$^6$ -Leu$^7$-Harg$^8$-Pro$^9$-DAla$^{10}$NH$_2$
(o) 7LactDPhe$^1$-D4ClPhe$^2$-D3Pal$^3$ -Ser$^4$-Tyr$^5$-DLys(GlyShik)$^6$ -Leu$^7$-Harg$^8$-Pro$^9$-DAla$^{10}$NH$_2$
(p) 7LactD1Nal$^1$-D4ClPhe$^2$-D3Pal$^3$ -Ser$^4$-Tyr$^5$-DLys(GlyShik)$^6$ -Leu$^7$-Harg$^8$-Pro$^9$-DAla$^{10}$NH$_2$
(q) 6LactD2Nal$^1$-D4ClPhe$^2$-D3Pal$^3$ -Ser$^4$-Tyr$^5$-DLys(GlyShik)$^6$ -Leu$^7$-Harg$^8$-Pro$^9$-DAla$^{10}$NH$_2$

We claim:

1. A peptide of the formula:

X—B—C—D—E—F—G—H—I—J—$NH_2$ or a pharmaceutically acceptable salt thereof wherein X is a lactam group of the formula

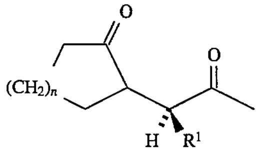

wherein n is 1, 2, or 3 and $R^1$ is selected from the group consisting of
hydrogen,
benzyl,
4-chlorobenzyl,
2-methylnaphth-1-yl,
1-methylnaphth-2-yl, and
quinolin-3-ylmethyl;

B is an aminoacyl residue selected from the group consisting of
D-phenylalanyl,
D-3-(4-chlorophenyl)alanyl,
D-3-(4-fluorophenyl)alanyl, and
D-3-(naphth-2-yl)alanyl;

C is an aminoacyl residue selected from the group consisting of
D-3-pyrid-3-yl)alanyl,
glycyl,
D-3-(naphth-1-yl)alanyl,
D-alanyl, and
D-tryptophyl;

D is an aminoacyl residue selected from the group consisting of
L-seryl,
$N^{\alpha}$-methyl-L-seryl,
glycyl, and
L-threonyl;

E is an aminioacyl residue selected from the group consisting of

L-tyrosyl,
$N^{\alpha}$-methyl-L-tyrosyl,
$N^{\alpha}$-methyl-L-phenylalanyl,
($N^{\epsilon}$-nicotinyl)-L-lysyl,
($N^{\epsilon}$-picolinyl)-L-lysyl,
L-3-(4-((3-amino-1H-1,2,4-triazol- 5-yl)amino)phenyl)alanyl, and
$N^{+}$-methyl-L-3-(4-((3-amino-1H- 1,2,4-triazol-5-yl)amino)phenyl)alanyl;

F is an aminoacyl residue selected from the group consisting of
($N^{\epsilon}$-nicotinyl)-D-lysyl,
($N^{\epsilon}$-glycyl)-D-lysyl,
($N^{\epsilon}$-nicotinylazaglycyl)-D-lysyl,
($N^{\epsilon}$-furo-2-ylazaglycyl)-D-lysyl,
D-3-(4-((3-amino-1H- 1,2,4-triazol-5-yl)amino)phenyl)alanyl,
D-lysyl(N-epsilon glycyl nicotinyl),
D-lysyl(N-epsilon furo-2-yl),
D-lysyl(N-epsilon glycyl furo-2-yl),
($N^{\epsilon}$-shikimyl)-D-lysyl,
($N^{\epsilon}$-shikimylglycyl)-D-lysyl,
D-citrullyl,
D-homocitrullyl,
D-arginyl,
D-homoarginyl,
($N^{g}$,$N^{g}$-diethyl)-D-homoarginyl, and
($N^{\epsilon}$-pyrazinyl)-D-lysyl;

G is an aminoacyl residue selected from the group consisting of
L-leucyl,
L-isoleucyl,
$N^{\alpha}$-methyl-L-leucyl,
tert-butyl-L-glycyl, and
L-valyl;

H is an aminoacyl residue selected from the group consisting of
L-arginyl,
L-homoarginyl,
($N^{\epsilon}$-isopropyl)-L-lysyl, and
($N^{g}$,$N^{g}$-diethyl)-L-homoarginyl;

I is an aminoacyl residue selected from the group consisting of
L-prolyl and
$N^{\alpha}$-methyl-L-alanyl; and J is an aminoacyl residue selected from the group consisting of
glycyl,
D-alanyl, and
sarcosyl.

2. A peptide as defined by claim 1 or a pharmaceutically acceptable salt thereof wherein X is selected from the group consisting of
2-(N-2'-pyrrolidinonyl)-2-(R)-(2-naphthylmethyl)acetyl,
2-(N-2'-pyrrolidinonyl)-2-(R)-(3-quinolinylmethyl)acetyl,
2-(N-2'-piperidinonyl)-2-(R)-(2-naphthylmethyl)acetyl,
2-(N-2'-piperidinonyl)-2-(R)-(3-quinolinylmethyl)acetyl,
2-(N-$\epsilon$-caprolactamyl)-2-(R)-(2-naphthylmethyl)acetyl, and
2-(N-$\epsilon$-caprolactamyl)-2-(R) -(3-quinolinylmethyl)-acetyl;

B is an aminoacyl residue selected from the group consisting of
D-phenylalanyl,
D-3-(4-chlorophenyl)alanyl, and
D-3-(4-fluorophenyl)alanyl;

C is an aminoacyl residue selected from the group consisting of
D-3-(pyrid-3-yl)alanyl,
D-3-(naphth-1-yl)alanyl, and
D-tryptophyl;

D is an aminoacyl residue selected from the group consisting of
L-seryl,
$N^{\alpha}$-methyl-L-seryl, and
L-threonyl;

E is an aminoacyl residue selected from the group consisting of
L-tyrosyl,
L-3-(4-((3-amino-1H-1,2,4-triazol- 5-yl)amino)phenyl)alanyl,
$N^{\alpha}$-methyl-L-tyrosyl, and
$N^{\alpha}$-methyl-L-3-(4-((3-amino-1H- 1,2,4-triazol-5-yl)amino)phenyl)alanyl;

F is an aminoacyl residue selected from the group consisting of
D-citrullyl,
D-homocitrullyl,
D-lysyl(N-epsilon nicotinyl),
D-lysyl(N-epsilon glycyl nicotinyl),
D-lysyl(N-epsilon azaglycyl nicotinyl),
D-lysyl(N-epsilon shikimyl),
D-lysyl(N-epsilon glycyl shikimyl),
D-lysyl(N-epsilon furo-2-yl),
D-lysyl(N-epsilon glycyl furo-2-yl),
D-lysyl(N-epsilon azaglycyl furo-2-yl), and
D-3-(4-((3-amino-1H-1,2,4-triazol-5-yl)amino)phenyl)alanyl;

G is an aminoacyl residue selected from the group consisting of
L-leucyl,
L-isoleucyl,
$N^{\alpha}$-methyl-L-leucyl,
tert-butyl-L-glycyl, and
L-valyl;

H is an aminoacyl residue selected from the group consisting of
L-arginyl,
L-homoarginyl,
L-lysyl($N^{\epsilon}$-isopropyl), and
L-2-amino-6-$N^{g}N^{g}$-diethyl-guanidinohexanoyl;

I is an aminoacyl residue selected from the group consisting of
L-prolyl, and
$N^{\alpha}$-methyl-L-alanyl; and J is an aminoacyl residue selected from the group consisting of
glycyl,
D-alanyl, and
sarcosyl.

3. A peptide or pharmaceutically acceptable salt thereof having the formula:

$$X—B—D3Pal—Ser—E—F—G—H—Pro—Ala—NH_2$$

wherein

X is selected from the group consisting of
2-(N-2'-pyrrolidinonyl)-2-(R)-(2-naphthylmethyl)acetyl, and 2-(N-2'-piperidinonyl)-2-(R)-(2-naphthylmethyl)acetyl; acetyl;

B is an aminoacyl residue selected from the group consisting of
D-3-(4-chlorophenyl)alanyl, and
D-3-(4-fluorophenyl)alanyl;

E is an aminoacyl residue selected from the group consisting of
L-tyrosyl,
L-3-(4-((3-amino-1H-1,2,4-triazol-5-yl)amino)phenyl)alanyl,
$N^{\alpha}$-methyl-L-tyrosyl, and
$N^{\alpha}$-methyl-L-3-(4-((3-amino-1H- 1,2,4-triazol-5-yl)amino)phenyl)alanyl;

F is an aminoacyl residue selected from the group consisting of
D-citrullyl,
D-homocitrullyl,
D-lysyl(N-epsilon nicotinyl),
D-lysyl(N-epsilon glycyl nicotinyl),
D-lysyl(N-epsilon azaglycyl nicotinyl),
D-lysyl(N-epsilon shikimyl),
D-lysyl(N-epsilon glycyl shikimyl),
D-lysyl(N-epsilon furo-2-yl),
D-lysyl(N-epsilon glycyl furo-2-yl),
D-lysyl(N-epsilon azaglycyl furo-2-yl), and
D-3-(4-((3-amino-1H-1,2,4-triazol-5-yl)amino)phenyl)alanyl;

G is an aminoacyl residue selected from the group consisting of
L-leucyl, and
$N^{\alpha}$-methyl-L-leucyl; and H is an aminoacyl residue selected from the group consisting of
L-arginyl,
L-homoarginyl,
L-lysyl(N-epsilon isopropyl), and,
L-2-amino-6-$N^g$,$N^g$-diethyl-guanidinohexanoyl.

4. A peptide or pharmaceutically acceptable salt thereof as defined by claim 1 selected from the group consisting of 5LactD2Nal$^1$-D4ClPhe$^2$-D3Pal$^3$ -Ser$^4$-NMeTyr$^5$-DCit$^6$ -Leu$^7$-Arg$^8$-Pro$^9$-DAla$^{10}$NH$_2$;

5LactD2Nal$^1$-D4ClPhe$^2$-D3Pal$^3$ -Ser$^4$-NMeTyr$^5$-DLys(N-epsilon-Shik)$^6$ -Leu$^6$-Arg$^8$-Pro$^9$-DAla$^{10}$NH$_2$;

5LactD2Nal$^1$-D4ClPhe$^2$-D3Pal$^3$ -Ser$^4$-NMeTyr$^5$-DLys(N-epsilon-Gly-Shik)$^6$ -Leu$^7$-Arg$^8$-Pro$^9$-DAla$^{10}$NH$_2$;

5LactD2Nal$^1$-D4ClPhe$^2$-D3Pal$^3$ -Ser$^4$-NMeTyr$^5$-DLys(N-epsilon-Shik)$^6$ -Leu$^7$-Arg$^8$-Pro$^9$-DAla$^{10}$NH$_2$;

5LactD2Nal$^1$-D4ClPhe$^2$-D3Pal$^3$ -Ser$^4$-NMeTyr$^5$-DLys(N-epsilon-Gly-Shik)$^6$ -Leu$^7$-Arg$^8$-Pro$^9$-DAla$^{10}$NH$_2$;

5LactD2Nal$^1$-D4ClPhe$^2$-D3Pal$^3$ -Ser$^4$-Tyr$^5$-DCit$^6$ -Leu$^7$-Arg$^8$-Pro$^9$-DAla$^{10}$NH$_2$;

5LactD2Nal$^1$-D4ClPhe$^2$-D3Pal$^3$ -Ser$^4$-NMeTyr$^5$-DLys(N-epsilon-Nic)$^6$ -Leu7-Lys(N-epsilon-Isopropyl)$^8$-Pro$^9$-DAla$^{10}$NH$_2$;

6LactD2Nal$^1$-D4ClPhe$^2$-D3Pal$^3$ -Ser$^4$-NMeTyr$^5$-DLys(N-epsilon-Shik)$^6$ -Leu$^7$-Arg$^8$-Pro$^9$-DAla$^{10}$NH$_2$;

6LactD2Nal$^1$-D4ClPhe$^2$-D3Pal$^3$ -Ser$^4$-NMeTyr$^5$-DLys(N-epsilon-Gly-Shik)$^6$ -Leu$^7$-Arg$^8$-Pro$^9$-DAla$^{10}$NH$_2$;

6LactD2Nal$^1$-D4ClPhe$^2$-D3Pal$^3$ -Ser$^4$-NMeTyr$^5$-DLys(N-epsilon-Shik)$^6$ -Leu$^7$-Harg$^8$-Pro$^9$-DAla$^{10}$NH$_2$;

6LactD2Nal$^1$-D4ClPhe$^2$-D3Pal$^3$ -Ser$^4$-NMeTyr$^5$-DLys(N-epsilon-Gly-Shik)$^6$ -Leu$^7$-Harg$^8$-Pro$^9$-DAla$^{10}$NH$_2$;

5LactD2Nal$^1$-D4ClPhe$^2$-D3Pal$^3$ -Ser$^4$-Tyr$^5$-DHCit$^6$ -Leu$^7$-Lys(isp)$^8$-Pro$^9$-DAla$^{10}$NH$_2$;

6LactD2Nal$^1$-D4ClPhe$^2$-D3Pal$^3$ -Ser$^4$-NMeTyr$^5$-DLys(N-epsilon-Nic)$^6$ -Leu$^7$-Lys(N-epsilon-Isopropyl)$^8$-Pro$^9$-DAla$^{10}$NH$_2$;

5LactGly$^1$-D4ClPhe$^2$-D1Nal$^3$ -Ser$^4$-NMeTyr$^5$-DCit$^6$ -Leu$^7$-Arg$^8$-Pro$^9$-DAla$^{10}$NH$_2$;

5LactD2Nal$^1$-D4ClPhe$^2$-D3Pal$^3$ -Ser$^4$-NMePhe(Atz)$^5$-DLys(Nic)$^6$ -Leu$^7$-Lys(N-epsilon-Isopropyl)$^8$-Pro$^9$-DAla$^{10}$NH$_2$;

5LactD2Nal$^1$-D4ClPhe$^2$-D3Pal$^3$ -Ser$^4$-NMeTyr$^5$-DLys(Atz)$^6$ -Leu$^7$-Lys(N-epsilon-Isopropyl)$^8$-Pro$^9$-DAla$^{10}$NH$_2$;

5LactD2Nal$^1$-D4ClPhe$^2$-D3Pal$^3$ -Ser$^4$-NMeTyr$^5$-DLys-(Nic)$^6$ -Leu$^7$-Lys(N-epsilon-1-hydroxy-isopropyl)$^8$-Pro$^9$-DAla$^{10}$NH$_2$;

5LactD2Nal$^1$-D4ClPhe$^2$-D3Pal$^3$ -Ser$^4$-NMeTyr$^5$-DLys-(Nic)$^6$ -Leu$^7$-Lys(Isp)$^8$-NMeAla$^9$-DAla$^{10}$NH$_2$;

5LactD2Nal$^1$-D4ClPhe$^2$-D3Pal$^3$ -Ser$^4$-Phe(Atz)$^5$-DPhe(Atz)$^6$ -Leu$^7$-Lys(N-epsilon-Isopropyl)$^8$-Pro$^9$-DAla$^{10}$NH$_2$;

5LactD2Nal$^1$-D4ClPhe$^2$-D3Pal$^3$ -Ser$^4$-Tyr$^5$-DHarg(Et$_2$)$^6$ -Leu$^7$-HArg(Et$_2$)$^8$-Pro$^9$-DAla$^{10}$NH$_2$;

5LactD2Nal$^1$-D4ClPhe$^2$-D3Pal$^3$ -Ser$^4$-Tyr$^5$-DLys(Shik)$^6$ -Leu$^7$-Arg$^8$-Pro$^9$-DAla$^{10}$NH$_2$;

5LactD2Nal$^1$-D4ClPhe$^2$-D3Pal$^3$ -Ser$^4$-Tyr$^5$-DLys(Gly-Shik)$^6$ -Leu$^7$-Arg$^8$-Pro$^9$-DAla$^{10}$NH$_2$; and 5LactD2Nal$^1$-D4ClPhe$^2$-D3Pal$^3$ -Ser$^4$-Tyr$^5$-DLys(Gly-Shik)$^6$ -Leu$^7$-Harg$^8$-Pro$^9$-DAla$^{10}$NH$_2$.

5. A composition comprising an amount of a peptide as defined by claim 1 or a pharmaceutically acceptable salt thereof effective to control the release of LHRH in a mammal in combination with a pharmaceutically acceptable carrier.

6. A method of controlling the release of LHRH in a mammal in need of such treatment comprising administering an effective amount of a peptide as defined by claim 1 or a pharmaceutically acceptable salt thereof.

* * * * *

UNITED STATES PATENT AND TRADEMARK OFFICE

CERTIFICATE OF CORRECTION

PATENT NO. : 5,516,759

DATED : May 14, 1996

INVENTOR(S) : R. E. Swenson, et. Al.

It is certified that error appears in the above-indentified patent and that said Letters Patent is hereby corrected as shown below:

Column 39, line 8, change "$N^{+}$" to --$N^{\alpha}$--.

Column 41, line 2, delete the second occurrence of "acetyl;".

Column 41, line 39, change "$N^{g}$,$N^{g}$" to --Ng Ng--.

Column 41, line 45, change "$Leu^{6}$" to --$Leu^{7}$--.

Column 41, line 51, change "$Arg^{8}$" to --$Harg^{8}$--.

Column 41, line 53, change "$Arg^{8}$" to --$Harg^{8}$--.

Column 42, line 2, change "$Leu_{7}$" to --$Leu^{7}$--.

Signed and Sealed this

Fourth Day of March, 1997

Attest:

BRUCE LEHMAN

*Attesting Officer* *Commissioner of Patents and Trademarks*